(12) United States Patent
Martinborough et al.

(10) Patent No.: US 8,129,546 B2
(45) Date of Patent: Mar. 6, 2012

(54) DERIVATIVES FOR MODULATION OF ION CHANNELS

(75) Inventors: Esther Martinborough, San Diego, CA (US); Andreas P. Termin, Encinitas, CA (US); Timothy D. Neubert, San Diego, CA (US); Nicole Hilgraf, San Diego, CA (US); Corey Anderson, San Diego, CA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 12/879,237

(22) Filed: Sep. 10, 2010

(65) Prior Publication Data

US 2011/0077269 A1 Mar. 31, 2011

Related U.S. Application Data

(62) Division of application No. 11/584,961, filed on Oct. 23, 2006, now Pat. No. 7,842,819.

(60) Provisional application No. 60/729,344, filed on Oct. 21, 2005.

(51) Int. Cl.
*C07D 209/04* (2006.01)
*A61K 31/405* (2006.01)

(52) U.S. Cl. ..................................... 548/510; 514/415

(58) Field of Classification Search .................. 548/510; 514/415
See application file for complete search history.

(56) References Cited

U.S. PATENT DOCUMENTS

| | | | |
|---|---|---|---|
| 7,605,174 B2 | 10/2009 | Neubert et al. | |
| 7,615,563 B2 | 11/2009 | Gonzalez, III et al. | |
| 7,683,083 B2 | 3/2010 | Martinborough et al. | |
| 7,745,629 B2 | 6/2010 | Termin et al. | |
| 7,786,137 B2 | 8/2010 | Kawatkar et al. | |
| 7,842,819 B2 | 11/2010 | Martinborough et al. | |
| 7,846,954 B2 | 12/2010 | Zimmermann et al. | |
| 7,855,220 B2 | 12/2010 | Neubert et al. | |
| 2005/0137190 A1 | 6/2005 | Gonzalez et al. | |
| 2006/0025415 A1 | 2/2006 | Gonzalez et al. | |
| 2007/0117801 A1 | 5/2007 | Neubert et al. | |
| 2007/0203130 A1 | 8/2007 | Neubert et al. | |
| 2008/0027067 A1 | 1/2008 | Martinborough et al. | |
| 2008/0113990 A1 | 5/2008 | Martinborough et al. | |
| 2008/0119453 A1 | 5/2008 | Termin et al. | |
| 2008/0293737 A1 | 11/2008 | Martinborough et al. | |
| 2009/0012117 A1 | 1/2009 | Kawatkar et al. | |
| 2009/0105271 A1 | 4/2009 | Martinborough et al. | |
| 2009/0124655 A1 | 5/2009 | Stamos et al. | |
| 2009/0131440 A1 | 5/2009 | Stamos et al. | |
| 2009/0326023 A1 | 12/2009 | Neubert et al. | |
| 2010/0087479 A1 | 4/2010 | Gonzalez, III et al. | |
| 2010/0130548 A1 | 5/2010 | Martinborough et al. | |
| 2010/0204255 A1 | 8/2010 | Termin et al. | |
| 2011/0059965 A1 | 3/2011 | Kawatkar et al. | |
| 2011/0082117 A1 | 4/2011 | Martinborough et al. | |
| 2011/0098328 A1 | 4/2011 | Hilgraf et al. | |
| 2011/0112156 A1 | 5/2011 | Neubert et al. | |

FOREIGN PATENT DOCUMENTS

WO WO 2004104001 A2 * 12/2004
WO 2005013914 2/2005

OTHER PUBLICATIONS

Kubinyi (3D QSAR in Drug Design: Ligand-Protein Interactions and Molecular Similarity, vol. 2-3, Springer, 1998, 800 pages). TOC and pp. 243-244 provided.*
Park et al. (Toxicology Lett., 120 (2001), 281-91).*
Wermuth, The Practice of Medicinal Chemsitry, 2d ed. (2003), 768 pages. Chs. 9-10 provided.*

* cited by examiner

*Primary Examiner* — Robert Havlin
(74) *Attorney, Agent, or Firm* — Michael J. DiVerdi

(57) ABSTRACT

Sulfonamide derivatives act as ion channel antagonists. The compositions are useful for treating or relieving pain-related conditions.

54 Claims, No Drawings

DERIVATIVES FOR MODULATION OF ION CHANNELS

CROSS-REFERENCE TO RELATED APPLICATIONS

The present application is a divisional of U.S. patent application Ser. No. 11/584,961 filed Oct. 23, 2006, which claims the benefit of priority to U.S. Provisional Application No. 60/729,344, filed on Oct. 21, 2005. The entire contents of both applications are incorporated herein by reference.

TECHNICAL FIELD OF THE INVENTION

The present invention relates to compounds useful as inhibitors of ion channels. The invention also provides pharmaceutically acceptable compositions comprising the compounds of the invention and methods of using the compositions in the treatment of various disorders.

BACKGROUND OF THE INVENTION

Na channels are central to the generation of action potentials in all excitable cells such as neurons and myocytes. They play key roles in excitable tissue including brain, smooth muscles of the gastrointestinal tract, skeletal muscle, the peripheral nervous system, spinal cord and airway. As such they play key roles in a variety of disease states such as epilepsy (See, Moulard, B. and D. Bertrand (2002) "Epilepsy and sodium channel blockers" *Expert Opin. Ther. Patents* 12(1): 85-91)), pain (See, Waxman, S. G., S. Dib-Hajj, et al. (1999) "Sodium channels and pain" *Proc Natl Acad Sci USA* 96(14): 7635-9 and Waxman, S. G., T. R. Cummins, et al. (2000) "Voltage-gated sodium channels and the molecular pathogenesis of pain: a review" *J Rehabil Res Dev* 37(5): 517-28), myotonia (See, Meola, G. and V. Sansone (2000) "Therapy in myotonic disorders and in muscle channelopathies" *Neurol Sci* 21(5): S953-61 and Mankodi, A. and C. A. Thornton (2002) "Myotonic syndromes" *Curr Opin Neurol* 15(5): 545-52), ataxia (See, Meisler, M. H., J. A. Kearney, et al. (2002) "Mutations of voltage-gated sodium channels in movement disorders and epilepsy" *Novartis Found Symp* 241: 72-81), multiple sclerosis (See, Black, J. A., S. Dib-Hajj, et al. (2000) "Sensory neuron-specific sodium channel SNS is abnormally expressed in the brains of mice with experimental allergic encephalomyelitis and humans with multiple sclerosis" *Proc Natl Acad Sci USA* 97(21): 11598-602, and Renganathan, M., M. Gelderblom, et al. (2003) "Expression of Na(v)1.8 sodium channels perturbs the firing patterns of cerebellar purkinje cells" *Brain Res* 959(2): 235-42), irritable bowel (See, Su, X., R. E. Wachtel, et al. (1999) "Capsaicin sensitivity and voltage-gated sodium currents in colon sensory neurons from rat dorsal root ganglia" *Am J Physiol* 277(6 Pt 1): G1180-8, and Laird, J. M., V. Souslova, et al. (2002) "Deficits in visceral pain and referred hyperalgesia in Nav1.8 (SNS/PN3)-null mice" *J Neurosci* 22(19): 8352-6), urinary incontinence and visceral pain (See, Yoshimura, N., S. Seki, et al. (2001) "The involvement of the tetrodotoxin-resistant sodium channel Na(v)1.8 (PN3/SNS) in a rat model of visceral pain" *J Neurosci* 21(21): 8690-6), as well as an array of psychiatry dysfunctions such as anxiety and depression (See, Hurley, S. C. (2002) "Lamotrigine update and its use in mood disorders" *Ann Pharmacother* 36(5): 860-73).

Voltage gated Na channels comprise a gene family consisting of 9 different subtypes (NaV1.1-NaV1.9). As shown in Table A, these subtypes show tissue specific localization and functional differences (See, Goldin, A. L. (2001) "Resurgence of sodium channel research" *Annu Rev Physiol* 63: 871-94). Three members of the gene family (NaV1.8, 1.9, 1.5) are resistant to block by the well-known Na channel blocker TTX, demonstrating subtype specificity within this gene family. Mutational analysis has identified glutamate 387 as a critical residue for TTX binding (See, Noda, M., H. Suzuki, et al. (1989) "A single point mutation confers tetrodotoxin and saxitoxin insensitivity on the sodium channel II" *FEBS Lett* 259(1): 213-6).

TABLE A (Abbreviations: CNS = central nervous system, PNS = peripheral nervous system, DRG = dorsal root ganglion, TG = Trigeminal ganglion):

| Na isoform | Tissue | TTX IC50 | Indications |
|---|---|---|---|
| NaV1.1 | CNS, PNS soma of neurons | 10 nM | Pain, Epilepsy, neurodegeneration |
| NaV1.2 | CNS, high in axons | 10 nM | Neurodegeneration Epilepsy |
| NaV1.3 | CNS, embryonic, injured nerves | 15 nM | Pain |
| NaV1.4 | Skeletal muscle | 25 nM | Myotonia |
| NaV1.5 | Heart | 2 µM | Arrythmia, long QT |
| NaV1.6 | CNS widespread, most abuntant | 6 nM | Pain, movement disorders |
| NaV1.7 | PNS, DRG, terminals neuroendocrine | 25 nM | Pain, Neuroendocrine disorders |
| NaV1.8 | PNS, small neurons in DRG & TG | >50 µM | Pain |
| NaV1.9 | PNS, small neurons in DRG & TG | 1 µM | Pain |

In general, voltage-gated sodium channels (NaVs) are responsible for initiating the rapid upstroke of action potentials in excitable tissue in nervous system, which transmit the electrical signals that compose and encode normal and aberrant pain sensations. Antagonists of NaV channels can attenuate these pain signals and are useful for treating a variety of pain conditions, including but not limited to acute, chronic, inflammatory, and neuropathic pain. Known NaV antagonists, such as TTX, lidocaine (See, Mao, J. and L. L. Chen (2000) "Systemic lidocaine for neuropathic pain relief" *Pain* 87(1): 7-17.), bupivacaine, phenyloin (See, Jensen, T. S. (2002) "Anticonvulsants in neuropathic pain: rationale and clinical evidence" *Eur J Pain* 6 (Suppl A): 61-8), lamotrigine (See, Rozen, T. D. (2001) "Antiepileptic drugs in the management of cluster headache and trigeminal neuralgia" *Headache* 41 Suppl 1: S25-32 and Jensen, T. S. (2002) "Anticonvulsants in neuropathic pain: rationale and clinical evidence" *Eur J Pain* 6 (Suppl A): 61-8.), and carbamazepine (See, Backonja, M. M. (2002) "Use of anticonvulsants for treatment of neuropathic pain" *Neurology* 59(5 Suppl 2): S14-7), have been shown to be useful attenuating pain in humans and animal models.

Hyperalgesia (extreme sensitivity to something painful) that develops in the presence of tissue injury or inflammation reflects, at least in part, an increase in the excitability of high-threshold primary afferent neurons innervating the site of injury. Voltage sensitive sodium channels activation is critical for the generation and propagation of neuronal action potentials. There is a growing body of evidence indicating that modulation of NaV currents is an endogenous mechanism used to control neuronal excitability (See, Goldin, A. L. (2001) "Resurgence of sodium channel research" *Annu Rev Physiol* 63: 871-94.). Several kinetically and pharmacologically distinct voltage-gated sodium channels are found in dorsal root ganglion (DRG) neurons. The TTX-resistant current is insensitive to micromolar concentrations of tetrodotoxin, and displays slow activation and inactivation kinetics and a more depolarized activation threshold when compared to other voltage-gated sodium channels. TTX-resistant sodium currents are primarily restricted to a subpopulation of sensory neurons likely to be involved in nociception. Specifically, TTX-resistant sodium currents are expressed almost exclusively in neurons that have a small cell-body diameter and give rise to small-diameter slow-conducting axons and that are responsive to capsaicin. A large body of experimental evidence demonstrates that TTX-resistant sodium channels are expressed on C-fibers and are important in the transmission of nociceptive information to the spinal cord.

Intrathecal administration of antisense oligo-deoxynucleotides targeting a unique region of the TTX-resistant sodium channel (NaV1.8) resulted in a significant reduction in $PGE_2$-induced hyperalgesia (See, Khasar, S. G., M. S. Gold, et al. (1998) "A tetrodotoxin-resistant sodium current mediates inflammatory pain in the rat" *Neurosci Lett* 256(1): 17-20). More recently, a knockout mouse line was generated by Wood and colleagues, which lacks functional NaV1.8. The mutation has an analgesic effect in tests assessing the animal's response to the inflammatory agent carrageenan (See, Akopian, A. N., V. Souslova, et al. (1999) "The tetrodotoxin-resistant sodium channel SNS has a specialized function in pain pathways" *Nat Neurosci* 2(6): 541-8.). In addition, deficit in both mechano- and thermoreception were observed in these animals. The analgesia shown by the Nav1.8 knockout mutants is consistent with observations about the role of TTX-resistant currents in nociception.

Immunohistochemical, in-situ hybridization and in-vitro electrophysiology experiments have all shown that the sodium channel NaV1.8 is selectively localized to the small sensory neurons of the dorsal root ganglion and trigeminal ganglion (See, Akopian, A. N., L. Sivilotti, et al. (1996) "A tetrodotoxin-resistant voltage-gated sodium channel expressed by sensory neurons" *Nature* 379(6562): 257-62.). The primary role of these neurons is the detection and transmission of nociceptive stimuli. Antisense and immunohistochemical evidence also supports a role for NaV1.8 in neuropathic pain (See, Lai, J., M. S. Gold, et al. (2002) "Inhibition of neuropathic pain by decreased expression of the tetrodotoxin-resistant sodium channel, NaV1.8." *Pain* 95(1-2): 143-52, and Lai, J., J. C. Hunter, et al. (2000) "Blockade of neuropathic pain by antisense targeting of tetrodotoxin-resistant sodium channels in sensory neurons" *Methods Enzymol* 314: 201-13.). NaV1.8 protein is upregulated along uninjured C-fibers adjacent to the nerve injury. Antisense treatment prevents the redistribution of NaV1.8 along the nerve and reverses neuropathic pain. Taken together the gene-knockout and antisense data support a role for NaV1.8 in the detection and transmission of inflammatory and neuropathic pain.

In neuropathic pain states, there is a remodeling of Na channel distribution and subtype. In the injured nerve, expression of NaV1.8 and NaV1.9 are greatly reduced whereas expression of the TTX sensitive subunit NaV1.3 is 5-10 fold upregulated (See, Dib-Hajj, S. D., J. Fjell, et al. (1999) "Plasticity of sodium channel expression in DRG neurons in the chronic constriction injury model of neuropathic pain." *Pain* 83(3): 591-600.) The timecourse of the increase in NaV1.3 parallels the appearance of allodynia in animal models subsequent to nerve injury. The biophysics of the NaV1.3 channel is distinctive in that it shows very fast repriming after inactivation following an action potential. This allows for sustained rates of high firing as is often seen in the injured nerve (See, Cummins, T. R., F. Aglieco, et al. (2001) "Nav1.3 sodium channels: rapid repriming and slow closed-state inactivation display quantitative differences after expression in a mammalian cell line and in spinal sensory neurons" *J Neurosci* 21(16): 5952-61.). NaV1.3 is expressed in the central and peripheral systems of man. NaV1.9 is similar to NaV1.8 as it is selectively localized to small sensory neurons of the dorsal root ganglion and trigeminal ganglion (See, Fang, X., L. Djouhri, et al. (2002). "The presence and role of the tetrodotoxin-resistant sodium channel Na(v)1.9 (NaN) in nociceptive primary afferent neurons." *J Neurosci* 22(17): 7425-33.). It has a slow rate of inactivation and left-shifted voltage dependence for activation (See, Dib-Hajj, S., J. A. Black, et al. (2002) "NaN/Nav1.9: a sodium channel with unique properties" *Trends Neurosci* 25(5): 253-9.). These two biophysical properties allow NaV1.9 to play a role in establishing the resting membrane potential of nociceptive neurons. The resting membrane potential of NaV1.9 expressing cells is in the −55 to −50 mV range compared to −65 mV for most other peripheral and central neurons. This persistent depolarization is in large part due to the sustained low-level activation of NaV1.9 channels. This depolarization allows the neurons to more easily reach the threshold for firing action potentials in response to nociceptive stimuli. Compounds that block the NaV1.9 channel may play an important role in establishing the set point for detection of painful stimuli. In chronic pain states, nerve and nerve ending can become swollen and hypersensitive exhibiting high frequency action potential firing with mild or even no stimulation. These pathologic nerve swellings are termed neuromas and the primary Na channels expressed in them are NaV1.8 and NaV1.7 (See, Kretschmer, T., L. T. Happel, et al. (2002) "Accumulation of PN1 and PN3 sodium channels in painful human neuroma-evidence from immunocytochemistry" *Acta Neurochir* (*Wien*) 144(8): 803-10; discussion 810.). NaV1.6 and NaV1.7 are also expressed in dorsal root ganglion neurons and contribute to the small TTX sensitive component seen in these cells. NaV1.7 in particular may therefore be a potential pain target in addition to its role in neuroendocrine excitability (See, Klugbauer, N., L. Lacinova, et al. (1995) "Structure and functional expression of a new member of the tetrodotoxin-sensitive voltage-activated sodium channel family from human neuroendocrine cells" *Embo J* 14(6): 1084-90).

NaV1.1 (See, Sugawara, T., E. Mazaki-Miyazaki, et al. (2001) "Nav1.1 mutations cause febrile seizures associated with afebrile partial seizures." *Neurology* 57(4): 703-5.) and NaV1.2 (See, Sugawara, T., Y. Tsurubuchi, et al. (2001) "A missense mutation of the Na+ channel alpha II subunit gene Na(v)1.2 in a patient with febrile and afebrile seizures causes channel dysfunction" *Proc Natl Acad Sci USA* 98(11): 6384-9) have been linked to epilepsy conditions including febrile seizures. There are over 9 genetic mutations in NaV1.1 associated with febrile seizures (See, Meisler, M. H., J. A. Kearney, et al. (2002) "Mutations of voltage-gated sodium channels in movement disorders and epilepsy" *Novartis Found Symp* 241: 72-81)

Antagonists for NaV1.5 have been developed and used to treat cardiac arrhythmias. A gene defect in NaV1.5 that produces a larger noninactivating component to the current has been linked to long QT in man and the orally available local anesthetic mexilitine has been used to treat this condition (See, Wang, D. W., K. Yazawa, et al. (1997) "Pharmacological targeting of long QT mutant sodium channels." *J Clin Invest* 99(7): 1714-20).

Several Na channel blockers are currently used or being tested in the clinic to treat epilepsy (See, Moulard, B. and D.

Bertrand (2002) "Epilepsy and sodium channel blockers" *Expert Opin. Ther. Patents* 12(1): 85-91.); acute (See, Wiffen, P., S. Collins, et al. (2000) "Anticonvulsant drugs for acute and chronic pain" *Cochrane Database Syst Rev* 3), chronic (See, Wiffen, P., S. Collins, et al. (2000) "Anticonvulsant drugs for acute and chronic pain" *Cochrane Database Syst Rev* 3, and Guay, D. R. (2001) "Adjunctive agents in the management of chronic pain" *Pharmacotherapy* 21(9): 1070-81), inflammatory (See, Gold, M. S. (1999) "Tetrodotoxin-resistant Na+ currents and inflammatory hyperalgesia." *Proc Natl Acad Sci USA* 96(14): 7645-9), and neuropathic pain (See, Strichartz, G. R., Z. Zhou, et al. (2002) "Therapeutic concentrations of local anesthetics unveil the potential role of sodium channels in neuropathic pain" *Novartis Found Symp* 241: 189-201, and Sandner-Kiesling, A., G. Rumpold Seitlinger, et al. (2002) "Lamotrigine monotherapy for control of neuralgia after nerve section" *Acta Anaesthesiol Scand* 46(10): 1261-4); cardiac arrhythmias (See, An, R. H., R. Bangalore, et al. (1996) "Lidocaine block of LQT-3 mutant human Na+ channels" *Circ Res* 79(1): 103-8, and Wang, D. W., K. Yazawa, et al. (1997) "Pharmacological targeting of long QT mutant sodium channels" *J Clin Invest* 99(7): 1714-20); for neuroprotection (See, Taylor, C. P. and L. S. Narasimhan (1997) "Sodium channels and therapy of central nervous system diseases" *Adv Pharmacol* 39: 47-98) and as anesthetics (See, Strichartz, G. R., Z. Zhou, et al. (2002) "Therapeutic concentrations of local anesthetics unveil the potential role of sodium channels in neuropathic pain." *Novartis Found Symp* 241: 189-201).

Various animal models with clinical significance have been developed for the study of sodium channel modulators for numerous different pain indications. E.g., malignant chronic pain, see, Kohase, H., et al., Acta Anaesthesiol Scand. 2004; 48(3):382-3; femur cancer pain (see, Kohase, H., et al., Acta Anaesthesiol Scand. 2004; 48(3):382-3); non-malignant chronic bone pain (see, Ciocon, J. O. et al., J Am Geriatr Soc. 1994; 42(6):593-6); rheumatoid arthritis (see, Calvino, B. et al., Behav Brain Res. 1987; 24(1):11-29); osteoarthritis (see, Guzman, R. E., et al., Toxicol Pathol. 2003; 31(6):619-24); spinal stenosis (see, Takenobu, Y. et al., J Neurosci Methods. 2001; 104(2):191-8); neuropathic low back pain (see, Hines, R., et al., Pain Med. 2002; 3(4):361-5; Massie, J. B., et al., J Neurosci Methods. 2004; 137(2):283-9); myofascial pain syndrome (see, Dalpiaz & Dodds, J Pain Palliat Care Pharmacother. 2002; 16(1):99-104; Sluka K A et al., Muscle Nerve. 2001; 24(1):37-46); fibromyalgia (see, Bennet & Tai, Int J Clin Pharmacol Res. 1995; 15(3):115-9); temporomandibular joint pain (see, Ime H, Ren K, Brain Res Mol Brain Res. 1999; 67(1):87-97); chronic visceral pain, including abdominal (see, Al-Chaer, E. D., et al., Gastroenterology. 2000; 119(5):1276-85); pelvic/perineal pain, (see, Wesselmann et al., Neurosci Lett. 1998; 246(2):73-6); pancreatic (see, Vera-Portocarrero, L. B., et al., Anesthesiology. 2003; 98(2):474-84); IBS pain (see, Verne, G. N., et al., Pain. 2003; 105(1-2):223-30; La J H et al., World Gastroenterol. 2003; 9(12):2791-5); chronic headache pain (see, Williams & Stark, Cephalalgia. 2003; 23(10):963-71); migraine (see, Yamamura, H., et al., J Neurophysiol. 1999; 81(2):479-93); tension headache, including cluster headaches (see, Costa, A., et al., Cephalalgia. 2000; 20(2):85-91); chronic neuropathic pain, including post-herpetic neuralgia (see, Attal, N., et al., Neurology. 2004; 62(2):218-25; Kim & Chung 1992, Pain 50:355); diabetic neuropathy (see, Beidoun A et al., Clin J Pain. 2004; 20(3):174-8; Courteix, C., et al., Pain. 1993; 53(1):81-8); HIV-associated neuropathy (see, Portegies & Rosenberg, Ned Tijdschr Geneeskd. 2001; 145(15):731-5; Joseph E K et al., Pain. 2004; 107(1-2):147-58; Oh, S. B., et al., J Neurosci. 2001; 21(14):5027-35); trigeminal neuralgia (see, Sato, J., et al., Oral Surg Oral Med Oral Pathol Oral Radiol Endod. 2004; 97(1):18-22; Imamura Y et al., Exp Brain Res. 1997; 116(1):97-103); Charcot-Marie Tooth neuropathy (see, Sereda, M., et al., Neuron. 1996; 16(5):1049-60); hereditary sensory neuropathies (see, Lee, M. J., et al., Hum Mol Genet. 2003; 12(15):1917-25); peripheral nerve injury (see, Attal, N., et al., Neurology. 2004; 62(2):218-25; Kim & Chung 1992, Pain 50:355; Bennett & Xie, 1988, Pain 33:87; Decostered, I. & Woolf, C. J., 2000, Pain 87:149; Shir, Y. & Seltzer, Z. 1990; Neurosci Lett 115:62); painful neuromas (see, Nahabedian & Johnson, Ann Plast Surg. 2001; 46(1):15-22; Devor & Raber, Behav Neural Biol. 1983; 37(2):276-83); ectopic proximal and distal discharges (see, Liu, X. et al., Brain Res. 2001; 900(1):119-27); radiculopathy (see, Devers & Galer, (see, Clin J Pain. 2000; 16(3):205-8; Hayashi N et al., Spine. 1998; 23(8):877-85); chemotherapy induced neuropathic pain (see, Aley, K. O., et al., Neuroscience. 1996; 73(1):259-65); radiotherapy-induced neuropathic pain; post-mastectomy pain (see, Devers & Galer, Clin J Pain. 2000; 16(3):205-8); central pain (Cahana, A., et al., Anesth Analg. 2004; 98(6):1581-4), spinal cord injury pain (see, Hains, B. C., et al., Exp Neurol. 2000; 164(2):426-37); post-stroke pain; thalamic pain (see, LaBuda, C. J., et al., Neurosci Lett. 2000; 290(1):79-83); complex regional pain syndrome (see, Wallace, M. S., et al., Anesthesiology. 2000; 92(1):75-83; Xantos D et al., J Pain. 2004; 5(3 Suppl 2):S1); phanton pain (see, Weber, W. E., Ned Tijdschr Geneeskd. 2001; 145(17):813-7; Levitt & Heyback, Pain. 1981; 10(1):67-73); intractable pain (see, Yokoyama, M., et al., Can J Anaesth. 2002; 49(8):810-3); acute pain, acute post-operative pain (see, Koppert, W., et al., Anesth Analg. 2004; 98(4):1050-5; Brennan, T. J., et al., Pain. 1996; 64(3):493-501); acute musculoskeletal pain; joint pain (see, Gotoh, S., et al., Ann Rheum Dis. 1993; 52(11):817-22); mechanical low back pain (see, Kehl, L. J., et al., Pain. 2000; 85(3):333-43); neck pain; tendonitis; injury/exercise pain (see, Sesay, M., et al., Can J Anaesth. 2002; 49(2):137-43); acute visceral pain, including abdominal pain; pyelonephritis; appendicitis; cholecystitis; intestinal obstruction; hernias; etc (see, Giambernardino, M. A., et al., Pain. 1995; 61(3):459-69); chest pain, including cardiac Pain (see, Vergona, R. A., et al., Life Sci. 1984; 35(18):1877-84); pelvic pain, renal colic pain, acute obstetric pain, including labor pain (see, Segal, S., et al., Anesth Analg. 1998; 87(4):864-9); cesarean section pain; acute inflammatory, burn and trauma pain; acute intermittent pain, including endometriosis (see, Cason, A. M., et al., Horm Behay. 2003; 44(2):123-31); acute herpes zoster pain; sickle cell anemia; acute pancreatitis (see, Toma, H; Gastroenterology. 2000; 119(5):1373-81); breakthrough pain; orofacial pain, including sinusitis pain, dental pain (see, Nusstein, J., et al., J Endod. 1998; 24(7):487-91; Chidiac, J. J., et al., Eur J Pain. 2002; 6(1):55-67); multiple sclerosis (MS) pain (see, Sakurai & Kanazawa, J Neurol Sci. 1999; 162(2):162-8); pain in depression (see, Greene B, Curr Med Res Opin. 2003; 19(4):272-7); leprosy pain; behcet's disease pain; adiposis dolorosa (see, Devillers & Oranje, Clin Exp Dermatol. 1999; 24(3):240-1); phlebitic pain; Guillain-Barre pain; painful legs and moving toes; Haglund syndrome; erythromelalgia pain (see, Legroux-Crespel, E., et al., Ann Dermatol Venereol. 2003; 130(4):429-33); Fabry's disease pain (see, Germain, D. P., J Soc Biol. 2002; 196(2):183-90); Bladder and urogenital disease, including urinary incontinence (see, Berggren, T., et al., J Urol. 1993; 150(5 Pt 1):1540-3); hyperactivity bladder (see, Chuang, Y. C., et al., Urology. 2003; 61(3):664-70); painful bladder syndrome (see, Yoshimura, N., et al., J Neurosci. 2001; 21(21):8690-6); interstitial cyctitis (IC) (see, Giannakopoulos& Campilomatos, Arch Ital Urol Nefrol Androl. 1992; 64(4):337-9; Boucher, M., et al., J Urol. 2000; 164(1):203-8); and prostatitis (see, Mayersak, J. S., Int Surg. 1998; 83(4):347-9; Keith, I. M., et al., J Urol. 2001; 166(1):323-8).

Voltage-gated calcium channels are membrane-spanning, multi-subunit proteins that open in response to membrane depolarization, allowing Ca entry from the extracellular milieu. Calcium channels were initially classified based on the time and voltage-dependence of channel opening and on the sensitivity to pharmacological block. The categories were low-voltage activated (primarily T-type) and high-voltage activated (L, N, P, Q or R-type). This classification scheme was replaced by a nomenclature based upon the molecular subunit composition, as summarized in Table B (Hockerman G H, Peterson B Z, Johnson B D, Catterall W A. 1997. *Annu Rev Pharmacol Toxicol* 37: 361-96; Striessnig J. 1999. *Cell Physiol Biochem* 9: 242-69). There are four primary subunit types that make up calcium channels—$\alpha_1$, $\alpha_2\delta$, $\beta$ and $\gamma$ (See, e.g., De Waard et al. Structural and functional diversity of voltage-activated calcium channels. In Ion Channels, (ed. T. Narahashi) 41-87, (Plenum Press, New York, 1996)). The $\alpha_1$ subunit is the primary determinant of the pharmacological properties and contains the channel pore and voltage sensor (Hockerman et al., 1997; Striessnig, 1999). Ten isoforms of the $\alpha_1$ subunit are known, as indicated in Table I below. The $\alpha_2\delta$ subunit consists of two disulfide linked subunits, $\alpha_2$, which is primarily extracellular, and a transmembrane $\delta$ subunit. Four isoforms of $\alpha_2\delta$ are known, $\alpha_2\delta$-1, $\alpha_2\delta$-2, $\alpha_2\delta$-3 and $\alpha_2\delta$-4. The $\beta$ subunit is a non-glycosylated cytoplasmic protein that binds to the $\alpha_1$ subunit. Four isoforms are known, termed $\beta_1$ to $\beta_4$. The $\gamma$ subunit is a transmembrane protein that has been biochemically isolated as a component of $Ca_v1$ and $Ca_v2$ channels. At least 8 isoforms are known ($\gamma_1$ to $\gamma_8$) [Kang M G, Campbell K P. 2003. *J Biol Chem* 278: 21315-8]. The nomenclature for voltage-gated calcium channels is based upon the content of the $\alpha_1$ subunit, as indicated in Table I. Each type of $\alpha_1$ subunit can associate with a variety of $\beta$, $\alpha_2\delta$ or $\gamma$ subunits, so that each $Ca_v$ type corresponds to many different combinations of subunits.

TABLE B

| Cav Nomenclature | $\alpha_1$ subunit | Pharmacological name |
|---|---|---|
| $Ca_v1.1$ | $\alpha_{1S}$ | L-type |
| $Ca_v1.2$ | $\alpha_{1C}$ | L-type |
| $Ca_v1.3$ | $\alpha_{1D}$ | L-type |
| $Ca_v1.4$ | $\alpha_{1F}$ | |
| $Ca_v2.1$ | $\alpha_{1A}$ | P- or Q-type |
| $Ca_v2.2$ | $\alpha_{1B}$ | N-type |
| $Ca_v2.3$ | $\alpha_{1E}$ | R-type |
| $Ca_v3.1$ | $\alpha_{1G}$ | T-type |
| $Ca_v3.2$ | $\alpha_{1H}$ | T-type |
| $Ca_v3.3$ | $\alpha_{1I}$ | T-type |

$Ca_v2$ currents are found almost exclusively in the central and peripheral nervous system and in neuroendocrine cells and constitute the predominant forms of presynaptic voltage-gated calcium current. Presynaptic action potentials cause channel opening, and neurotransmitter release is steeply dependent upon the subsequent calcium entry. Thus, $Ca_v2$ channels play a central role in mediating neurotransmitter release.

$Ca_v2.1$ and $Ca_v2.2$ contain high affinity binding sites for the peptide toxins ω-conotoxin-MVIIC and ω-conotoxin-GVIA, respectively, and these peptides have been used to determine the distribution and function of each channel type. $Ca_v2.2$ is highly expressed at the presynaptic nerve terminals of neurons from the dorsal root ganglion and neurons of lamina I and II of the dorsal horn (Westenbroek R E, Hoskins L, Catterall W A. 1998. *J Neurosci* 18: 6319-30; Cizkova D, Marsala J, Lukacova N, Marsala M, Jergova S, et al. 2002. *Exp Brain Res* 147: 456-63). $Ca_v2.2$ channels are also found in presynaptic terminals between second and third order interneurons in the spinal cord. Both sites of neurotransmission are very important in relaying pain information to the brain.

Pain can be roughly divided into three different types: acute, inflammatory, and neuropathic. Acute pain serves an important protective function in keeping the organism safe from stimuli that may produce tissue damage. Severe thermal, mechanical, or chemical inputs have the potential to cause severe damage to the organism if unheeded. Acute pain serves to quickly remove the individual from the damaging environment. Acute pain by its very nature generally is short lasting and intense. Inflammatory pain on the other had may last for much longer periods of time and it's intensity is more graded. Inflammation may occur for many reasons including tissue damage, autoimmune response, and pathogen invasion. Inflammatory pain is mediated by an "inflammatory soup" that consists of substance P, histamines, acid, prostaglandin, bradykinin, CGRP, cytokines, ATP, and neurotransmitter release. The third class of pain is neuropathic and involves nerve damage that results in reorganization of neuronal proteins and circuits yielding a pathologic "sensitized" state that can produce chronic pain lasting for years. This type of pain provides no adaptive benefit and is particularly difficult to treat with existing therapies.

Pain, particularly neuropathic and intractable pain is a large unmet medical need. Millions of individuals suffer from severe pain that is not well controlled by current therapeutics. The current drugs used to treat pain include NSAIDS, COX2 inhibitors, opioids, tricyclic antidepressants, and anticonvulsants. Neuropathic pain has been particularly difficult to treat as it does not respond well to opiods until high doses are reached. Gabapentin is currently the favored therapeutic for the treatment of neuropathic pain although it works in only 60% of patients where it shows modest efficacy. The drug is however very safe and side effects are generally tolerable although sedation is an issue at higher doses.

Validation of Cav2.2 as a target for the treatment of neuropathic pain is provided by studies with ziconotide (also known as ω-conotoxin-MVIIA), a selective peptide blocker of this channel (Bowersox S S, Gadbois T, Singh T, Pettus M, Wang Y X, Luther R R. 1996. *J Pharmacol Exp Ther* 279: 1243-9; Jain K K. 2000. *Exp. Opin. Invest. Drugs* 9: 2403-10; Vanegas H, Schaible H.2000. *Pain* 85: 9-18) In man, intrathecal infusion of Ziconotide is effective for the treatment of intractable pain, cancer pain, opioid resistant pain, and neuropathic pain. The toxin has an 85% success rate for the treatment of pain in humans with a greater potency than morphine. An orally available antagonist of $Ca_v2.2$ should have similar efficacy without the need for intrathecal infusion. $Ca_v2.1$ and $Ca_v2.3$ are also in neurons of nociceptive pathways and antagonists of these channels could be used to treat pain.

Antagonists of $Ca_v2.1$, $Ca_v2.2$ or $Ca_v2.3$ should also be useful for treating other pathologies of the central nervous system that apparently involve excessive calcium entry. Cerebral ischaemia and stroke are associated with excessive calcium entry due to depolarization of neurons. The $Ca_v2.2$ antagonist ziconotide is effective in reducing infarct size in a focal ischemia model using laboratory animals, suggesting that $Ca_v2.2$ antagonists could be used for the treatment of stroke. Likewise, reducing excessive calcium influx into neurons may be useful for the treatment of epilepsy, traumatic brain injury, Alzheimer's disease, multi-infarct dementia and other classes of dementia, amyotrophic lateral sclerosis, amnesia, or neuronal damage caused by poison or other toxic substances.

$Ca_v2.2$ also mediates release of neurotransmitters from neurons of the sympathetic nervous system and antagonists could be used to treat cardiovascular diseases such as hypertension, cardiac arrhythmia, angina pectoris, myocardial infarction, and congestive heart failure.

Unfortunately, as described above, the efficacy of currently used sodium channel blockers and calcium channel blockers for the disease states described above has been to a large extent limited by a number of side effects. These side effects include various CNS disturbances such as blurred vision, dizziness, nausea, and sedation as well more potentially life threatening cardiac arrhythmias and cardiac failure. Accordingly, there remains a need to develop additional Na channel and Ca channel antagonists, preferably those with higher potency and fewer side effects. Unfortunately, as described above, the efficacy of currently used sodium channel blockers and calcium channel blockers for the disease states described above has been to a large extent limited by a number of side effects. These side effects include various CNS disturbances such as blurred vision, dizziness, nausea, and sedation as well more potentially life threatening cardiac arrhythmias and cardiac failure. Accordingly, there remains a need to develop additional Na channel and Ca channel antagonists, preferably those with higher potency and fewer side effects.

SUMMARY OF THE INVENTION

It has now been found that compounds of this invention, and pharmaceutically acceptable compositions thereof, are useful as inhibitors of voltage-gated sodium channels and calcium channels. These compounds have the general formula I:

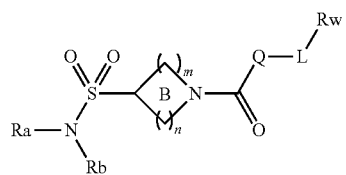

I or a pharmaceutical salt thereof, wherein the variables Ra, Rb, Q, Rw, m, and n, and Ring B are defined herein.

These compounds and pharmaceutically acceptable compositions are useful for treating or lessening the severity of a variety of diseases, disorders, or conditions, including, but not limited to, acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain.

DETAILED DESCRIPTION OF THE INVENTION

I. Definitions

For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed.: Smith, M. B. and March, J., John Wiley & Sons, New York: 2001, the entire contents of which are hereby incorporated by reference.

The term "modulating" as used herein means increasing or decreasing, e.g. activity, by a measurable amount. Compounds that modulate ion channel activity, such as calcium ion channel activity, by increasing the activity of the ion channel, e.g., a calcium ion channel, are called agonists. Compounds that modulate ion channel activity, such as calcium ion channel activity, by decreasing the activity of the ion channel, e.g., calcium ion channel, are called antagonists. An agonist interacts with an ion channel, such as calcium ion channel, to increase the ability of the receptor to transduce an intracellular signal in response to endogenous ligand binding. An antagonist interacts with an ion channel and competes with the endogenous ligand(s) or substrate(s) for binding site(s) on the receptor to decrease the ability of the receptor to transduce an intracellular signal in response to endogenous ligand binding.

The phrase "treating or reducing the severity of an ion channel mediated disease" refers both to treatments for diseases that are directly caused by ion channel activities and alleviation of symptoms of diseases not directly caused by ion channel activities. Examples of diseases whose symptoms may be affected by ion channel activities include, but are not limited to, acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain.

As used herein the term aliphatic encompasses the terms alkyl, alkenyl, alkynyl.

As used herein, an "alkyl" group refers to a saturated aliphatic hydrocarbon group containing 1-8 (e.g., 1-6 or 1-4) carbon atoms. An alkyl group can be straight or branched. Examples of an alkyl group include, but are not limited to, methyl, ethyl, propyl, isopropyl, butyl, isobutyl, sec-butyl, tert-butyl, n-pentyl, n-heptyl, and 2-ethylhexyl. An alkyl group can be optionally substituted with one or more substituents such as cycloalkyl, heterocycloalkyl, aryl, heteroaryl, alkoxy (two alkoxy groups on the same atom or adjacent atoms may form a ring together with the atom(s) to which they are bound), aroyl, heteroaroyl, alkoxycarbonyl, alkylcarbonyloxy, acyl, sulfonyl (such as alkylsulfonyl or arylsulfonyl), sulfinyl (such as alkylsulfinyl), sulfanyl (such as alkylsulfanyl), sulfoxy, urea, thiourea, sulfamoyl, sulfamide, oxo, carbamoyl, cycloalkyloxy, heterocycloalkyloxy, aryloxy, heteroaryloxy, aralkyloxy, heteroarylalkoxy, amino, nitro, carboxy, cyano, oxo, halo, hydroxy, sulfo, mercapto, alkylsulfanyl, alkylsulfinyl, alkylsulfonyl, aminocarbonyl, alkylcarbonylamino, cycloalkylcarbonylamino, cycloalkylalkylcarbonylamino, arylcarbonylamino, aralkylcarbonylamino, heterocycloalkyl-carbonylamino, heterocycloalkylalkylcarbonylamino, heteroarylcarbonylamino, or heteroaralkylcarbonylamino.

As used herein, an "alkenyl" group refers to an aliphatic carbon group that contains 2-8 (e.g., 2-6 or 2-4) carbon atoms and at least one double bond. Like an alkyl group, an alkenyl group can be straight or branched. Examples of an alkenyl group include, but are not limited to, allyl, isoprenyl, 2-butenyl, and 2-hexenyl. An alkenyl group can be optionally substituted with one or more substituents such as cycloalkyl, heterocycloalkyl, aryl, heteroaryl, alkoxy (two alkoxy groups on the same atom or adjacent atoms may form a ring together with the atom(s) to which they are bound), aroyl, heteroaroyl, alkoxycarbonyl, alkylcarbonyloxy, acyl, sulfonyl (such as alkylsulfonyl or arylsulfonyl), sulfinyl (such as alkylsulfinyl), sulfanyl (such as alkylsulfanyl), sulfoxy, urea, thiourea, sulfamoyl, sulfamide, oxo, carbamoyl, cycloalkyloxy, heterocycloalkyloxy, aryloxy, heteroaryloxy, aralkyloxy, heteroaralkoxy, amino, nitro, carboxy, cyano, oxo, halo, hydroxy, sulfo, mercapto, alkylsulfanyl, alkylsulfinyl, aminocarbonyl, alkylcarbonylamino, cycloalkylcarbonylamino, cycloalkylalkylcarbonylamino, arylcarbonylamino, aralkylcarbonylamino, heterocycloalkyl-carbonylamino, heterocycloalkylalkylcarbonylamino, heteroarylcarbonylamino, or heteroaralkylcarbonylamino.

As used herein, an "alkynyl" group refers to an aliphatic carbon group that contains 2-8 (e.g., 2-6 or 2-4) carbon atoms and has at least one triple bond. An alkynyl group can be straight or branched. Examples of an alkynyl group include, but are not limited to, propargyl and butynyl. An alkynyl group can be optionally substituted with one or more substituents such as cycloalkyl, heterocycloalkyl, aryl, heteroaryl, alkoxy (two alkoxy groups on the same atom or adjacent atoms may form a ring together with the atom(s) to which they are bound), aroyl, heteroaroyl, alkoxycarbonyl, alkylcarbonyloxy, acyl, sulfonyl (such as alkylsulfonyl or arylsulfonyl), sulfinyl (such as alkylsulfinyl), sulfanyl (such as alkylsulfanyl), sulfoxy, urea, thiourea, sulfamoyl, sulfamide, oxo, carbamoyl, cycloalkyloxy, heterocycloalkyloxy, aryloxy, heteroaryloxy, aralkyloxy, heteroarylalkoxy, amino, nitro, carboxy, cyano, oxo, halo, hydroxy, sulfo, mercapto, alkylsulfanyl, alkylsulfinyl, alkylsulfonyl, aminocarbonyl, alkylcarbonylamino, cycloalkylcarbonylamino, cycloalkylalkylcarbonylamino, arylcarbonylamino, aralkylcarbonylamino, heterocycloalkyl-carbonylamino, heterocycloalkylalkylcarbonylamino, heteroarylcarbonylamino, or heteroaralkylcarbonylamino.

As used herein, an "amino" group refers to —NR$^X$R$^Y$ wherein each of R$^X$ and R$^Y$ is independently hydrogen, alkyl, cycloalkyl, (cycloalkyl)alkyl, aryl, aralkyl, heterocycloalkyl, (heterocycloalkyl)alkyl, heteroaryl, or heteroaralkyl each of which are defined herein and are optionally substituted. When the term "amino" is not the terminal group (e.g., alkylcarbonylamino), it is represented by —NR$^X$—. R$^X$ has the same meaning as defined above.

As used herein, an "aryl" group used alone or as part of a larger moiety as in "aralkyl", "aralkoxy", or "aryloxyalkyl" refers to phenyl, naphthyl, or a benzofused group having 2 to 3 rings. For example, a benzofused group includes phenyl fused with one or two C$_{4-8}$ carbocyclic moieties, e.g., 1,2,3,4-tetrahydronaphthyl, indanyl, or fluorenyl. An aryl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, amino, nitro, carboxy, alkoxycarbonyl, alkylcarbonyloxy, aminocarbonyl, alkylcarbonylamino, cycloalkylcarbonylamino, (cycloalkyl)alkylcarbonylamino, arylcarbonylamino, aralkylcarbonylamino, (heterocycloalkyl)carbonylamino, (heterocycloalkyl)alkylcarbonylamino, heteroarylcarbonylamino, heteroaralkylcarbonylamino, cyano, halo, hydroxy, acyl, mercapto, sulfonyl (such as alkylsulfonyl), sulfinyl (such as alkylsulfinyl), sulfanyl (such as alkylsulfanyl), sulfoxy, urea, thiourea, sulfamoyl, sulfamide, oxo, or carbamoyl.

As used herein, an "aralkyl" group refers to an alkyl group (e.g., a C$_{1-4}$ alkyl group) that is substituted with an aryl group. Both "alkyl" and "aryl" are defined herein. An example of an aralkyl group is benzyl. A "heteroaralkyl" group refers to an alkyl group that is substituted with a heteroaryl. Both "alkyl" and "heteroaryl" are defined herein.

As used herein, a "cycicoaliphatic" group encompasses a "cycloalkyl" group and a "cycloalkenyl" group.

As used herein, a "cycloalkyl" group refers to a saturated carbocyclic mono- or bicyclic (fused or bridged) ring of 3-10 (e.g., 5-10) carbon atoms. Examples of cycloalkyl groups include cyclopropyl, cyclopentyl, cyclohexyl, cycloheptyl, adamantyl, norbornyl, cubyl, octahydro-indenyl, decahydro-naphthyl, bicyclo[3.2.1]octyl, bicyclo[2.2.2]octyl, bicyclo[3.3.1]nonyl, and bicyclo[3.3.2.]decyl, and adamantyl. A "cycloalkenyl" group, as used herein, refers to a non-aromatic carbocyclic ring of 3-10 (e.g., 4-8) carbon atoms having one or more double bond. Examples of cycloalkenyl groups include cyclopentenyl, 1,4-cyclohexa-di-enyl, cycloheptenyl, cyclooctenyl, hexahydro-indenyl, octahydro-naphthyl, bicyclo[2.2.2]octenyl, and bicyclo[3.3.1]nonenyl. A cycloalkyl or cycloalkenyl group can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, amino, nitro, carboxy, alkoxycarbonyl, alkylcarbonyloxy, aminocarbonyl, alkylcarbonylamino, cycloalkylcarbonylamino, (cycloalkyl)alkylcarbonylamino, arylcarbonylamino, aralkylcarbonylamino, (heterocycloalkyl)carbonylamino, (heterocycloalkyl)alkylcarbonylamino, heteroarylcarbonylamino, heteroaralkylcarbonylamino, cyano, halo, hydroxy, acyl, mercapto, sulfonyl (such as alkylsulfonyl or arylsulfonyl), sulfinyl (such as alkylsulfinyl), sulfanyl (such as alkylsulfanyl), sulfoxy, urea, thiourea, sulfamoyl, sulfamide, oxo, or carbamoyl.

As used herein, the term heterocycloaliphatic encompasses a heterocycloalkyl group and a heterocycloalkenyl group.

As used herein, a "heterocycloalkyl" group refers to a 3- to 10-membered mono- or bicylic (fused or bridged) (e.g., 5- to 10-membered mono- or bicyclic) saturated ring structure, in which one or more of the ring atoms is a heteroatom, e.g., N, O, or S. Examples of a heterocycloalkyl group include piperidinyl, piperazinyl, tetrahydropyranyl, tetrahydrofuryl, dioxolanyl, oxazolidinyl, isooxazolidinyl, morpholinyl, octahydro-benzofuryl, octahydro-chromenyl, octahydro-thiochromenyl, octahydro-indolyl, octahydro-pyrindinyl, decahydro-quinolinyl, octahydro-benzo[b]thiophenyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.0$^{3,7}$]nonyl. A monocyclic heterocycloalkyl group may be fused with a phenyl moiety such as tetrahydroisoquinoline. A "heterocycloalkenyl" group, as used herein, refers to a mono- or bicylic (e.g., 5- to 10-membered mono- or bicyclic) non-aromatic ring structure having one or more double bonds, and wherein one or more of the ring atoms is a heteroatom, e.g., N, O, or S. A heterocycloalkyl or heterocycloalkenyl group can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl (such as a benzimidazolidinyl), (heterocycloalkyl)alkyl, aryl, heteroaryl, alkoxy (two alkoxy groups on the same atom or adjacent atoms may form a ring together with the atom(s) to which they are bound), cycloalkyloxy, heterocycloalkyloxy, aryloxy, heteroaryloxy, aralkyloxy, heteroaralkyloxy, aroyl, heteroaroyl, amino, nitro, carboxy, alkoxycarbonyl, alkylcarbonyloxy, aminocarbonyl, alkylcarbonylamino, cycloalkylcarbonylamino, (cycloalkyl)alkylcarbonylamino, arylcarbonylamino, aralkylcarbonylamino, (heterocycloalkyl)carbonylamino, (heterocycloalkyl)alkylcarbonylamino, heteroarylcarbonylamino, heteroaralkylcarbonylamino, cyano, halo, hydroxy, acyl, mercapto, sulfonyl (such as alkylsulfonyl or arylsulfonyl), sulfinyl (such as alkylsulfinyl), sulfanyl (such as alkylsulfanyl), sulfoxy, urea, thiourea, sulfamoyl, sulfamide, oxo, or carbamoyl.

A "heteroaryl" group, as used herein, refers to a monocyclic, bicyclic, or tricyclic ring structure having 4 to 15 ring atoms wherein one or more of the ring atoms is a heteroatom, e.g., N, O, or S and wherein one or more rings of the bicyclic or tricyclic ring structure is aromatic. A heteroaryl group includes a benzofused ring system having 2 to 3 rings. For example, a benzofused group includes phenyl fused with one or two $C_{4-8}$ heterocyclic moieties, e.g., indolinyl and tertahydroquinolinyl. Some examples of heteroaryl are azetidinyl, pyridyl, furyl, pyrrolyl, thienyl, thiazolyl, oxazolyl, imidazolyl, indolyl, tetrazolyl, benzofuryl, isoquinolinyl, benzthiazolyl, xanthene, thioxanthene, phenothiazine, dihydroindole, and benzo[1,3]dioxole. A heteroaryl is optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, aryl, heteroaryl, alkoxy, cycloalkyloxy, heterocycloalkyloxy, aryloxy, heteroaryloxy, aralkyloxy, heteroaralkyloxy, aroyl, heteroaroyl, amino, nitro, carboxy, alkoxycarbonyl, alkylcarbonyloxy, aminocarbonyl, alkylcarbonylamino, cycloalkylcarbonylamino, (cycloalkyl)alkylcarbonylamino, arylcarbonylamino, aralkylcarbonylamino, (heterocycloalkyl)carbonylamino, (heterocycloalkyl)alkylcarbonylamino, heteroarylcarbonylamino, heteroaralkylcarbonylamino, cyano, halo, hydroxy, acyl, mercapto, sulfonyl (such as alkylsulfonyl or arylsulfonyl), sulfinyl (such as alkylsulfinyl), sulfanyl (such as alkylsulfanyl), sulfoxy, urea, thiourea, sulfamoyl, sulfamide, oxo, or carbamoyl. A "heteroaralkyl" group, as used herein, refers to an alkyl group (e.g., a $C_{1-4}$ alkyl group) that is substituted with a heteroaryl group. Both "alkyl" and "heteroaryl" have been defined above.

As used herein, "cyclic group" includes mono-, bi-, and tri-cyclic structures including cycloaliphatic, heterocycloaliphatic, aryl, or heteroaryl.

As used herein, an "acyl" group refers to a formyl group or alkyl-C(=O)— where "alkyl" has been defined previously. Acetyl and pivaloyl are examples of acyl groups.

As used herein, a "carbamoyl" group refers to a group having the structure —O—CO—NR$^X$R$^Y$ or —NR$^X$—CO—O—R$^Z$ wherein R$^X$ and R$^Y$ have been defined above and R$^z$ can be alkyl, aryl, aralkyl, heterocycloalkyl, heteroaryl, or heteroaralkyl.

As used herein, a "carboxy" and a "sulfo" group refer to —COOH or —COOR$^X$ and —SO$_3$H or —SO$_3$R$^X$, respectively.

As used herein, an "alkoxy" group refers to an alkyl-O— group where "alkyl" has been defined previously.

As used herein, a "sulfoxy" group refers to —O—SO—R$^X$ or —SO—O—R$^X$, where R$^X$ has been defined above.

As used herein, a "sulfonyl" group refers to —S(O)$_2$—R$^X$, wherein R$^X$ has been defined above.

As used herein a "sulfinyl" group refers to —S(O)—R$^X$, wherein R$^X$ has been defined above.

As used herein a "sulfanyl" group refers to —S—R$^X$, wherein R$^X$ has been defined above.

As used herein, a "halogen" or "halo" group refers to fluorine, chlorine, bromine or iodine.

As used herein, a "haloaliphatic" group refers to an aliphatic group substituted with 1-3 halogen. For instance, the term haloalkyl includes the group —CF$_3$.

As used herein, a "sulfamoyl" group refers to the structure —S(O)$_2$—NR$^X$R$^Y$ or —NR$^X$—S(O)$_2$—R$^Z$ wherein R$^X$, R$^Y$, and R$^Z$ have been defined above.

As used herein, a "sulfamide" group refers to the structure —NR$^X$—S(O)$_2$—NR$^Y$R$^Z$ wherein R$^X$, R$^Y$, and R$^Z$ have been defined above.

As used herein, a "carbonylamino" group used alone or in connection with another group refers to an amido group such as —C(O)—NR$^X$—, —NR$^X$—C(O)—, and —C(O)—N(R$^X$)$_2$. For instance an alkylcarbonylamino includes alkyl-C(O)—NR$^X$— and alkyl-NR$^X$—C(O)—.

As used herein, a "urea" group refers to the structure —NR$^X$—CO—NR$^Y$R$^Z$ and a "thiourea" group refers to the structure —NR$^X$—CS—NR$^Y$R$^Z$. R$^X$, R$^Y$, and R$^Z$ have been defined above.

The phrase "optionally substituted" is used interchangeably with the phrase "substituted or unsubstituted." As described herein, compounds of the invention may optionally be substituted with one or more substituents, such as are illustrated generally above, or as exemplified by particular classes, subclasses, and species of the invention. As described herein, the variables Ra, Rb, Rw, Q, L, Rp, and $L_{II}$ in formulae I and II encompass specific groups, such as alkyl and aryl. Unless otherwise noted, each of the specific groups for the variables Ra, Rb, Rw, Q, L, Rp, and $L_{II}$ may be optionally substituted with one or more substituents described herein. Each substituent of a specific group is further optionally substituted with one to three of halo, cyano, alkoxy, hydroxyl, nitro, haloalkyl, and alkyl. For instance, an alkyl group may be substituted with alkylsulfanyl and the alkylsulfanyl may be optionally substituted with one to three of halo, cyano, alkoxy, hydroxyl, nitro, haloalkyl, and alkyl. As an additional example, the cycloalkyl portion of a (cycloalkyl)carbonylamino may be optionally substituted with one to three of halo, cyano, alkoxy, hydroxyl, nitro, haloalkyl, and alkyl.

In general, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group may have a substituent at each substitutable position of the group, and when more than one position in any given structure may be substituted with more than one substituent selected from a specified group, the substituent may be either the same or different at every position. A ring substituent, such as a heterocycloalkyl, may be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

The phrase "stable or chemically feasible," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, an effective amount is defined as the amount required to confer a therapeutic effect on the treated patient, and is typically determined based on age, surface area, weight, and condition of the patient. The interrelationship of dosages for animals and humans (based on milligrams per meter squared of body surface) is described by Freireich et al., *Cancer Chemother. Rep.*, 50: 219 (1966). Body surface area may be approximately determined from height and weight of the patient. See, e.g., Scientific Tables, Geigy Pharmaceuticals, Ardsley, N.Y., 537 (1970). As used herein, "patient" refers to a mammal, including a human.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

II. Compounds

The present invention provides compounds that are useful as inhibitors of voltage-gated sodium channels and calcium channels.

A. Generic Embodiments

In one embodiment, the inhibitors of voltage-gated sodium channels and calcium channels have the structure of formula I:

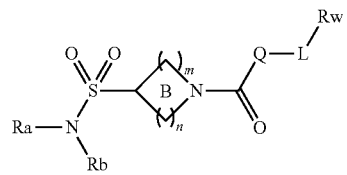

or a pharmaceutically acceptable salt thereof,
wherein:
Ring B is optionally substituted with 1-2 of halo, cyano, nitro, haloalkyl, alkoxy, sulfonyl, sulfinyl, sulfanyl, amino, carboxy, or an optionally substituted alipathic;
Each Ra is independently H, an optionally substituted aliphatic, an optionally substituted aryl, an optionally substituted heteroaryl, an optionally substituted aralkyl, an optionally substituted heteroaralkyl, an optionally substituted cycloaliphatic, or an optionally substituted heterocycloaliphatic;
Each Rb is independently H, an optionally substituted aliphatic, an optionally substituted aryl, an optionally substituted heteroaryl, an optionally substituted aralkyl, an optionally substituted heteroaralkyl, an optionally substituted cycloaliphatic, or an optionally substituted heterocycloaliphatic, or
Ra and Rb together with the nitrogen atom to which they are bound form an optionally substituted heterocycloaliphatic ring, in which the heteroaliphatic ring includes 0-2 additional heteroatoms selected from O, S, and N;
Each Q is an optionally substituted branched or unbranched $C_1$-$C_4$-alkyl;
Each L is absent, —O—, —NRc-, or —S—;
Each Rc is H, optionally substituted aliphatic, optionally substituted aryl, optionally substituted aralkyl, —C(O)—Ra, or —C(O)—ORa;
Each Rw is an optionally substituted aryl, an optionally substituted heteroaryl, or an optionally substituted heterocycloaliphatic;
Each n is 1, 2, or 3; and
Each m is 1, 2, or 3, provided that the sum of n and m is 2, 3, 4, 5, or 6.

In another embodiment, the inhibitors of voltage-gated sodium channels and calcium channels have the structure of formula II:

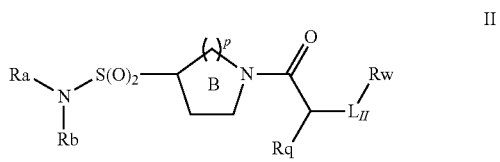

or a pharmaceutically acceptable salt thereof,
wherein:
Ring B is optionally substituted with 1-2 of halo, cyano, nitro, haloalkyl, alkoxy, sulfonyl, sulfinyl, sulfanyl, amino, carboxy, or an optionally substituted aliphatic;
Each Ra is independently H, an optionally substituted aliphatic, an optionally substituted aryl, an optionally substituted heteroaryl, an optionally substituted aralkyl, an optionally substituted heteroaralkyl, an optionally substituted cycloaliphatic, or an optionally substituted heterocycloaliphatic;
Each Rb is independently H, an optionally substituted aliphatic, an optionally substituted aryl, an optionally substituted heteroaryl, an optionally substituted aralkyl, an optionally substituted heteroaralkyl, an optionally substituted cycloaliphatic, or an optionally substituted heterocycloaliphatic, or
Ra and Rb together with the nitrogen atom to which they are bound form an optionally substituted heterocycloaliphatic ring, in which the heteroaliphatic ring includes 0-2 additional heteroatoms selected from O, S, and N;
Each Rq is H or an optionally substituted aliphatic;
Each $L_{II}$ is absent, —$CH_2$—, —O—, —NRc—, or —S—;
Each Rc is H, optionally substituted aliphatic, optionally substituted aryl, optionally substituted aralkyl, —C(O)—Ra, or —C(O)—ORa;

Each Rw is an optionally substituted aryl, an optionally substituted heteroaryl, or an optionally substituted heterocycloaliphatic; and Each p is 1 or 2.

B. Specific Embodiments i. Substituents Ra and Rb

Each Ra and Rb is the same. Each Ra and Rb is different. Each Ra and Rb is H. Ra is H and Rb is not H.

Each Ra is an optionally substituted aliphatic, e.g., an optionally substituted alkyl, an optionally substituted alkenyl, or an optionally substituted alkynyl. Each Ra is an optionally substituted alkyl, e.g., an optionally substituted methyl, an optionally substituted ethyl, an optionally substituted propyl, an optionally substituted butyl. Each Ra is an unsubstituted alkyl, e.g., methyl, ethyl, propyl, butyl. Each Rb is an optionally substituted aliphatic, e.g., an optionally substituted alkyl, an optionally substituted alkenyl, or an optionally substituted alkynyl. Each Rb is an optionally substituted alkyl, e.g., an optionally substituted methyl, an optionally substituted ethyl, an optionally substituted propyl, an optionally substituted butyl. Each Rb is independently an unsubstituted alkyl, e.g., methyl, ethyl, propyl, butyl. Each Ra is methyl. Each Rb is methyl. Ra and Rb are both an unsubstituted alkyl, e.g., methyl, ethyl, propyl, butyl. Ra and Rb are both methyl.

Each Ra is an optionally substituted aryl, such as mono- or bi-carbocyclic aromatic group. Each Ra is an optionally substituted mono-carbocyclic aromatic ("monocyclic aryl") group, e.g., an optionally substituted phenyl. Each Ra is a mono-carbocyclic aromatic group, e.g., phenyl. Each Ra is an optionally substituted bi-carbocyclic aromatic group, e.g., naphthyl, indenyl, or azulenyl. Each Ra is a bi-carbocyclic aromatic ("bicyclic aryl") group, e.g., naphthyl, indenyl, or azulenyl. Each Rb is an optionally substituted aryl, such as mono- or bi-carbocyclic aromatic group. Each Rb is an optionally substituted mono-carbocyclic aromatic ("monocyclic aryl") group, e.g., an optionally substituted phenyl. Each Rb is a mono-carbocyclic aromatic group, e.g., phenyl. Each Rb is an optionally substituted bi-carbocyclic aromatic ("bicyclic aryl") group, e.g., naphthyl, indenyl, or azulenyl. Each Rb is a bi-carbocyclic aromatic group, e.g., naphthyl, indenyl, or azulenyl.

Each Ra is an optionally substituted heteroaryl, such as a mono- or bi-heterocyclic aromatic group. Each Ra is an optionally substituted mono-heterocyclic aromatic ("monocyclic heteroaryl") group, e.g., furanyl, pyrrolyl, oxazolyl, thiazolyl, imidazolyl, pyrazaloyl, isoxazolyl, isothiazolyl, triazolyl, pyridinyl, pyridazinyl, pyrimidinyl, and pyrazinyl, each of which are optionally substituted. Each Ra is an optionally substituted 5-membered mono-heterocyclic aromatic group, e.g., furanyl, pyrrolyl, oxazolyl, thiazolyl, imidazolyl, pyrazaloyl, isoxazolyl, isothiazolyl, and triazolyl, each of which is optionally substituted. Each Ra is an optionally substituted 6-membered mono-heterocyclic aromatic group, e.g., pyridinyl, pyridazinyl, pyrimidinyl, and pyrazinyl, each of which is optionally substituted. Each Rb is an optionally substituted heteroaryl, such as a mono- or bi-heterocyclic aromatic ("monocyclic heteroaryl") group. Each Rb is an optionally substituted mono-heterocyclic aromatic group, e.g., furanyl, pyrrolyl, oxazolyl, thiazolyl, imidazolyl, pyrazaloyl, isoxazolyl, isothiazolyl, triazolyl, pyridinyl, pyridazinyl, pyrimidinyl, and pyrazinyl, each of which are optionally substituted. Each Rb is an optionally substituted 5-membered mono-heterocyclic aromatic group, e.g., furanyl, pyrrolyl, oxazolyl, thiazolyl, imidazolyl, pyrazaloyl, isoxazolyl, isothiazolyl, and triazolyl, each of which is optionally substituted. Each Rb is an optionally substituted 6-membered mono-heterocyclic aromatic group, e.g., pyridinyl, pyridazinyl, pyrimidinyl, and pyrazinyl, each of which is optionally substituted.

Each Ra is an optionally substituted bi-heterocyclic aromatic ("bicyclic heteroaryl") group, e.g., indolizinyl, indolyl, isoindolyl, benzofuranyl, benzothiopenyl, 1H-indazolyl, benzimidazolyl, benzthiazolyl, purinyl, 4H-quinolizinyl, quinolinyl, isoquinolinyl, cinnolinyl, phthalazinyl, quinazolinyl, quinoxalinyl, naphthyridinyl, and pteridinyl, each of which is optionally substituted. Each Ra is an optionally substituted 9-membered bi-heterocyclic aromatic group, e.g., indolizinyl, indolyl, isoindolyl, benzofuranyl, benzothiopenyl, 1H-indazolyl, benzimidazolyl, benzthiazolyl, and purinyl, each of which is optionally substituted. Each Ra is an optionally substituted 10-membered bi-heterocyclic aromatic group, e.g., 4H-quinolizinyl, quinolinyl, isoquinolinyl, cinnolinyl, phthalazinyl, quinazolinyl, quinoxalinyl, naphthyridinyl, and pteridinyl, each of which are optionally substituted. Each Rb is an optionally substituted bi-heterocyclic aromatic ("bicyclic heteroaryl") group, e.g., indolizinyl, indolyl, isoindolyl, benzofuranyl, benzothiopenyl, 1H-indazolyl, benzimidazolyl, benzthiazolyl, purinyl, 4H-quinolizinyl, quinolinyl, isoquinolinyl, cinnolinyl, phthalazinyl, quinazolinyl, quinoxalinyl, naphthyridinyl, and pteridinyl, each of which is optionally substituted. Each Rb is an optionally substituted 9-membered bi-heterocyclic aromatic group, e.g., indolizinyl, indolyl, isoindolyl, benzofuranyl, benzothiopenyl, 1H-indazolyl, benzimidazolyl, benzthiazolyl, and purinyl, each of which is optionally substituted. Each Rb is an optionally substituted 10-membered bi-heterocyclic aromatic group, e.g., 4H-quinolizinyl, quinolinyl, isoquinolinyl, cinnolinyl, phthalazinyl, quinazolinyl, quinoxalinyl, naphthyridinyl, and pteridinyl, each of which are optionally substituted.

Each Ra is an optionally substituted benzofused bicyclic aryl moiety covered under the term aryl, e.g., tetrahydronaphthalyl. Each Ra is an optionally substituted benzofused bicyclic herteroaryl moiety covered under the term heteroaryl, e.g., indolinyl and tetrahydroquinolinyl. Each Rb is an optionally substituted benzofused bicycle aryl moiety covered under the term aryl, e.g., tetrahydronaphthalyl. Each Rb is an optionally substituted benzofused bicyclic herteroaryl moiety covered under the term heteroaryl, e.g., indolinyl and tetrahydroquinolinyl.

Each Ra is an optionally substituted aralkyl, e.g., $(C_1-C_4)$-alkyl-aryl in which the alkyl and aryl are optionally substituted. Each Ra is an optionally substituted $(C_1-C_4)$-alkyl-monocyclic aryl, e.g., $(C_1-C_4)$-phenyl in which the alkyl and phenyl are optionally substituted. Each Ra is $(C_1-C_4)$-phenyl, e.g., benzyl. Each Ra is an optionally substituted $(C_1-C_4)$-alkyl-bicyclic aryl, e.g., $(C_1-C_4)$-naphthyl, $(C_1-C_4)$-indenyl, or $(C_1-C_4)$-azulenyl in which the alkyl and bicyclic aryl are optionally substituted. Each Ra is an optionally substituted $(C_1-C_4)$-alkyl-benzofused bicyclic aryl, e.g., $(C_1-C_4)$-alkyl-tetrahydronaphthalyl. Each Rb is an optionally substituted aralkyl, e.g., $(C_1-C_4)$-alkyl-aryl in which the alkyl and aryl are optionally substituted. Each Rb is an optionally substituted $(C_1-C_4)$-alkyl-monocyclic aryl, e.g., $(C_1-C_4)$-phenyl in which the alkyl and phenyl are optionally substituted. Each Rb is $(C_1-C_4)$-phenyl, e.g., benzyl. Each Rb is an optionally substituted $(C_1-C_4)$-alkyl-bicyclic aryl, e.g., $(C_1-C_4)$-naphthyl, $(C_1-C_4)$-indenyl, or $(C_1-C_4)$-azulenyl in which the alkyl and bicyclic aryl are optionally substituted. Each Rb is an optionally substituted $(C_1-C_4)$alkyl-benzofused bicyclic aryl, e.g., $(C_1-C_4)$-alkyl-tetrahydronaphthalyl.

Each Ra is an optionally substituted heteroaralkyl, e.g., $(C_1-C_4)$-alkyl-heteroaryl in which the alkyl and heteroaryl are optionally substituted. Each Ra is an optionally substituted $(C_1-C_4)$-alkyl-monocyclic heteroaryl, e.g., $(C_1-C_4)$-furanyl, $(C_1-C_4)$-pyrrolyl, $(C_1-C_4)$-oxazolyl, $(C_1-C_4)$-thiazolyl, $(C_1-C_4)$-imidazolyl, $(C_1-C_4)$-pyrazaloyl, $(C_1-C_4)$-isoxazolyl, $(C_1-C_4)$-isothiazolyl, $(C_1-C_4)$-triazolyl, $(C_1-C_4)$-pyridinyl, $(C_1-C_4)$-pyridazinyl, $(C_1-C_4)$-pyrimidinyl, and $(C_1-C_4)$-pyrazinyl in which the alkyl and the heteroaryl are optionally substituted. Each Ra is —$CH_2$-heteroaryl, e.g., —$CH_2$-furanyl, —$CH_2$-pyrrolyl, —$CH_2$-oxazolyl, —$CH_2$-thiazolyl, —$CH_2$-imidazolyl, —$CH_2$-pyrazaloyl, —$CH_2$-isoxazolyl, —$CH_2$-isothiazolyl, —$CH_2$-triazolyl, —$CH_2$-pyridinyl, —$CH_2$-pyridazinyl, —$CH_2$-pyrimidinyl, and —$CH_2$-pyrazinyl. Each Ra is an optionally substituted $(C_1-C_4)$alkyl-bicyclic heteroaryl, e.g., $(C_1-C_4)$-indolizinyl, $(C_1-C_4)$-indolyl, $(C_1-C_4)$-isoindolyl, $(C_1-C_4)$-benzofuranyl, $(C_1-C_4)$-benzothiopenyl, $(C_1-C_4)$-1H-indazolyl, $(C_1-C_4)$-benzimidazolyl, $(C_1-C_4)$-benzthiazolyl, $(C_1-C_4)$-purinyl, $(C_1-C_4)$-4H-quinolizinyl, $(C_1-C_4)$-quinolinyl, $(C_1-C_4)$-isoquinolinyl, $(C_1-C_4)$-cinnolinyl, $(C_1-C_4)$-phthalazinyl, $(C_1-C_4)$-quinazolinyl, $(C_1-C_4)$-quinoxalinyl, $(C_1-C_4)$-naphthyridinyl, and $(C_1-C_4)$-pteridinyl, in which the alkyl and bicyclic heteroaryl are optionally substituted. Each Ra is an optionally substituted $(C_1-C_4)$-benzofused bicyclic herteroaryl, e.g., $(C_1-C_4)$-indolinyl and $(C_1-C_4)$-tetrahydroquinolinyl.

Each Rb is an optionally substituted heteroaralkyl, e.g., $(C_1-C_4)$-alkyl-heteroaryl in which the alkyl and heteroaryl are optionally substituted. Each Ra is an optionally substituted $(C_1-C_4)$-alkyl-monocyclic heteroaryl, e.g., $(C_1-C_4)$-furanyl, $(C_1-C_4)$-pyrrolyl, $(C_1-C_4)$-oxazolyl, $(C_1-C_4)$-thiazolyl, $(C_1-C_4)$-imidazolyl, $(C_1-C_4)$-pyrazaloyl, $(C_1-C_4)$-isoxazolyl, $(C_1-C_4)$-isothiazolyl, $(C_1-C_4)$-triazolyl, $(C_1-C_4)$-pyridinyl, $(C_1-C_4)$-pyridazinyl, $(C_1-C_4)$-pyrimidinyl, and $(C_1-C_4)$-pyrazinyl in which the alkyl and the heteroaryl are optionally substituted. Each Rb is —$CH_2$-heteroaryl, e.g., —$CH_2$-furanyl, —$CH_2$-pyrrolyl, —$CH_2$-oxazolyl, —$CH_2$-thiazolyl, —$CH_2$-imidazolyl, —$CH_2$-pyrazaloyl, —$CH_2$-isoxazolyl, —$CH_2$-isothiazolyl, —$CH_2$-triazolyl, —$CH_2$-pyridinyl, —$CH_2$-pyridazinyl, —$CH_2$-pyrimidinyl, and —$CH_2$-pyrazinyl. Each Rb is an optionally substituted $(C_1-C_4)$alkyl-bicyclic heteroaryl, e.g., $(C_1-C_4)$-indolizinyl, $(C_1-C_4)$-indolyl, $(C_1-C_4)$-isoindolyl, $(C_1-C_4)$-benzofuranyl, $(C_1-C_4)$-benzothiopenyl, $(C_1-C_4)$-1H-indazolyl, $(C_1-C_4)$-benzimidazolyl, $(C_1-C_4)$-benzthiazolyl, $(C_1-C_4)$-purinyl, $(C_1-C_4)$-4H-quinolizinyl, $(C_1-C_4)$-quinolinyl, $(C_1-C_4)$-isoquinolinyl, $(C_1-C_4)$-cinnolinyl, $(C_1-C_4)$-phthalazinyl, $(C_1-C_4)$-quinazolinyl, $(C_1-C_4)$-quinoxalinyl, $(C_1-C_4)$-naphthyridinyl, and $(C_1-C_4)$-pteridinyl, in which the alkyl and bicyclic heteroaryl are optionally substituted. Each Rb is an optionally substituted $(C_1-C_4)$-benzofused bicyclic herteroaryl, e.g., $(C_1-C_4)$-indolinyl and $(C_1-C_4)$-tetrahydroquinolinyl.

Each Ra is an optionally substituted cycloaliphatic. Each Ra is an optionally substituted monocycloaliphatic, e.g., monocycloalkyl and monocycloalkenyl. Each Ra is an optionally substituted monocycloalkyl, e.g., cyclopentyl, cyclohexyl, and cycloheptyl, each of which is optionally substituted. Each Ra is an optionally substituted monocycloalkenyl, e.g., cyclopentenyl, cyclohexenyl, and cycloheptenyl, each of which is optionally substituted. Each Ra is an optionally substituted heterocycloaliphatic. Each Ra is an optionally substituted monocyclic heteroaliphatic, e.g., a monocyclic heteroalkyl or a monocyclic heteroalkenyl. Each Ra is an optionally substituted monocyclic heteroalkyl, e.g., pyrrolidinyl, dioxolanyl, imidazolidinyl, pyrazolidinyl, piperidinyl, dioxanyl, morpholinyl, dithianyl, thiomorpholinyl, and piperazinyl, each of which is optionally substituted. Each Ra is an optionally substituted monocyclic heteroalkenyl, e.g., pyrrolinyl, imidazolinyl, pyrazolinyl, and pyranyl, each of which is optionally substituted. Each Ra is an optionally substituted bicycloheteroaliphatic, e.g., a bicycloheteroalkyl or a bicycloheteroalkenyl. Each Ra is an optionally substituted bicycloheteroalkyl, e.g., decahydroquinolinyl or decahydroisoquinolinyl. Each Ra is an optionally substituted bicycloheteroalkenyl, e.g., tetrahydroindolyl and hexahydroquinolinyl, each of which are optionally substituted.

Each Rb is an optionally substituted cycloaliphatic. Each Rb is an optionally substituted monocycloaliphatic, e.g., monocycloalkyl and monocycloalkenyl. Each Rb is an optionally substituted monocycloalkyl, e.g., cyclopentyl, cyclohexyl, and cycloheptyl, each of which is optionally substituted. Each Rb is an optionally substituted monocycloalkenyl, e.g., cyclopentenyl, cyclohexenyl, and cycloheptenyl, each of which is optionally substituted. Each Rb is an optionally substituted heterocycloaliphatic. Each Rb is an optionally substituted monocyclic heteroaliphatic, e.g., a monocyclic heteroalkyl or a monocyclic heteroalkenyl. Each Rb is an optionally substituted monocyclic heteroalkyl, e.g., pyrrolidinyl, dioxolanyl, imidazolidinyl, pyrazolidinyl, piperidinyl, dioxanyl, morpholinyl, dithianyl, thiomorpholinyl, and piperazinyl, each of which is optionally substituted. Each Rb is an optionally substituted monocyclic heteroalkenyl, e.g., pyrrolinyl, imidazolinyl, pyrazolinyl, and pyranyl, each of which is optionally substituted. Each Rb is an optionally substituted bicycloheteroaliphatic, e.g., a bicycloheteroalkyl or a bicycloheteroalkenyl. Each Rb is an optionally substituted bicycloheteroalkyl, e.g., decahydroquinolinyl or decahydroisoquinolinyl. Each Rb is an optionally substituted bicycloheteroalkenyl, e.g., tertahydroindolyl, and hexahydroquinolinyl, each of which are optionally substituted.

The compounds of formulae I and II include any combination of the Ra and Rb substituents described above. The following combinations are presented as examples of different combinations substituents of Ra and Rb.

Ra is H and Rb is an optionally substituted aryl, such as mono- or bi-carbocyclic aromatic group. Ra is H and Rb is an optionally substituted mono-carbocyclic aromatic ("monocyclic aryl") group, e.g., an optionally substituted phenyl. Ra is H and Rb is an optionally substituted bicyclic aryl. Ra is H and Rb is an optionally substituted aliphatic, e.g., an optionally substituted alkyl, an optionally substituted alkenyl, or an optionally substituted alkynyl. Ra is H and Rb is an optionally substituted alkyl, e.g., an optionally substituted methyl, an optionally substituted ethyl, an optionally substituted propyl, an optionally substituted butyl. Ra is H and Rb is an unsubstituted alkyl, e.g., methyl, ethyl, propyl, butyl. Ra is H and Rb is methyl. Ra is H and Rb is an optionally substituted aralkyl, e.g., $(C_1-C_4)$alkyl-aryl in which the alkyl and aryl are optionally substituted. Ra is H and Rb is an optionally substituted $(C_1-C_4)$alkyl-monocyclic aryl, e.g., $(C_1-C_4)$-phenyl in which the alkyl and phenyl are optionally substituted. Ra is H and Rb is $(C_1-C_4)$-phenyl, e.g., benzyl.

Ra is H and Rb is an optionally substituted heteroaryl, such as mono- or bi-carbocyclic heteroaromatic group. Ra is H and Rb is an optionally substituted mono-carbocyclic heteroaromatic ("monocyclic aryl") group. Ra is H and Rb is an optionally substituted bicyclic heteroaryl. Ra is H and Rb is a benzofused bicyclic heteroaryl, e.g., an optionally substituted indolinyl.

In another aspect, Ra and Rb together with the nitrogen atom to which they are bound form an optionally substituted monocyclic or bicyclic heteroaliphatic ring. Ra and Rb together with the nitrogen atom to which they are bound form an optionally substituted monocyclic heteroaliphatic ring, e.g., a monocyclic heteroalkyl or a monocyclic heteroalkenyl ring, in which the heteroaliphatic ring includes 0-2 additional heteroatoms selected from O, S, and N. Ra and Rb together with the nitrogen atom to which they are bound form an optionally substituted heterocycloalkyl, e.g., a 5 membered or 6 membered heterocycloalkyl each of which is optionally substituted. Ra and Rb together with the nitrogen atom to which they are bound form an optionally substituted 5 membered heterocycloalkyl, e.g., pyrrolidinyl, imidazolidinyl, pyrazolidinyl, each of which is optionally substituted. Ra and Rb together with the nitrogen atom to which they are bound form an optionally substituted 6 membered heterocycloalkyl, e.g., piperidinyl, morpholinyl, thiomorpholinyl, and piperazinyl, each of which is optionally substituted. Ra and Rb together with the nitrogen atom to which they are bound form an optionally substituted 5 membered heterocycloalkenyl, e.g., pyrrolinyl, imidazolinyl, and pyrazolinyl, each of which is optionally substituted. Ra and Rb together with the nitrogen atom to which they are bound form an optionally substituted 6 membered heterocycloalkenyl, e.g., an optionally substituted tetrahydropyridinyl. Ra and Rb together with the nitrogen atom to which they are bound form an optionally substituted bicyclic heteroaliphatic ring, e.g., a bicyclic heteroalkyl or a bicyclic heteroalkenyl ring, in which the heteroaliphatic ring includes 0-2 additional heteroatoms selected from O, S, and N. Ra and Rb together form an optionally substituted bicyclic heteroalkenyl ring, e.g., tetrahydroindolinyl, and hexahydroquinolinyl, each of which is optionally substituted. Ra and Rb together form an optionally substituted a bicyclic heteroalkyl ring, e.g., an optionally substituted decahydroquinolinyl. Ra and Rb together with the nitrogen atom to which they are bound form an optionally substituted benzofused bicyclic herteroaryl, e.g., indolinyl and tetrahydroquinolinyl, each of which is optionally substituted.

ii. Rc Substituents

Each Rc is an optionally substituted aliphatic, e.g., an optionally substituted alkyl, an optionally substituted alkenyl, or an optionally substituted alkynyl. Each Ra is an optionally substituted alkyl, e.g., an optionally substituted methyl, an optionally substituted ethyl, an optionally substituted propyl, an optionally substituted butyl. Each Rc is an unsubstituted alkyl, e.g., methyl, ethyl, propyl, butyl.

Each Rc is an optionally substituted aryl, such as mono- or bi-carbocyclic aromatic group. Each Rc is an optionally substituted mono-carbocyclic aromatic ("monocyclic aryl") group, e.g., an optionally substituted phenyl. Each Rc is a mono-carbocyclic aromatic group, e.g., phenyl. Each Rc is an optionally substituted bi-carbocyclic aromatic group, e.g., naphthyl, indenyl, or azulenyl.

Each Rc is an optionally substituted aralkyl, e.g., ($C_1$-$C_4$) alkyl-aryl in which the alkyl and aryl are optionally substituted. Each Rc is an optionally substituted ($C_1$-$C_4$)alkyl-monocyclic aryl, e.g., ($C_1$-$C_4$)-phenyl in which the alkyl and phenyl are optionally substituted. Each Ra is ($C_1$-$C_4$)-phenyl, e.g., benzyl.

Each Rc is —C(O)—Ra wherein Ra is as has been previously described. Each Rc is optionally substituted alkanoyl. Each Rc is optionally substituted aroyl. Each Rc is acetyl, propionyl or butanoyl. Each Rc is optionally substituted benzoyl.

Each Rc is —C(O)—O—Ra wherein Ra is as has been previously described. Each Rc is optionally substituted alkyloxycarbonyl. Each Rc is optionally substituted benzyloxycarbonyl.

iii. Rw Substituents

Rw is an optionally substituted aryl, e.g., a monocarbocyclic aromatic ring or a bi-carbocyclic aromatic ring system, each of which is optionally substituted. Rw is an optionally substituted monocarbocyclic aromatic ring, e.g., an optionally substituted phenyl. Rw is a phenyl substituted with 1-3 of halo or haloaliphatic. Rw is phenyl. Rw is an optionally substituted bi-carbocyclic aromatic ring system, e.g., indenyl, naphthalenyl, and azulenyl, each optionally substituted. Rw is indenyl, naphthalenyl, and azulenyl each optionally substituted with 1-3 of halo, or haloaliphatic. Rw is an optionally substituted benzofused bicyclic aryl moiety covered under the term aryl, e.g., an optionally substituted tetrahydronaphthalyl.

Rw is an optionally substituted heteroaryl, e.g., a monocyclic heteroaryl ring or a bicyclic heteroaryl ring system, each of which is optionally substituted. Rw is an optionally substituted monocyclic heteroaryl ring, e.g., furanyl, thiophenyl, pyrrolyl, oxazolyl, thiazolyl, imidazolyl, pyrazolyl, and isoxazolyl, each of which is optionally substituted. Rw is furanyl, thiophene, pyrrolyl, oxazolyl, thiazolyl, imidazolyl, pyrazolyl, and isoxazolyl, each of which is optionally substituted with 1-3 of halo, or haloaliphatic. Rw is an optionally substituted bicyclic heteroaryl ring system, e.g., indolizinyl, indolyl, isoindolyl, benzofuranyl, benzothiophenyl, benzimidazolyl, quinolinyl, cinnolinyl, quinazolinyl, quinoxalinyl, and naphthyrindinyl, each of which is optionally substituted. Rw is indolizinyl, indolyl, isoindolyl, benzofuranyl, benzothiophenyl, benzimidazolyl, quinolinyl, cinnolinyl, quinazolinyl, quinoxalinyl, and naphthyrindinyl, each of which is optionally substituted with 1-3 of halo, or haloaliphatic. Rw is an optionally substituted quinolin-4-yl or an optionally substituted indolin-1-yl. Rw is quinolin-4-yl or indolin-1-yl each optionally substituted with 1-3 of halo, or haloaliphatic. Rw is an optionally substituted benzofused bicyclic herteroaryl moiety covered under the term heteroaryl, e.g., indolinyl and tetrahydroquinolinyl, each of which is optionally substituted.

Rw is an optionally substituted heterocycloaliphatic, e.g, a monocyclic or a bicyclic heteroaliphatic ring system, each optionally substituted. Rw is optionally substituted monocyclic heteroaliphatic ring, e.g., a monocyclic heteroalkyl or a monocyclic heteroalkenyl ring, each of which is optionally substituted. Rw is an optionally substituted heterocycloalkyl, e.g., a 5 membered or 6 membered heterocycloalkyl each of which is optionally substituted. Rw is an optionally substituted 5 membered heterocycloalkyl, e.g., pyrrolidinyl, imidazolidinyl, and pyrazolidinyl, each of which is optionally substituted. Rw is an optionally substituted 6 membered heterocycloalkyl, e.g., piperidinyl, morpholinyl, thiomorpholinyl, and piperazinyl, each of which is optionally substituted. Rw is an optionally substituted 5 membered heterocycloalkenyl, e.g., pyrrolinyl, imidazolinyl, and pyrazolinyl, each of which is optionally substituted. Rw is an optionally substituted 6 membered heterocycloalkenyl, e.g., an optionally substituted tetrahydropyridinyl. Rw is an optionally substituted bicyclic heteroaliphatic ring, e.g., a bicyclic heteroalkyl or a bicyclic heteroalkenyl ring, each of which is optionally substituted. Rw is an optionally substituted bicyclic heteroalkenyl ring, e.g., tetrahydroindolyl and hexahydroquinolinyl, each of which is optionally substituted. Rw is an optionally substituted bicyclic heteroalkenyl ring, e.g., an optionally substituted octahydroquinolinyl.

iv. Q, —CH(Rq), -L and -L$_{II}$

Q is an optionally substituted branched or unbranched C$_1$-C$_4$ alkyl. In several embodiments, Q is a substituted branched or unbraced alkyl. In other embodiments, Q is unsubstituted branched or unbranched alkyl. For example, Q is unsubstituted brached alkyl. Q is —CH(Rq), in which Rq is H or an optionally substituted aliphatic. Q is —CH(Rq), in which Rq is H or an optionally substituted alkyl. Q is —CH (Rq), in which Rq is H or alkyl. Q is —CH(Rq), in which Rq is H. Q is —CH(Rq), in which Rq is alkyl, e.g., methyl, ethyl, propyl, and butyl. Q is —CH(Rq), in which Rq is methyl.

L is absent, —O—, —NH—, or —S—. L$_{II}$ is absent, —CH$_2$—, —O—, —NH—, or —S—. L is absent. L is —O—. L is NH. L is —S—. L$_{II}$ is absent. L$_{II}$ is —CH$_2$—. L$_{II}$ is —O—. L$_{II}$ is NH. L$_{II}$ is —S—.

The compounds of formulae I and II include any combination of the -Q-L and —CH(Rq)-L$_{II}$ substituents described above. The following combinations are non-limited are presented as examples of different combinations substituents of Q, —CH(Rq), -L and -L$_{II}$.

-Q- is optionally substituted C$_1$-C$_4$ alkyl, e.g., methyl, ethyl, propyl, and butyl, and L is absent. -Q- is an optionally substituted ethyl and L is absent. -Q- is ethyl optionally substituted with aliphatic and L is absent. -Q- is —CH(Rq), in which Rq is H or aliphatic, and L is absent. -Q- is —CH(Rq), in which Rq is aliphatic, and L is absent. -Q- is —CH(Rq), in which Rq is alkyl, and L is absent. -Q- is —CH(Rq), in which Rq is methyl, and L is absent.

-Q- is optionally substituted C$_1$-C$_4$ alkyl, e.g., methyl, ethyl, propyl, and butyl, and L is —O—. -Q- is —CH(Rq), in which Rq is H or aliphatic, and L is —O—. -Q- is —CH(Rq), in which Rq is aliphatic, and L is —O—. -Q- is —CH(Rq), in which Rq is H, and L is —O—. -Q- is optionally substituted C$_1$-C$_4$ alkyl, e.g., methyl, ethyl, propyl, and butyl, and L is —NH—. -Q- is —CH(Rq), in which Rq is H or aliphatic, and L is —NH—. -Q- is —CH(Rq), in which Rq is H, and L is —NH—. -Q- is optionally substituted C$_1$-C$_4$ alkyl, e.g., methyl, ethyl, propyl, and butyl, and L is —S—. -Q- is —CH (Rq), in which Rq is H or aliphatic, and L is —S—. -Q- is —CH(Rq), in which Rq is H, and L is —S—.

v. Ring B and Variables n, m, and p n is 1, 2, or 3. m is 1, 2, or 3, provided that the sum of n and m is 2, 3, 4, 5, or 6. n is 1 and m is 1. n is 1 and m is 2. n is 1 and m is 3. n is 2 and m is 2. n is 2 and m is 3. p is 1. p is 2.

Ring B is a pyrrolidinyl optionally substituted with 1-2 of halo, cyano, nitro, haloalkyl, alkoxy, sulfonyl, sulfinyl, sulfanyl, amino, carboxy, or an optionally substituted alipathic. Ring B is a piperidinyl optionally substituted with 1-2 of halo, cyano, nitro, haloalkyl, alkoxy, sulfonyl, sulfinyl, sulfanyl, amino, carboxy, or an optionally substituted alipathic. Ring B is substituted with 1-2 of halo, cyano, nitro, haloalkyl, alkoxy, sulfonyl, sulfinyl, sulfanyl, amino, carboxy, or an optionally substituted alipathic. Ring B is substituted with 1-2 of halo, cyano, nitro, haloalkyl, alkoxy, or an optionally substituted aliphatic. Ring B is substituted with 1-2 of sulfonyl, sulfinyl, sulfanyl, amino, carboxy, or an optionally substituted alipathic. Ring B is substituted with amino or carboxy. Ring B is substituted with 1-2 halo, haloalkyl, or alkoxy.

C. Specific Compounds of Formulae I and II

Specific inhibitors of voltage-gated sodium channels and calcium channels are listed in Table 1 below.

TABLE 1

Exemplary compounds of Formulae I and II

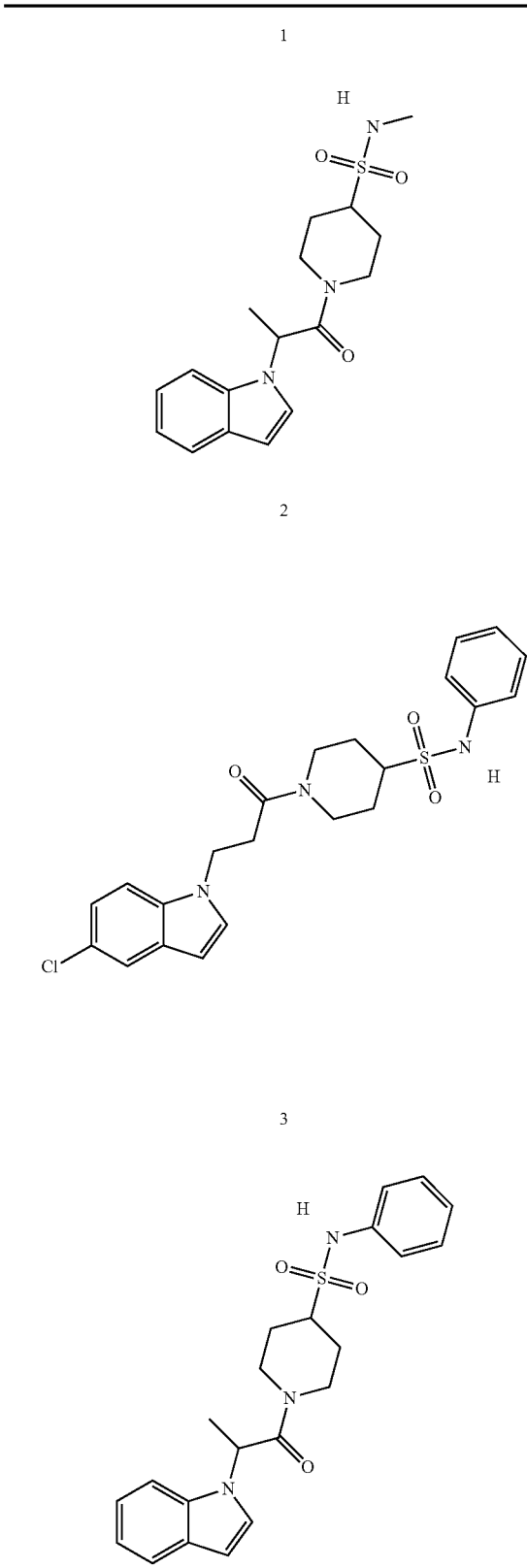

TABLE 1-continued
Exemplary compounds of Formulae I and II
4
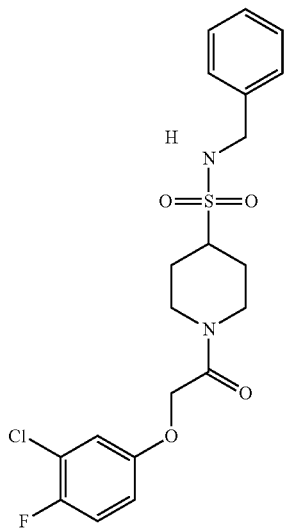
5
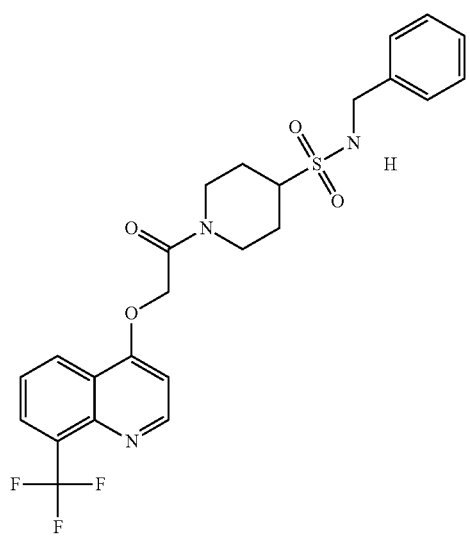
TABLE 1-continued
Exemplary compounds of Formulae I and II
6
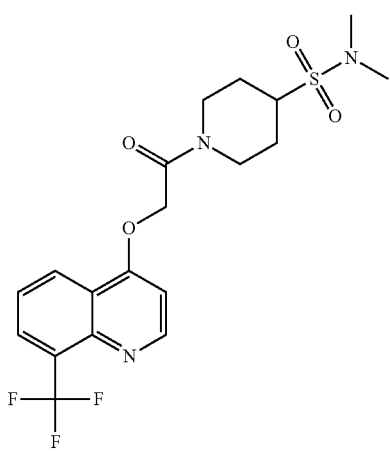
7
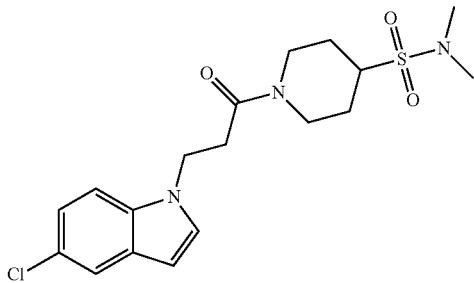
8
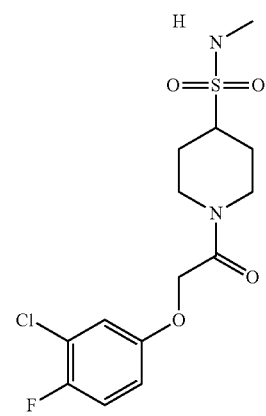

TABLE 1-continued
Exemplary compounds of Formulae I and II
9
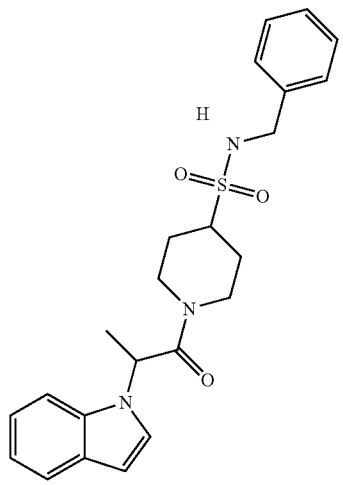
10
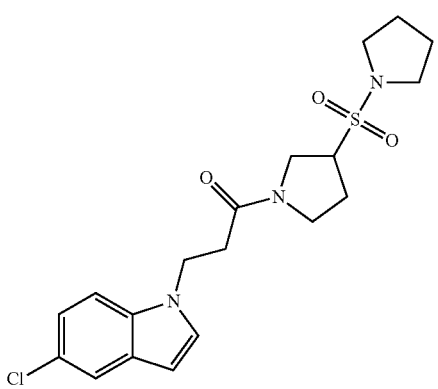
11
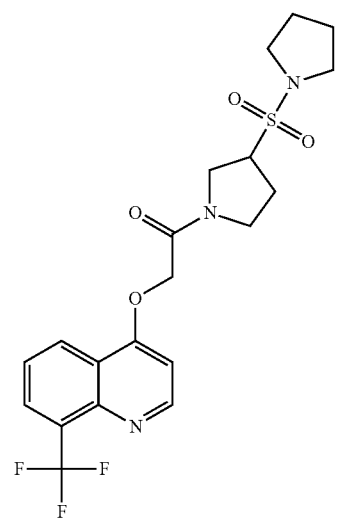
TABLE 1-continued
Exemplary compounds of Formulae I and II
12
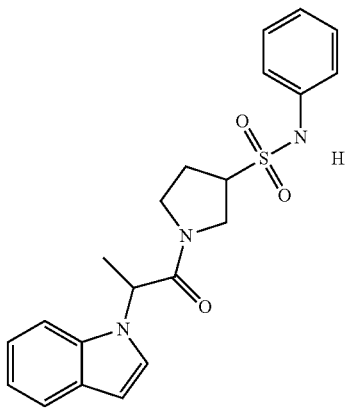
13
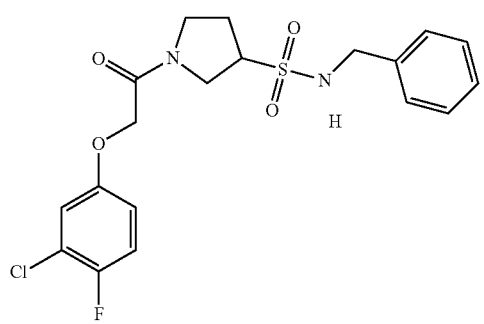
14
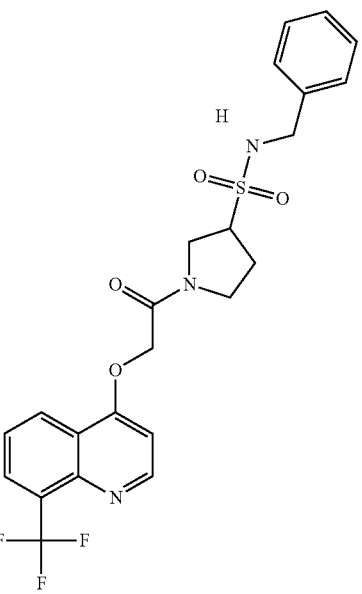

TABLE 1-continued
Exemplary compounds of Formulae I and II
15
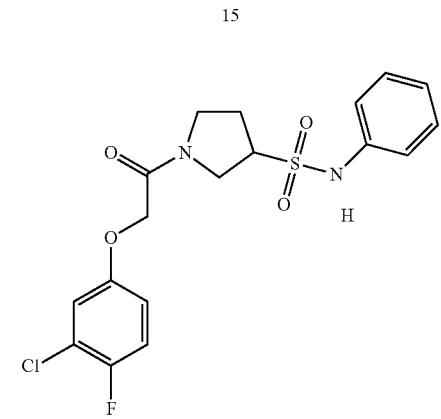
16
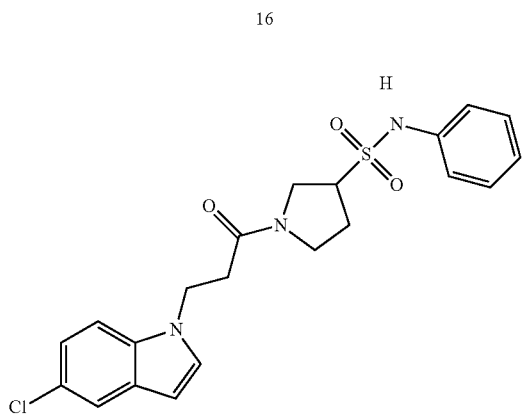
17
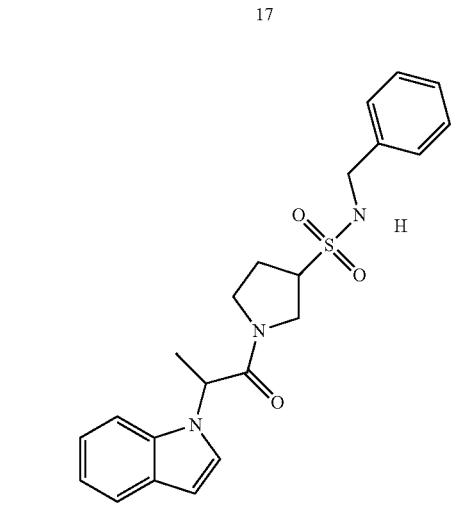
TABLE 1-continued
Exemplary compounds of Formulae I and II
18
19
20
21
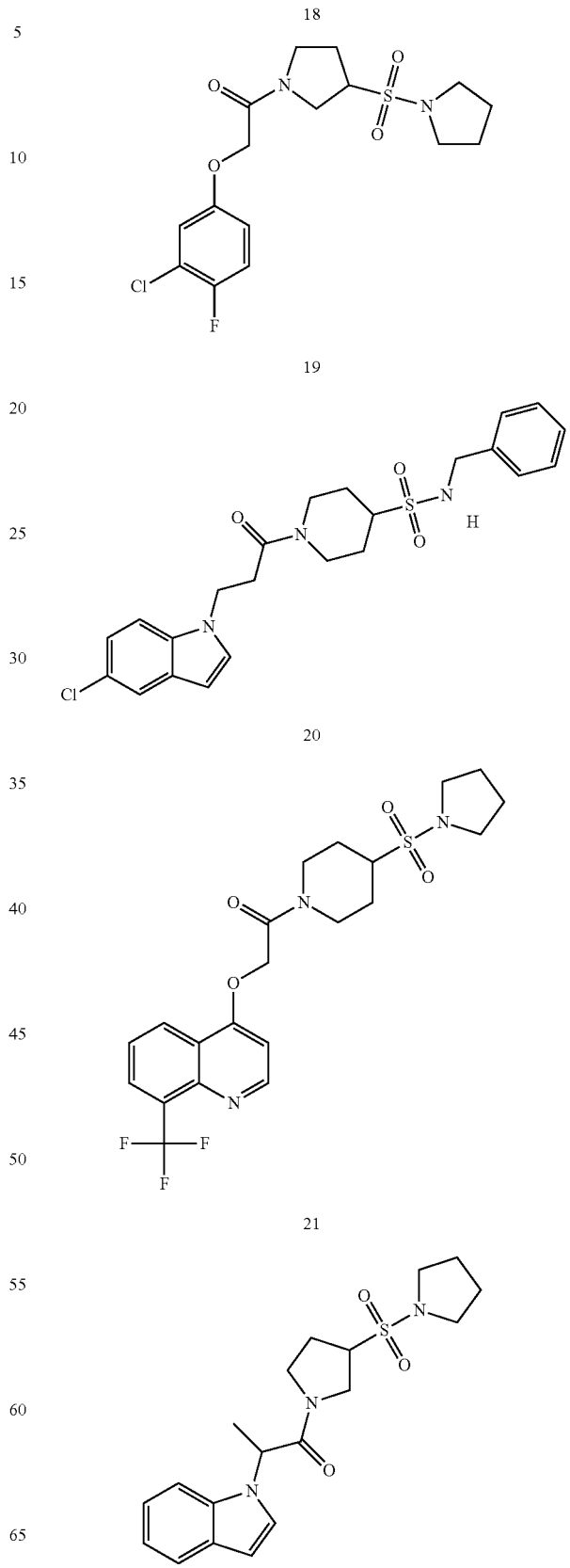

TABLE 1-continued
Exemplary compounds of Formulae I and II
22
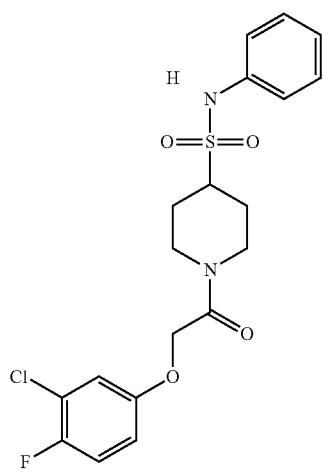
23
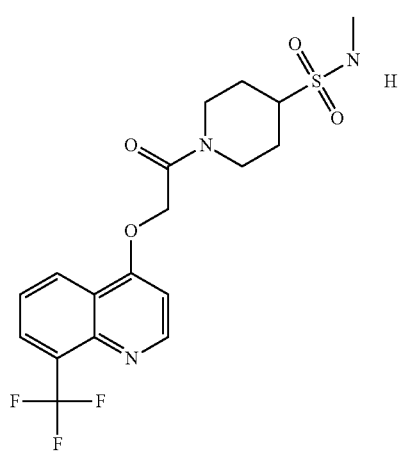
24
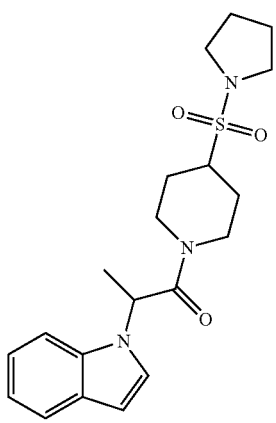
TABLE 1-continued
Exemplary compounds of Formulae I and II
25
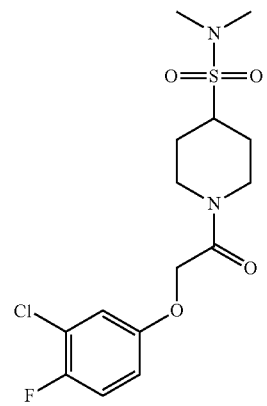
26
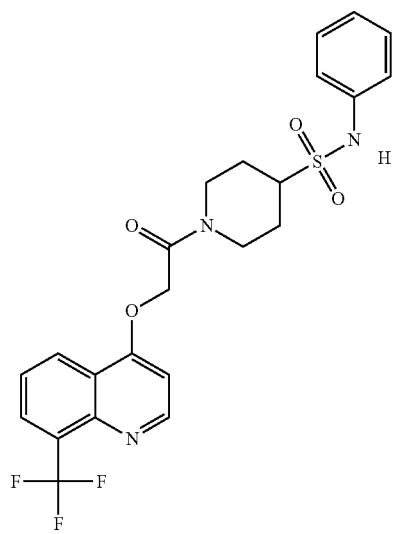
27
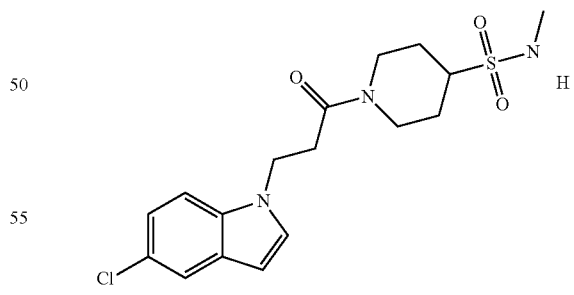
III. Synthesis
Compounds of formulae (I and II) can be prepared from commercially available starting materials by known methods. Scheme 1, illustrated below, is an exemplary method for preparing the compounds of the present invention.

Scheme 1:

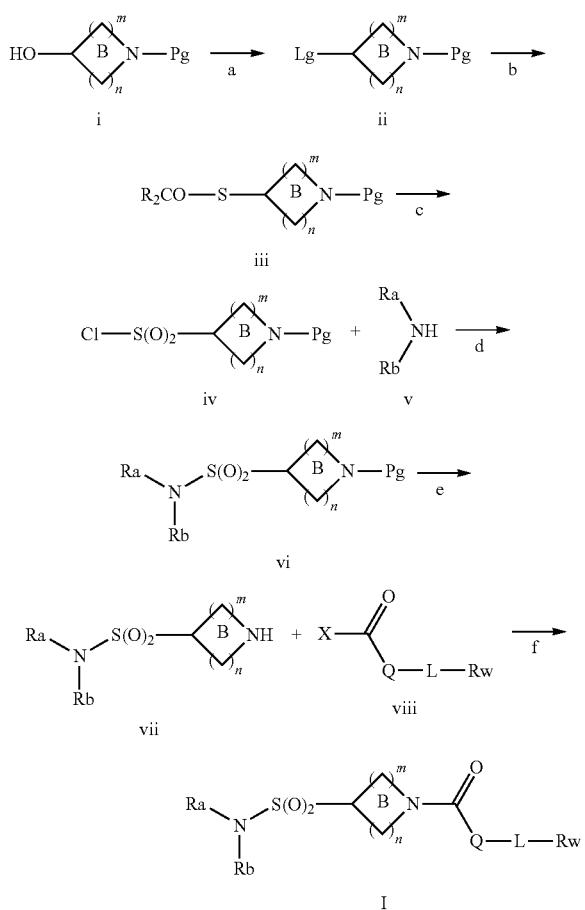

Referring to Scheme I, Pg represents an amine protecting group known in the art (see, for example, Theodora W. Greene and Peter G. M. Wuts, Protective Groups in Organic Synthesis, 3rd Edition, John Wiley & Sons Inc., 1999). Suitable protecting groups include, for example, t-butyloxycarbonyl (BOC) and benzyloxycarbonyl (CBz). In step a, the alcohol of compound i is converted to a leaving group Lg. Suitable leaving groups include, for example, halide or a sulfonate ester such as, for example, a mesylate, tosylate or trifluoromethylsulfonate. In step b, Lg is displaced with an alkaline metal thiocarboxylate such as, for example, potassium thioacetate to give the thio ester iii wherein $R_2$ is alkyl or aryl. Chlorination of iii with, for example chlorine or sulfuryl chloride, produces the sulfonyl chloride iv. Reaction of iv with the amine v (step d) produces the intermediate vi which, after removal of the protecting group from vi (step e), produces the amine vii. Reaction of vii with viii (step f) wherein X is —OH or a reactive acid derivative such as, for example, an acid chloride, produces compounds of the invention I. When X is —OH, the reaction of vii with viii is conducted in the presence of a coupling reagent such as for example, O-(7-azabenzotriazole-1-yl)-N,N,N'N'-tetramethyluronium hexafluorophosphate (HATU) or a carbodiimide under known conditions. In some embodiments, wherein the desired compound of formula I contains an —NH— within L, the nitrogen may be protected during the preparation with a suitable protecting group Pg as described above.

IV. Uses, Formulation and Administration

A. Pharmaceutically Acceptable Compositions

As discussed above, the present invention provides compounds that are inhibitors of voltage-gated sodium ion channels and/or calcium channels, and thus the present compounds are useful for the treatment of diseases, disorders, and conditions including, but not limited to acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrythmia, movement disorders, neuroendocrine disorders, ataxia, multiple sclerosis, irritable bowel syndrome, and incontinence. Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a voltage-gated sodium ion channel or calcium channel."

Pharmaceutically acceptable salts are well known in the art. For example, S. M. Berge, et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_1-C_4alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

B. Uses of Compounds and Pharmaceutically Acceptable Compositions

In yet another aspect, a method for the treatment or lessening the severity of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain is provided comprising administering an effective amount of a compound, or a pharmaceutically acceptable composition comprising a compound to a subject in need thereof. In certain embodiments, a method for the treatment or lessening the severity of acute, chronic, neuropathic, or inflammatory pain is provided comprising administering an effective amount of a compound or a pharmaceutically acceptable composition to a subject in need thereof. In certain other embodiments, a method for the treatment or lessening the severity of radicular pain, sciatica, back pain, head pain, or neck pain is provided comprising administering an effective amount of a compound or a pharmaceutically acceptable composition to a subject in need thereof. In still other embodiments, a method for the treatment or lessening the severity of severe or intractable pain, acute pain, postsurgical pain, back pain, tinnitis or cancer pain is provided comprising administering an effective amount of a compound or a pharmaceutically acceptable composition to a subject in need thereof.

In certain embodiments of the present invention, an "effective amount" of the compound or pharmaceutically acceptable composition is that amount effective for treating or lessening the severity of one or more of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, tinnitis or cancer pain.

The compounds and compositions, according to the method of the present invention, may be administered using any amount and any route of administration effective for treating or lessening the severity of one or more of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, tinnitis or cancer pain. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex, and diet of the patient; the time of administration, route of administration, and rate of excretion of the specific compound employed; the duration of the treatment; drugs used in combination or coincidental with the specific compound employed, and like factors well known in the medical arts. The term "patient," as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular cottonseed, groundnut, corn, germ, olive, castor, and sesame oils), glycerol, tetrahydrofurfuryl alcohol, polyethylene glycols, and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of voltage-gated sodium ion channels or calcium channels, preferably N-type calcium channels. In one embodiment, the compounds and compositions of the invention are inhibitors of one or more of NaV1.1, NaV1.2, NaV1.3, NaV1.4, NaV1.5, NaV1.6, NaV1.7, NaV1.8, NaV1.9, or CaV2.2, and thus, without wishing to be bound by any particular theory, the compounds and compositions are particularly useful for treating or lessening the severity of a disease, condition, or disorder where activation or hyperactivity of one or more of NaV1.1, NaV1.2, NaV1.3, NaV1.4, NaV1.5, NaV1.6, NaV1.7, NaV1.8, NaV1.9, or CaV2.2 is implicated in the disease, condition, or disorder. When activation or hyperactivity of NaV1.1, NaV1.2, NaV1.3, NaV1.4, NaV1.5, NaV1.6, NaV1.7, NaV1.8, NaV1.9, or CaV2.2, is implicated in a particular disease, condition, or disorder, the disease, condition, or disorder may also be referred to as a "NaV1.1, NaV1.2, NaV1.3, NaV1.4, NaV1.5, NaV1.6, NaV1.7, NaV1.8 or NaV1.9-mediated disease, condition or disorder" or a "CaV2.2-mediated condition or disorder". Accordingly, in another aspect, the present invention provides a method for treating or lessening the severity of a disease, condition, or disorder where activation or hyperactivity of one or more of NaV1.1, NaV1.2, NaV1.3, NaV1.4, NaV1.5, NaV1.6, NaV1.7, NaV1.8, NaV1.9, or CaV2.2 is implicated in the disease state.

The activity of a compound utilized in this invention as an inhibitor of NaV1.1, NaV1.2, NaV1.3, NaV1.4, NaV1.5, NaV1.6, NaV1.7, NaV1.8, NaV1.9, or CaV2.2 may be assayed according to methods described generally in the examples herein, or according to methods available to one of ordinary skill in the art.

In certain exemplary embodiments, compounds of the invention are useful as inhibitors of NaV1.3. In other embodiments, compounds of the invention are useful as inhibitors of NaV1.3 and CaV2.2. In still other embodiments, compounds of the invention are useful as inhibitors of CaV2.2.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated". For example, exemplary additional therapeutic agents include, but are not limited to: nonopioid analgesics (indoles such as Etodolac, Indomethacin, Sulindac, Tolmetin; naphthylalkanones such as Nabumetone; oxicams such as Piroxicam; para-aminophenol derivatives, such as Acetaminophen; propionic acids such as Fenoprofen, Flurbiprofen, Ibuprofen, Ketoprofen, Naproxen, Naproxen sodium, Oxaprozin; salicylates such as ASS (Asprin), Choline magnesium trisalicylate, Diflunisal; fenamates such as meclofenamic acid, Mefenamic acid; and pyrazoles such as Phenylbutazone); or opioid (narcotic) agonists (such as Codeine, Fentanyl, Hydromorphone, Levorphanol, Meperidine, Methadone, Morphine, Oxycodone, Oxymorphone, Propoxyphene, Buprenorphine, Butorphanol, Dezocine, Nalbuphine, and Pentazocine). Additionally, nondrug analgesic approaches may be utilized in conjunction with administration of one or more compounds of the invention. For example, anesthesiologic (intraspinal infusion, neural blocade), neurosurgical (neurolysis of CNS pathways), neurostimulatory (transcutaneous electrical nerve stimulation, dorsal column stimulation), physiatric (physical therapy, orthotic devices, diathermy), or psychologic (cognitive methods-hypnosis, biofeedback, or behavioral methods) approaches may also be utilized. Additional appropriate therapeutic agents or approaches are described generally in The Merck Manual, Seventeenth Edition, Ed. Mark H. Beers and Robert Berkow, Merck Research Laboratories, 1999, and the Food and Drug Administration website, www.fda.gov, the entire contents of which are hereby incorporated by reference.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to inhibiting one or more of NaV1.1, NaV1.2, NaV1.3, NaV1.4, NaV1.5, NaV1.6, NaV1.7, NaV1.8, NaV1.9, or CaV2.2 activity in a biological sample or a patient, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of one or more of NaV1.1, NaV1.2, NaV1.3, NaV1.4, NaV1.5, NaV1.6, NaV1.7, NaV1.8, NaV1.9, or CaV2.2 activity in a biological sample is useful for a variety of purposes that are known to one of skill in the art. Examples of such purposes include, but are not limited to, the study of sodium ion channels in biological and pathological phenomena; and the comparative evaluation of new sodium ion channel inhibitors.

EXAMPLES

Preparation 1:
4-Chlorosulfonyl-piperidine-1-carboxylic acid tert-butyl ester

Step 1a:
4-Methanesulfonyloxy-piperidine-1-carboxylic acid tert-butyl ester

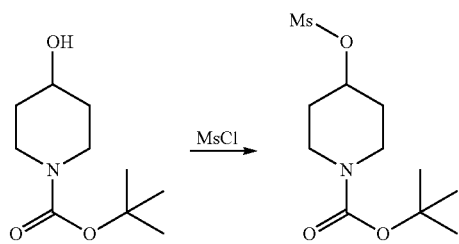

To a cooled (5-10° C.) mixture of N-Boc-4-hydroxypiperidine (25.0 g, 124 mmol) and triethylamine (19.6 ml, 136 mmol) in toluene (120 ml) was added slowly methanesulfonyl chloride (10.6 ml, 136 mmol) via a syringe. The rate of the addition was kept at such rate that the temperature of the reaction mixture did not rise above 20° C. After completion of the addition, the temperature was kept at room temperature for one and a half hours. Water (50 ml) was added to the mixture, and an emulsion formed that was broken by the addition of 100 ml toluene. The aqueous layer was extracted with 100 ml toluene and the combined organic layers were dried over sodium sulfate, filtered, and evaporated to dryness, leaving a white solid residue identified as the product (30.5 g, 87%), and which was used as such in the next step.

Step 1b: 4-Acetylsulfanyl-piperidine-1-carboxylic acid tert-butyl ester

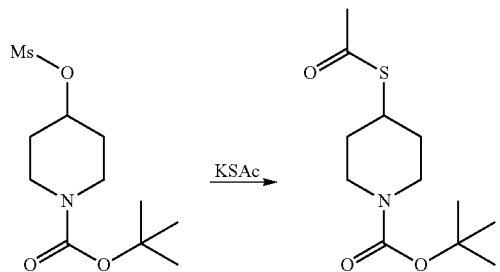

Crude 4-methanesulfonyloxy-piperidine-1-carboxylic acid tert-butyl ester was dissolved in 200 ml DMF, and potassium thioacetate (18.5 g, 162 mmol) was added. The mixture was stirred overnight under a nitrogen atmosphere at about 65° C. The reaction mixture solidified overnight, and after it was cooled to room temperature, 250 ml water and 250 ml TBME was added, and the mixture was stirred for 10 minutes. The layers were separated, and the aqueous layer was extracted with 200 ml TBME. The combined organic layers were washed with water (2×250 ml) and saturated aqueous NaCl solution (150 ml), dried over sodium sulfate, filtered, and evaporated to dryness (30.3 g, 94%) to give a dark-brown oil identified as the product by $^1$H-NMR, which was used without purification in the next step.

Step 1c: 4-Chlorosulfonyl-piperidine-1-carboxylic acid tert-butyl ester

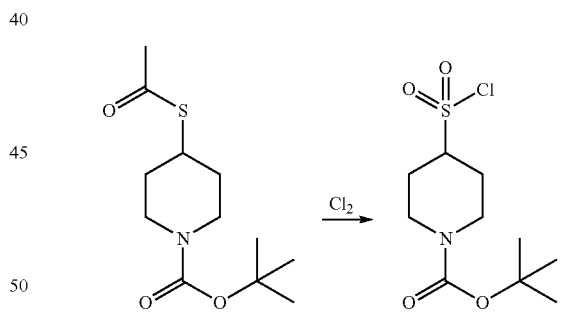

Crude intermediate 4-acetylsulfanyl-piperidine-1-carboxylic acid tert-butyl ester (30.3 g, 116 mmol) was dissolved in absolute ethanol (200 ml) and cooled to −10° C. on an ice-salt bath. Chlorine gas was bubbled through the solution for about 1 h. During this period, the mixture slowly turned lighter and the temperature was kept below +10° C. by cooling with the ice-salt bath and by adjusting the chlorine addition rate. After 1 hour, no more heat developed and the addition of chlorine was stopped. In total, 32 g $Cl_2$ was bubbled through. The reaction mixture was mixed with toluene (500 ml) and 10% aqueous NaCl solution (350 ml) (some heat developed, Tmax~30° C.). The organic layer was washed with 10% aq. NaCl solution (350 ml) and water (300 ml) and evaporated to dryness (19 g, 58%) to give a light-yellow oil. This oil was dissolved in 50 ml heptanes by heating and left crystallizing over the weekend at room temperature. The formed off-white solid was collected by filtration and washed with heptanes. The solid was recrystallized from 50 ml heptanes. Some impurities were removed by filtration of the hot solution. After crystallization, a white powder was collected by filtration and washed with heptanes and identified as the product by ¹H-NMR with 98% purity (DSC), m.p.=84.6° C.-85.7° C. (DSC).

General Procedure 1:

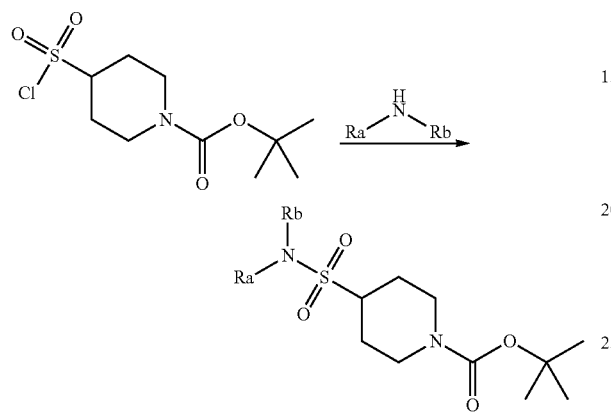

The amine (3 mmol) was added to a solution of 4-chlorosulfonyl-piperidine-1-carboxylic acid tert-butyl ester (0.426 g, 1.5 mmol), Et₃N (0.63 ml, 4.5 mmol) and DCM (5 ml). After stirring the reaction mixture for 16 h, it was poured into water (50 ml) and extracted with EtOAc (3×20 ml). The organic layers were combined and washed with a 0.1 N HCL solution (3×10 ml) and saturated aqueous NaCl solution (20 ml), dried over MgSO₄, and concentrated under reduced pressure. The product was used for the next step without further purification. Examples of 4-(amino-sulfonyl)-piperidine-1-carboxylic acid tert-butyl esters prepared according to General Procedure 1 include:

4-(Pyrrolidine-1-sulfonyl)-piperidine-1-carboxylic acid tert-butyl ester

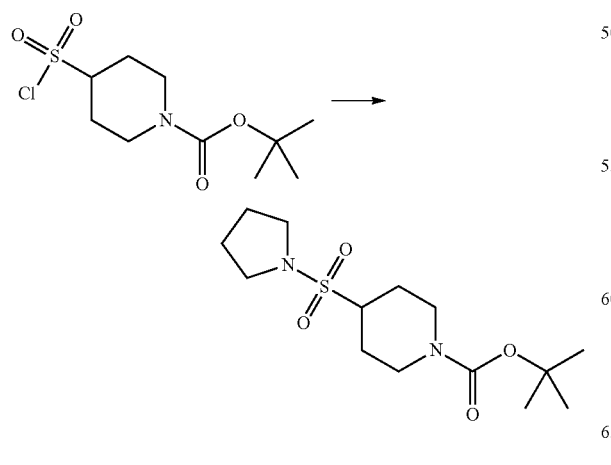

4-Phenylsulfamoyl-piperidine-1-carboxylic acid tert-butyl ester

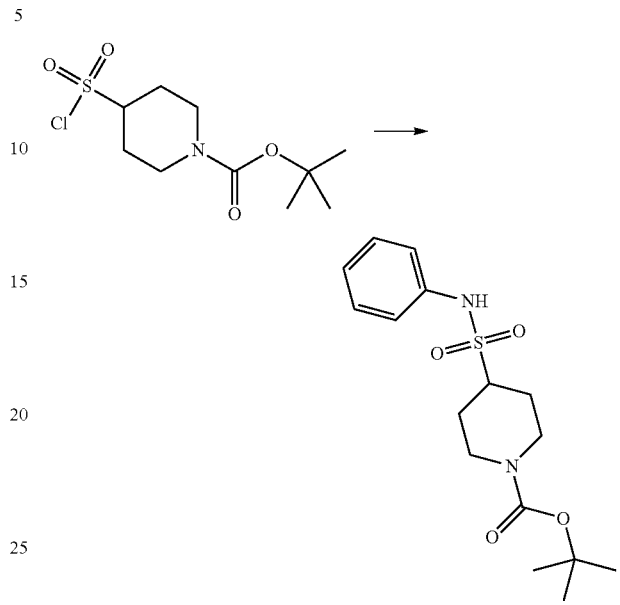

LC/MS (10-99% CH₃CN), M/Z: M+1 obs=341.0; $t_R$=2.96 min.

4-Benzylsulfamoyl-piperidine-1-carboxylic acid tert-butyl ester

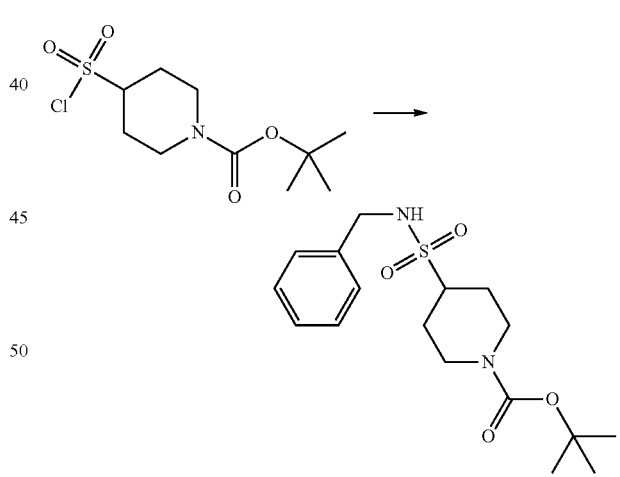

General Procedure 2:

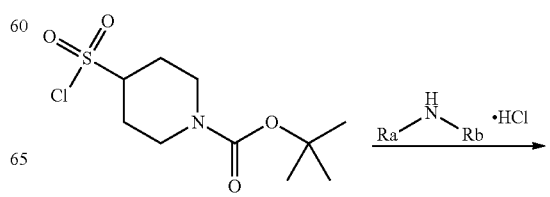

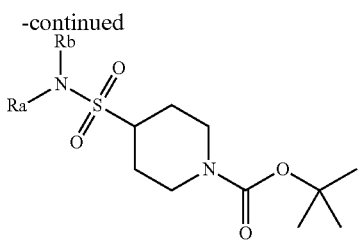

The amine hydrochloride was added to a solution of 4-chlorosulfonyl-piperidine-1-carboxylic acid tert-butyl ester (0.426 g, 1.5 mmol), Et₃N (1.26 ml, 9 mmol), and DCM (5 ml). After stirring the reaction mixture for 16 h, it was poured into water (50 ml) and extracted with EtOAc (3×20 ml). The organic layers were combined and washed with 0.1 N HCL (3×10 ml) and saturated aqueous NaCl solution (20 ml), dried over MgSO₄ and concentrated under reduced pressure. The product was used for the next steps without further purification. Other examples of 4-sulfamoyl-piperidine-1-carboxylic acid tert-butyl esters include:

4-Dimethylsulfamoyl-piperidine-1-carboxylic acid tert-butyl ester

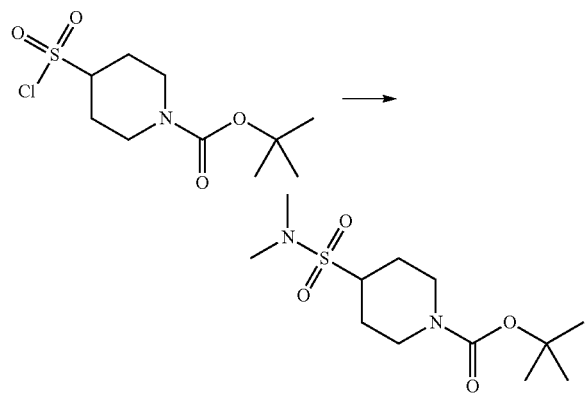

4-Methylsulfamoyl-piperidine-1-carboxylic acid tert-butyl ester

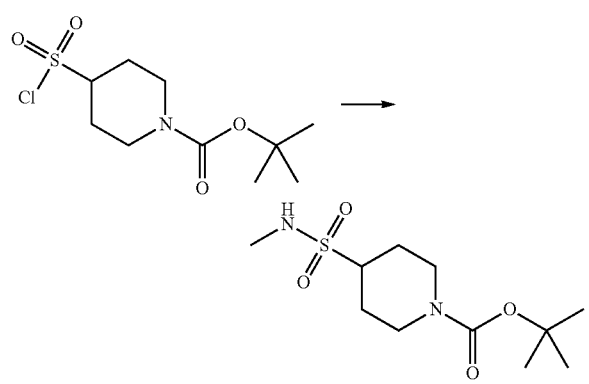

General Procedure 3:

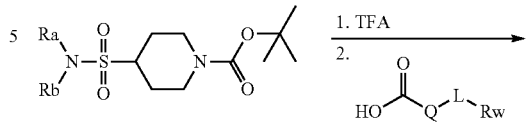

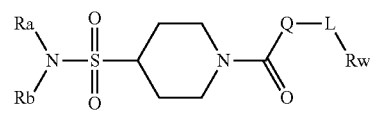

4-(Ra-Rb-sulfamoyl)-piperidine-1-carboxylic acid tert-butyl ester (0.1 mmol) was stirred in TFA:DCM (1:1) at RT for 2 h. After removing the solvents under reduced pressure and co-evaporating 2× with EtOH, the resulting solid was desiccated over KOH.

To a solution of the dried product and CH₃CN (0.3 ml), the carboxylic acid (0.11 mmol), HATU (0.042 g, 0.11 mmol), and Et₃N (30 mg, 0.3 mmol) were added. After stirring for 16 h at RT, the solvents were evaporated under reduced pressure. Purification with Gilson reverse phase HPLC gave desired product.

Example 1

2-(1H-Indol-1-yl)-1-(4-(pyrrolidin-1-ylsulfonyl)piperidin-1-yl)propan-1-one

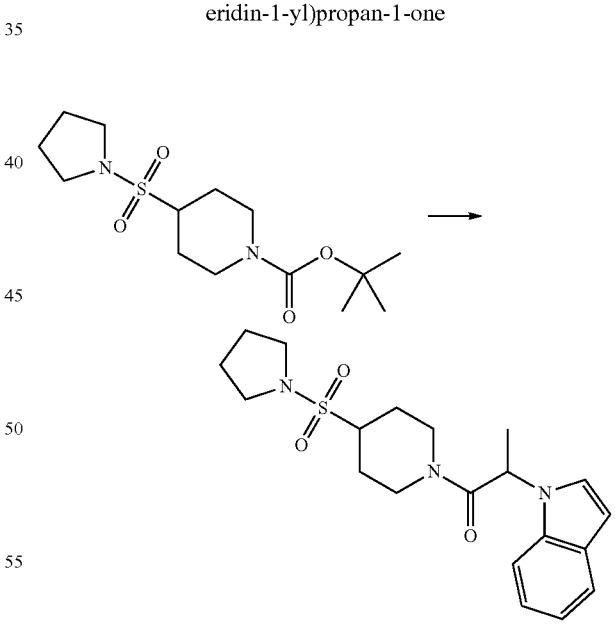

Synthesized according to general procedure 3. ¹H-NMR (400 MHz, CDCl3) δ 7.68-7.64 (m, 1H), 7.35-7.30 (m, 3H), 7.25 (t, J=7.6 Hz, 1H), 7.20-7.16 (m, 3H), 7.10-7.07 (m, 2H), 6.60-6.54 (m, 1H), 5.30 (t, J=6.6 Hz, 1H), 4.72 (dd, J=67.6, 13.5 Hz, 1H), 3.77-3.72 (m, 1H), 3.09 (d, J=11.4 Hz, 1H), 2.80-2.55 (m, 2H), 2.11-2.08 (m, 1H), 2.03 (s, 1H), 1.89-1.83 (m, 1H), 1.66-1.64 (m, 3H), 1.61-1.58 (m, 1H). LC/MS (10-99% CH₃CN), M/Z: M+1 obs=390.2; t$_R$=2.90 min.

Example 2

1-[3-(5-chloro-1H-indol-1-yl)propanoyl]-N-phenyl-piperidine-4-sulfonamide

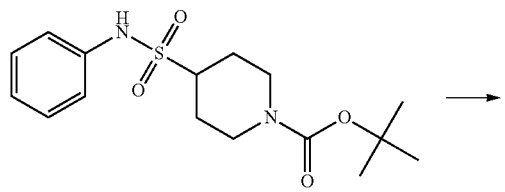

Synthesized according to general procedure 3. ¹H-NMR (400 MHz, CDCl3) δ 7.59 (d, J=1.9 Hz, 1H), 7.36 (t, J=7.9 Hz, 2H), 7.22-7.17 (m, 5H), 6.43 (d, J=3.1 Hz, 1H), 6.35 (s, 1H), 4.70 (d, J=13.5 Hz, 1H), 4.54-4.50 (m, 2H), 3.66 (d, J=13.4 Hz, 1H), 3.18-3.10 (m, 1H), 2.81-2.72 (m, 3H), 2.54-2.48 (m, 1H), 2.08 (d, J=13.6 Hz, 1H), 1.95 (d, J=13.4 Hz, 1H), 1.77-1.66 (m, 1H), 1.56-1.50 (m, 1H). LC/MS (10-99% CH₃CN), M/Z: M+1 obs=446; $t_R$=3.21 min.

Example 3

1-[2-(1H-Indol-1-yl)propanoyl]-N-phenyl-piperidine-4-sulfonamide

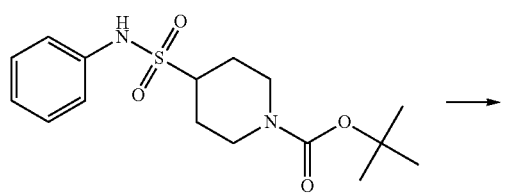

Synthesized according to general procedure 3. LC/MS (10-99% CH₃CN), M/Z: M+1 obs=412.0; $t_R$=3.07 min.

Example 4

N-Benzyl-1-[2-(3-chloro-4-fluoro-phenoxy)acetyl]-piperidine-4-sulfonamide

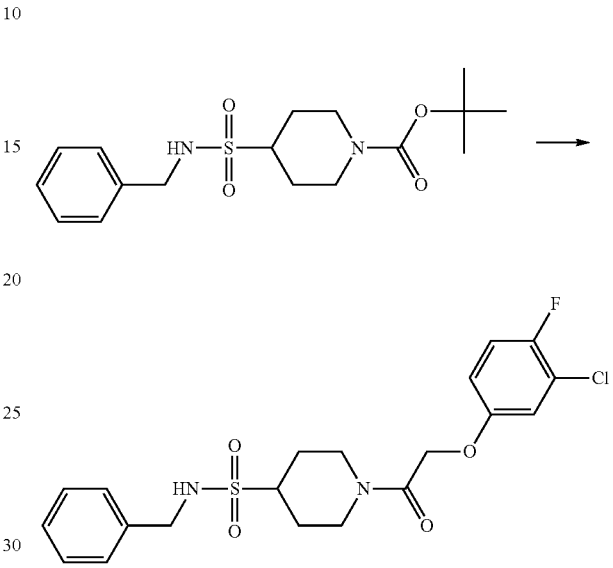

Synthesized according to general procedure 3. LC/MS (10-99% CH₃CN), M/Z: M+1 obs=442; $t_R$=3.06 min.

Example 5

N-Benzyl-1-[2-[[8-(trifluoromethyl)-4-quinolyl]oxy]acetyl]-piperidine-4-sulfonamide

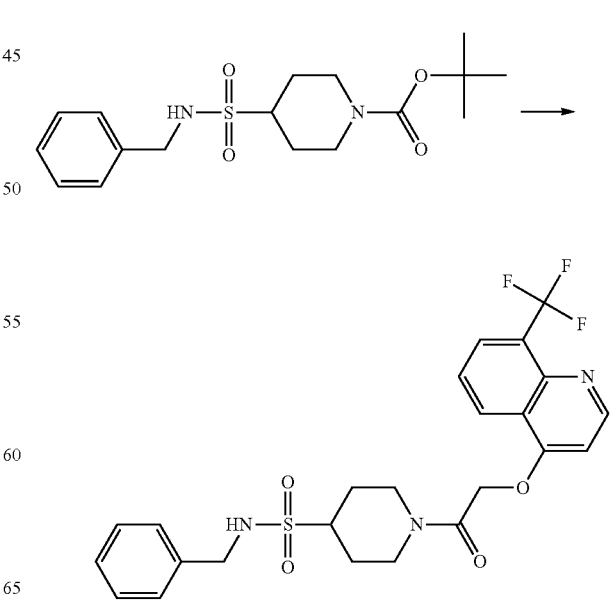

Synthesized according to general procedure 3. LC/MS (10-99% CH₃CN), M/Z: M+1 obs=508; $t_R$=2.74 min.

Example 6

N,N-Dimethyl-1-[2-[[8-(trifluoromethyl)-4-quinolyl]oxy]acetyl]-piperidine-4-sulfonamide

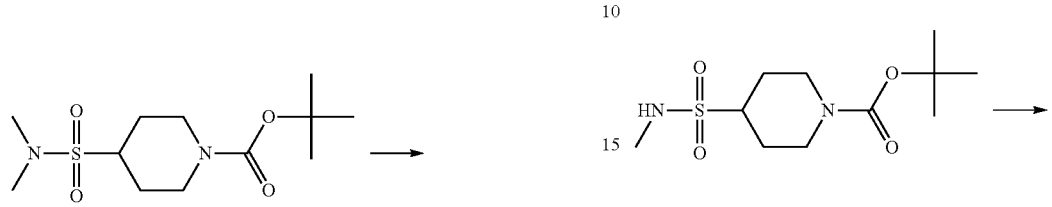

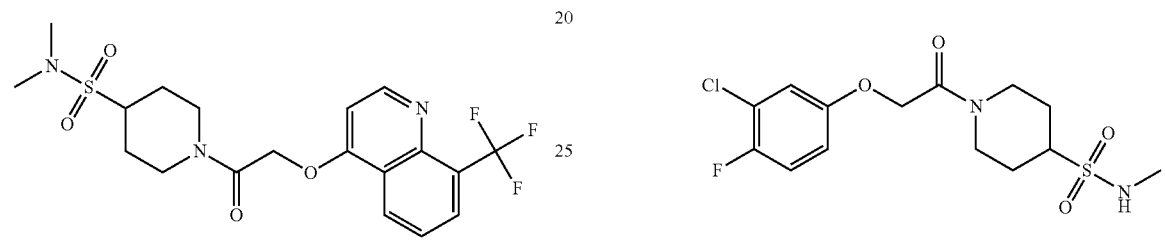

Synthesized according to general procedure 3. ¹H-NMR (400 MHz, acetic acid-d4) δ 9.34 (d, J=6.2 Hz, 1H), 8.76 (d, J=8.4 Hz, 1H), 8.36 (d, J=7.2 Hz, 1H), 7.90 (t, J=8.1 Hz, 1H), 7.44 (d, J=5.7 Hz, 1H), 5.41 (s, 2H), 4.66 (d, J=14.0 Hz, 1H), 3.99 (d, J=13.1 Hz, 1H), 3.33-3.25 (m, 2H), 2.97 (s, 6H), 2.88-2.79 (m, 1H), 2.27-2.22 (m, 1H), 2.18-2.14 (m, 1H), 1.96-1.84 (m, 2H). LC/MS (10-99% CH₃CN), M/Z: M+1 obs=446; $t_R$=2.30 min.

Example 7

1-[3-(5-Chloro-1H-indol-1-yl)propanoyl]-N,N-dimethyl-piperidine-4-sulfonamide

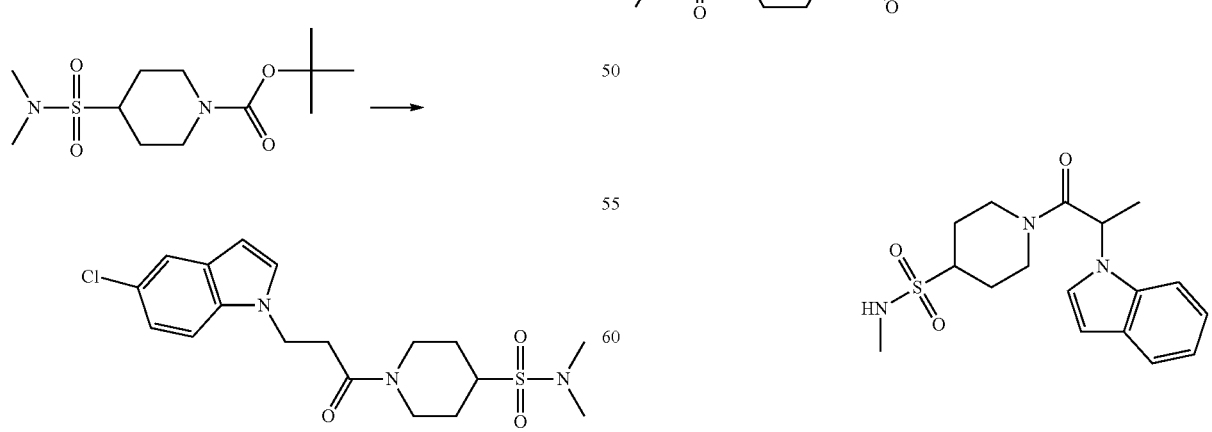

Synthesized according to general procedure 3. LC/MS (10-99% CH₃CN), M/Z: M+1 obs=398; $t_R$=2.91 min.

Example 8

N-Methyl-1-[2-(3-chloro-4-fluoro-phenoxy)acetyl]-piperidine-4-sulfonamide

Synthesized according to general procedure 3. LC/MS (10-99% CH₃CN), M/Z: M+1 obs=365; $t_R$=2.43 min.

Example 9

1-(2-(1H-Indol-1-yl)propanoyl)-N-methylpiperidine-4-sulfonamide

Synthesized according to general procedure 3. LC/MS (10-99% CH₃CN), M/Z: M+1 obs=350; $t_R$=2.5 min.

Preparation 2: 3-Chlorosulfonyl-pyrrolidine-1-carboxylic acid tert-butyl ester

Step 2a: (3R)-Pyrrolidin-3-ol maleate (xi)

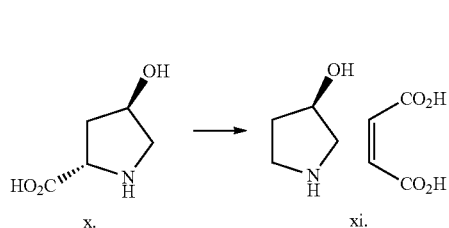

A suspension of (2S,4R)-(−)-4-hydroxy proline (50.0 g, 381 mmol) in cyclohexanol (250 ml) with 2-cyclohexen-1-one (5.0 ml) was refluxed overnight under a nitrogen atmosphere. The red solution was cooled to about 30° C., and maleic acid (45 g, 388 mmol) was added at once to the solution. Ethyl acetate (500 ml) was slowly added, and after stirring for an additional 15 min, the formed crystals were collected by filtration, washed with ethyl acetate (3×200 ml), and dried under vacuum to yield an off-white solid (53.2 g, 262 mmol, 69%) identified as (3R)-pyrrolidin-3-ol maleate by $^1$H-NMR.

Step 2b: (3R)-3-Hydroxy-pyrrolidine-1-carboxylic acid tert-butyl ester (xii)

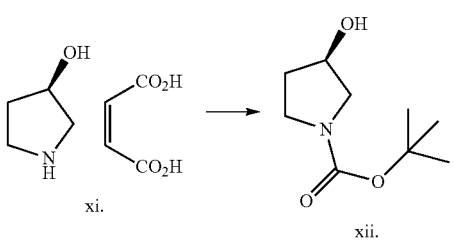

(3R)-pyrrolidin-3-ol maleate (67.6 g, 333 mmol) was slowly poured in a stirred mixture of sodium bicarbonate (139 g, 1.65 mol) in water (600 ml). Subsequently, di-tert-butyl dicarbonate (110 g, 504 mmol) was added, and the resulting mixture was stirred overnight at room temperature. Ethyl acetate (600 ml) was added, and the mixture was filtered in order to remove undissolved salts. The layers were separated and the aqueous layer was extracted with ethyl acetate (300 ml). The combined organic layers were washed with saturated aqueous NaCl solution (400 ml), dried over sodium sulfate, filtered, and evaporated to dryness. Yield: 85.7 g (q) of a dark oil that was recrystallized from 150 ml heptanes, yielding 62.2 g (77%) of a white solid identified as xii by $^1$H-NMR.

Step 2c: (3S)-3-Hydroxy-pyrrolidine-1-carboxylic acid tert-butyl ester (xiv)

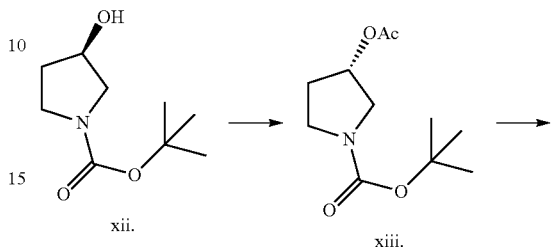

Compound xii (25 g, 134 mmol) and triphenylphosphine (42.9 g, 147 mmol) were dissolved in dry THF (200 ml) under a nitrogen atmosphere and were cooled to 0° C. on an ice/water bath. Diisopropyl azodicarboxylate (DIAD) (30.5 ml, 154 mmol) was added drop wise followed by the addition of acetic acid (8.1 ml, 141 mmol). The resulting mixture was left warming to room temperature overnight and was evaporated to dryness. Heptanes (240 ml) and ethyl acetate (10 ml) were added to the residual oil and the mixture was stirred at 50° C. for one hour and than at room temperature for 1 additional hour. The solids were removed by filtration and the filtrate was evaporated to dryness to give 51.3 g of an oil. The oil was purified by column chromatography over silica gel with ethyl acetate/heptanes (20:80-40:60) to give xiii (21.6 g, 94 mmol, 70%) identified by $^1$H-NMR, some residual DIAD fragments were still present.

This material was dissolved in methanol/water (100 ml, 1:1), and potassium carbonate (15.6 g, 113 mmol) was added. After stirring for one hour at room temperature, 350 ml water was added and the aqueous solution was extracted with TBME (250 ml and 200 ml). The combined organic extracts were washed with saturated aqueous NaCl solution (200 ml), dried over sodium sulfate, filtered, and evaporated to dryness to yield a yellow oil identified as (3S)-3-hydroxy-pyrrolidine-1-carboxylic acid tert-butyl ester (xiv) by $^1$H-NMR.

Step 2d: (3R)-3-Acetylsulfanyl-pyrrolidine-1-carboxylic acid tert-butyl ester (xvi)

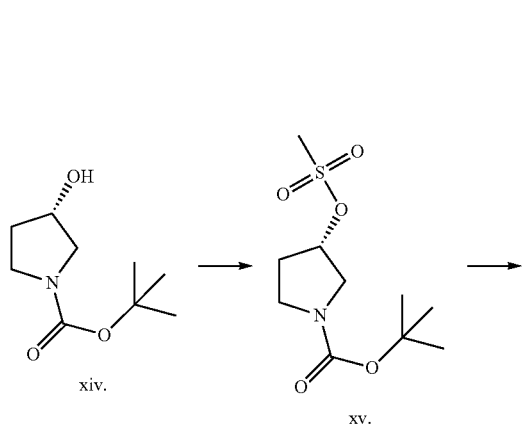

To a cooled (−5 to −10° C., ice/salt bath) solution of pyrrolidinol (xiv) (18.2 g, 98 mmol) and triethylamine (28 ml, 196 mmol) in ethylacetate (150 ml) was slowly added methanesulfonyl chloride (9.1 ml, 118 mmol) via a syringe. After completion of addition, the mixture was left stirring at room temperature for one hour. Water (100 ml) was added, and the layers were separated. The organic layer was washed with 1 N aq. HCl solution (100 ml), 5% aq. sodium bicarbonate solution (100 ml), and with saturated aqueous NaCl solution (100 ml). Then, the organic layer was dried over sodium sulfate, filtered, and evaporated to dryness under reduced pressure, yielding 24.3 g (92 mmol, 94%) of a yellow oil. This oil was dissolved in 150 ml dry DMF, and potassium thioacetate (13.5 g, 119 mmol) was added. The resulting mixture was heated to 65° C. overnight under a nitrogen atmosphere, the solution started to solidify after about half an hour. After the mixture was cooled to room temperature, water (250 ml) and TBME (200 ml) were added. The layers were separated, and the aqueous layer was extracted with another portion of TBME (250 ml). The combined organic layers were washed with water (3×250 ml), and with brine (200 ml), dried over sodium sulfate, filtered and evaporated to dryness under reduced pressure. Yield: 20.8 g (92%) of a yellow oil, identified as xvi by $^1$H-NMR.

Step 2e: 3-Chlorosulfonyl-pyrrolidine-1-carboxylic acid tert-butyl ester

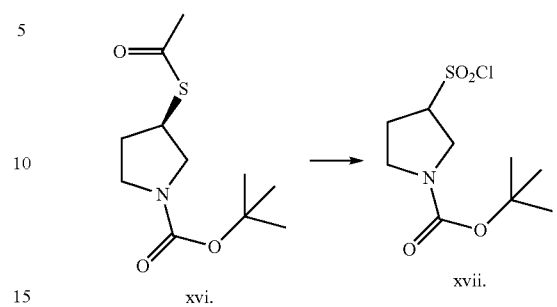

Thioacetate (xvi) (20.8 g, 85 mmol) was dissolved in absolute ethanol (200 ml) and cooled to −10° C. in an ice/salt bath. Chlorine gas was slowly bubbled through the ethanolic solution. The speed of the chlorine addition was adjusted to keep the temperature of the solution below about 10° C. (with ice/salt bath cooling). In total, 31 g (440 mmol) chlorine gas was bubbled through in about 1 hour. To the resulting mixture, toluene (250 ml) and saturated aqueous NaCl solution (250 ml) were added. A slight increase in temperature was observed (Tmax~25° C.), and after stirring for 10 minutes, the layers were separated, and the organic layer was washed with saturated aqueous NaCl solution (200 ml) and water (250 ml), and was evaporated to dryness to yield 21.2 g (93%) of a yellow oil. This oil was purified by column chromatography over silica gel with ethyl acetate/heptanes (1:3) as the solvent to give 14.0 g (61%) of a brownish oil, identified as xvii by $^1$H-NMR. According to the NMR, some impurity was still present. The e.e. was determined on the p-anisidine derivative of xvii. It was found that xvii was completely racemized.

(3S)-3-Acetylsulfanyl-pyrrolidine-1-carboxylic acid tert-butyl ester (xix)

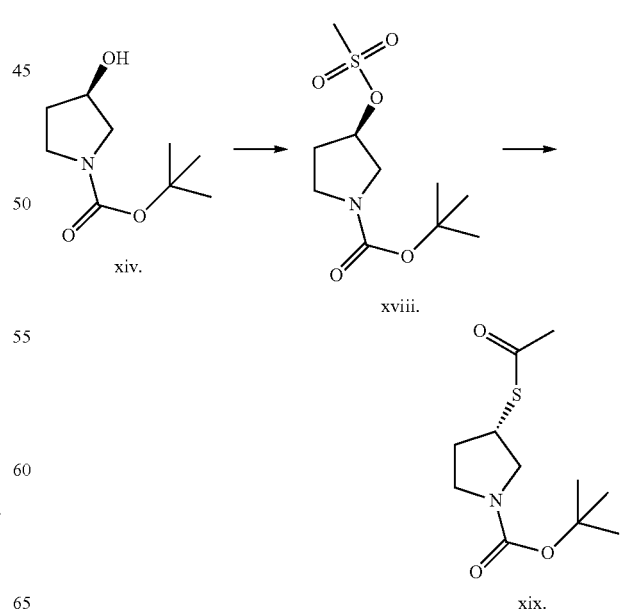

A mixture of xiv (20.0 g, 107 mol) and triethylamine (31 ml, 214 mmol) in ethyl acetate (200 ml) was cooled to −10−−5° C. with an ice/salt bath. To this mixture was slowly added mesylchloride (9.9 ml, 128 mmol) via a syringe. Immediately, a white precipitate started forming, stirring was continued for half an hour at room temperature. Then, water (100 ml) was added and the organic layer was separated and washed with 1 N aq. HCl solution (100 ml), 5% aq. NaHCO$_3$ solution (100 ml), and finally with saturated aqueous NaCl solution (100 ml). The organic layer was dried over sodium sulfate, filtered, and evaporated to dryness, yielding 28.9 g (107 mmol) of a oil identified as xvii by $^1$H-NMR. This oil was dissolved in DMF (250 ml) and potassium thioacetate (16.2 g, 142 mmol) was added. The resulting mixture was stirred under a nitrogen atmosphere overnight at about 60° C. After 15 minutes, as solid started forming. The mixture was cooled to room temperature, and water (250 ml) plus TBME (250 ml) were added to the solidified mixture. The resulting mixture was stirred for 10 minutes and subsequently, the layers were separated. The aqueous layer was extracted with 250 ml TBME, and the combined TBME layers were washed with water (3×200 ml), saturated aqueous NaCl solution (200 ml), dried over sodium sulfate, filtered, and evaporated to dryness to yield 23.5 g (90%) of an orange oil identified as xix by $^1$H-NMR.

3-Chlorosulfonyl-pyrrolidine-1-carboxylic acid tert-butyl ester (xvii)

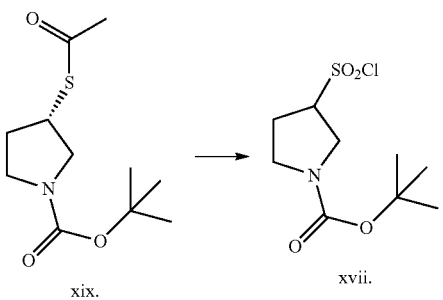

Thioacetate xix (32.7 g, 133 mmol) was dissolved in absolute ethanol (300 ml) and cooled to −10° C. on an ice/salt bath. Chlorine gas was bubbled through at such a rate that the temperature of the ethanolic solution did no rise above 0° C. In total, 38 g Cl$_2$ was bubbled through. To the resulting solution was added toluene (250 ml) and saturated aqueous NaCl solution (200 ml). The mixture was stirred at room temperature for 10 min. The layers were separated, and the organic layer was washed with saturated aqueous NaCl solution (200 ml) and water (200 ml) and was evaporated to dryness under reduced pressure. The resulting oil (17 g) was purified by column chromatography (SiO$_2$, EtOAc/heptanes 1:3) to yield 8.6 g of a brownish oil. The e.e. of the p-anisidine derivative was checked and the compound was found to be completely racemized.

General Procedure 4:

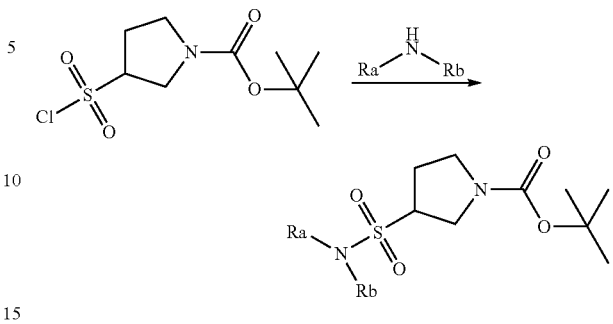

The amine (3 mmol) was added to a solution of (±)-3-chlorosulfonyl-pyrrolidine-1-carboxylic acid tert-butyl ester (0.27 g, 1 mmol), Et$_3$N (0.42 ml, 3 mmol) and DCM (5 ml). After stirring the reaction mixture for 16 h, it was poured into water (50 ml) and extracted with EtOAc (3×20 ml). The organic layers were combined, washed with a 0.1 N HCL solution (3×10 ml) and saturated aqueous NaCl solution (20 ml), dried over MgSO$_4$, and concentrated under reduced pressure. The product was used for the next step without further purification. Examples of the 3-(amino-sulfonyl)-pyrrolidine-1-carboxylic acid tert-butyl ester prepared following General Procedure 4 include:

3-(Pyrrolidine-1-sulfonyl)-pyrrolidine-1-carboxylic acid tert-butyl ester

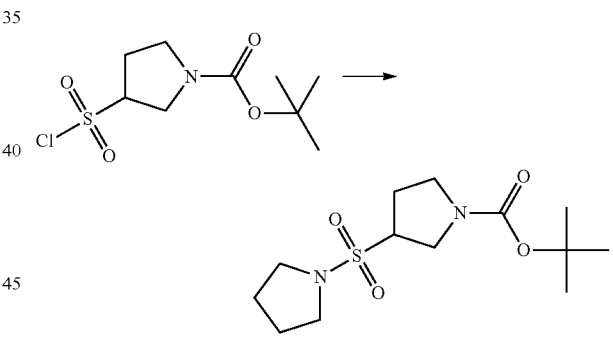

3-Phenylsulfamoyl-pyrrolidine-1-carboxylic acid tert-butyl ester

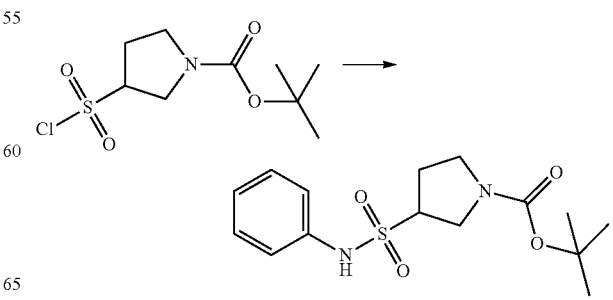

LC/MS (10-99% CH$_3$CN), M/Z: M+1 (minus Boc) obs=227.3; t$_R$=3.17 min.

3-Benzylsulfamoyl-pyrrolidine-1-carboxylic acid tert-butyl ester

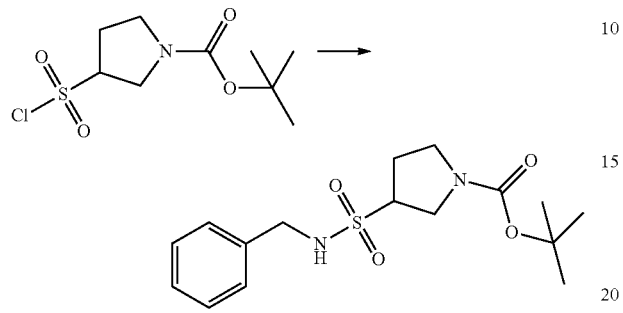

LC/MS (10-99% CH$_3$CN), M/Z: M+1 (minus Boc) obs=241.3; t$_R$=3.19 min.

General Procedure 5:

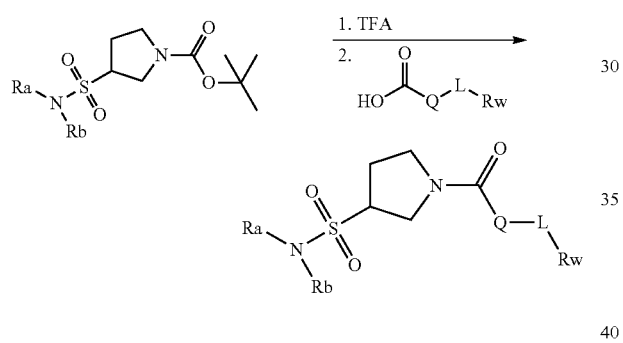

3-(Ra-Rb-Sulfamoyl)-pyrrolidine-1-carboxylic acid tert-butyl ester (0.1 mmol) was stirred in TFA:DCM (1:1) at RT for 2 h. After removing the solvents under reduced pressure and co-evaporating 2× with EtOH, the resulting solid was desiccated over KOH. To a solution of the dried product and CH$_3$CN (0.3 ml), the carboxylic acid (0.11 mmol), HATU (0.042 g, 0.11 mmol), and Et$_3$N (30 mg, 0.3 mmol) were added. After stirring for 16 h at RT, the solvents were evaporated under reduced pressure. Purification with Gilson reverse phase HPLC gave desired product.

Example 10

3-(5-Chloro-1H-indol-1-yl)-1-(3-pyrrolidin-1-ylsulfonylpyrrolidin-1-yl)-propan-1-one

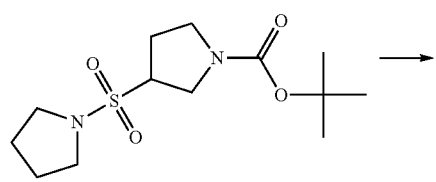

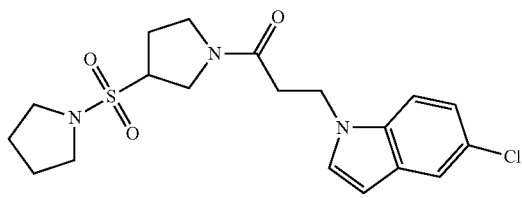

Synthesized according to general procedure 5. LC/MS (10-99% CH$_3$CN), M/Z: M+1 obs=410; t$_R$=2.99 min.

Example 11

1-(3-Pyrrolidin-1-ylsulfonylpyrrolidin-1-yl)-2-[[8-(trifluoromethyl)-4-quinolyl]oxy]ethanone

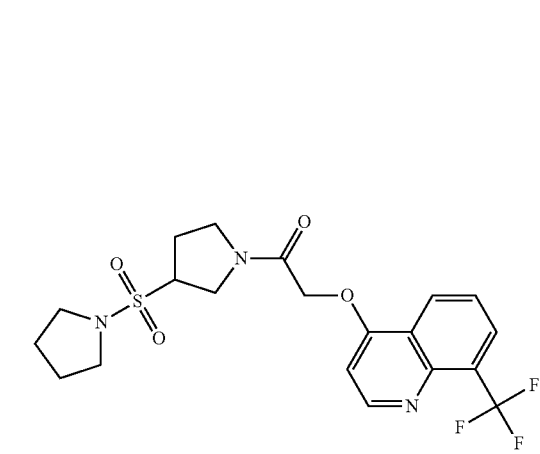

Synthesized according to general procedure 5. $^1$H-NMR (400 MHz, MeOD) δ 8.88 (d, J=5.9 Hz, 1H), 8.75 (d, J=8.4 Hz, 1H), 8.31 (d, J=7.1 Hz, 1H), 7.83 (t, J=8.0 Hz, 1H), 7.29 (dd, J=11.1, 5.8 Hz, 1H), 5.33-5.30 (m, 2H), 4.19-3.55 (m, 5H), 3.46-3.40 (m, 4H), 2.60-2.45 (m, 1H), 2.40-2.35 (m, 1H), 2.02-1.94 (m, 4H). LC/MS (10-99% CH$_3$CN), M/Z: M+1 obs=457; t$_R$=2.41 min.

Example 12

1-[2-(1H-Indol-1-yl)propanoyl]-N-phenyl-pyrrolidine-3-sulfonamide

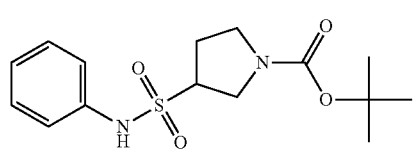

Synthesized according to general procedure 5. $^1$H-NMR (400 MHz, MeOD) δ 7.60-7.54 (m, 1H), 7.42-7.03 (m, 10H), 6.53-6.49 (m, 1H), 5.45-5.38 (m, 1H), 4.05-3.56 (m, 4H), 3.09-2.95 (m, 1H), 2.45-2.16 (m, 2H), 1.65-1.55 (m, 3H). LC/MS (10-99% CH$_3$CN), M/Z: M+1 obs=398; t$_R$=3.02 min.

Example 13

N-Benzyl-1-[2-(3-chloro-4-fluoro-phenoxy)acetyl]-pyrrolidine-3-sulfonamide

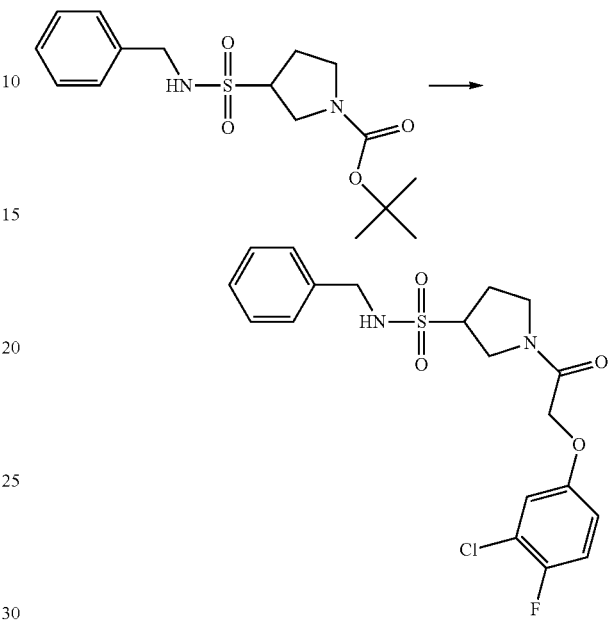

Synthesized according to general procedure 5. $^1$H-NMR (400 MHz, MeOD) δ 7.40-7.35 (m, 4H), 7.32-7.28 (m, 1H), 7.20-7.09 (m, 2H), 6.95-6.90 (m, 1H), 4.73 (d, J=5.3 Hz, 2H), 4.30 (d, J=5.6 Hz, 2H), 3.95-3.50 (m, 5H), 2.51-2.21 (m, 2H). LC/MS (10-99% CH$_3$CN), M/Z: M+1 obs=427; t$_R$=2.96 min.

A person reasonably skilled in the chemical arts can use the examples and schemes above to synthesize compounds of the present invention, including the compounds in Table 2.

TABLE 2

| | Experimental Data for Sample Compounds of Formulae (I and II) | | |
|---|---|---|---|
| Compound No. | Compound Structure | LC-MS M + 1 | LC-RT min |
| 1 | ![structure] | 350 | 2.50 |

TABLE 2-continued

Experimental Data for Sample Compounds of Formulae (I and II)

| Compound No. | Compound Structure | LC-MS M + 1 | LC-RT min |
|---|---|---|---|
| 14 | 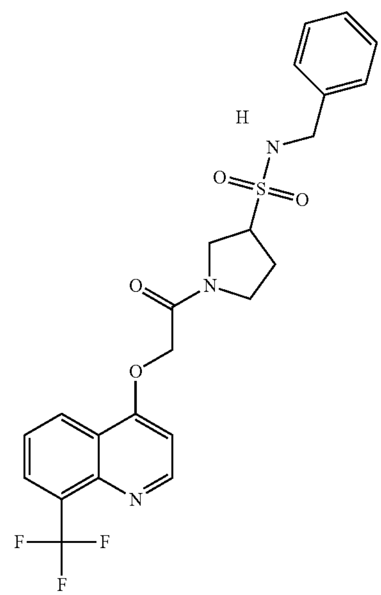 | 494 | 2.69 |
| 15 | 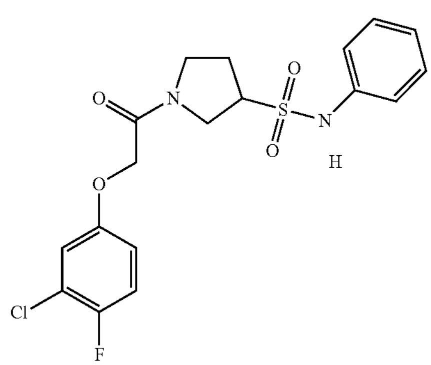 | 413 | 2.96 |
| 16 | 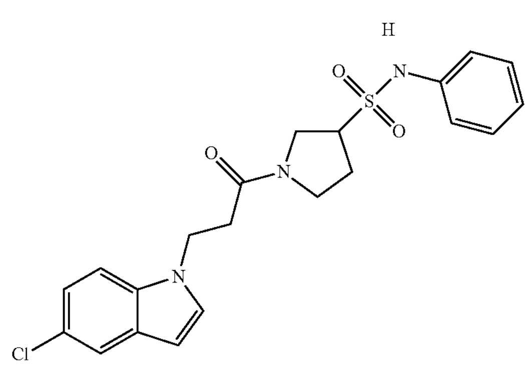 | 432 | 3.18 |

TABLE 2-continued

Experimental Data for Sample Compounds of Formulae (I and II)

| Compound No. | Compound Structure | LC-MS M + 1 | LC-RT min |
|---|---|---|---|
| 17 | 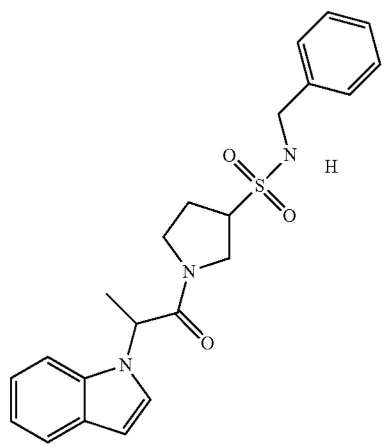 | 412 | 3.03 |
| 18 | 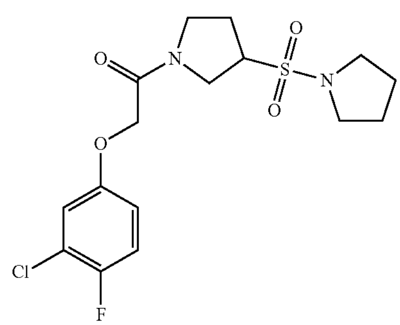 | 391 | 2.74 |
| 19 | 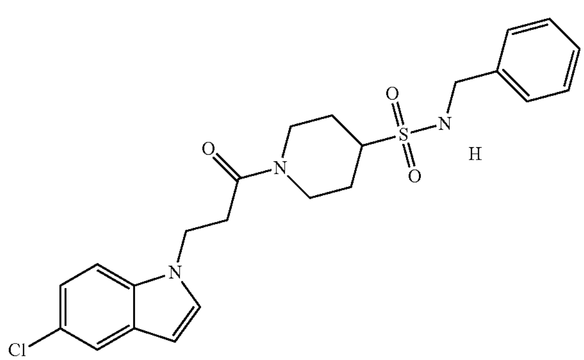 | 461 | 3.23 |

TABLE 2-continued

Experimental Data for Sample Compounds of Formulae (I and II)

| Compound No. | Compound Structure | LC-MS M + 1 | LC-RT min |
|---|---|---|---|
| 20 | 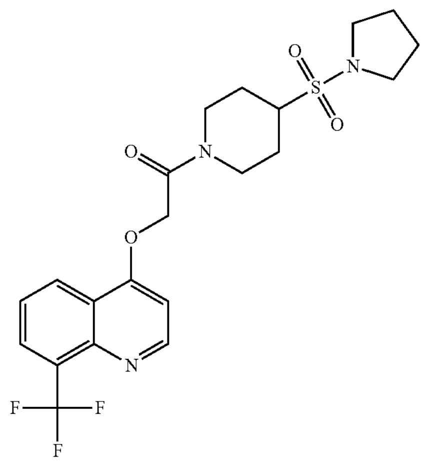 | 473 | 2.49 |
| 21 | 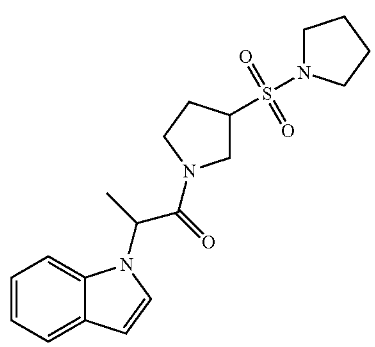 | 376 | 2.80 |
| 22 | 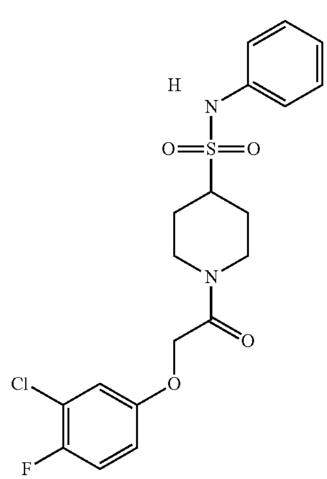 | 427 | 3.02 |

TABLE 2-continued
Experimental Data for Sample Compounds of Formulae (I and II)
| Compound No. | Compound Structure | LC-MS M + 1 | LC-RT min |
|---|---|---|---|
| 23 | 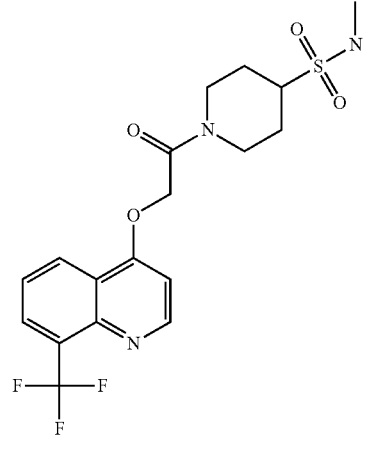 | 432 | 2.09 |
| 25 | 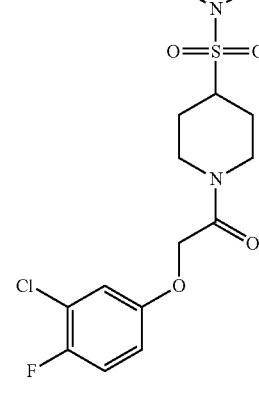 | 379 | 2.66 |
| 26 | 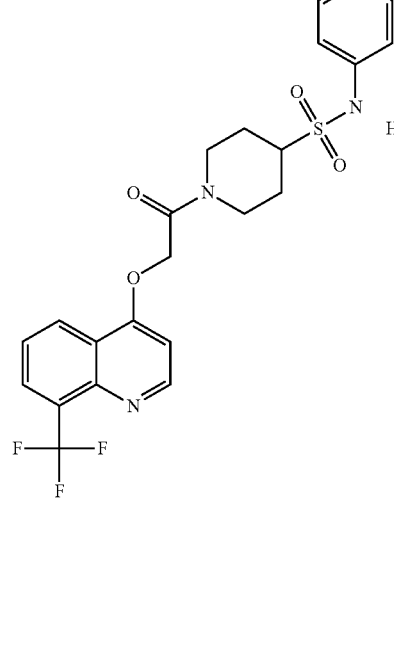 | 494 | 2.70 |

TABLE 2-continued

Experimental Data for Sample Compounds of Formulae (I and II)

| Compound No. | Compound Structure | LC-MS M + 1 | LC-RT min |
|---|---|---|---|
| 27 | 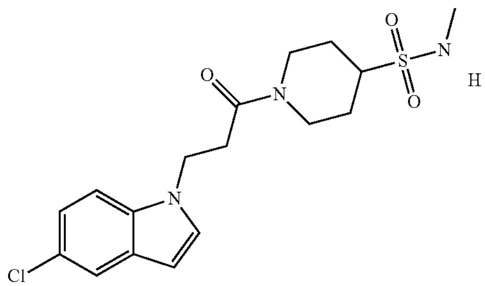 | 384 | 2.71 |

Assays for Detecting and Measuring NaV Inhibition Properties of Compound

Optical Methods for Assaying NaV Inhibition Properties of Compounds:

Compounds of the invention are useful as antagonists of voltage-gated sodium ion channels. Antagonist properties of test compounds were assessed as follows. Cells expressing the NaV of interest were placed into microtiter plates. After an incubation period, the cells were stained with fluorescent dyes sensitive to the transmembrane potential. The test compounds were added to the microtiter plate. The cells were stimulated with either a chemical or electrical means to evoke a NaV dependent membrane potential change from unblocked channels, which was detected and measured with trans-membrane potential-sensitive dyes. Antagonists were detected as a decreased membrane potential response to the stimulus. The optical membrane potential assay utilized voltage-sensitive FRET sensors described by Gonzalez and Tsien (See, Gonzalez, J. E. and R. Y. Tsien (1995) "Voltage sensing by fluorescence resonance energy transfer in single cells" *Biophys J* 69(4): 1272-80, and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR®) (See, Gonzalez, J. E., K. Oades, et al. (1999) "Cell-based assays and instrumentation for screening ion-channel targets" *Drug Discov Today* 4(9): 431-439).

VIPR® Optical Membrane Potential Assay Method with Chemical Stimulation

Cell Handling and Dye Loading 24 hours before the assay on VIPR, CHO cells endogenously expressing a NaV1.2 type voltage-gated NaV are seeded in 96-well poly-lysine coated plates at 60,000 cells per well. Other subtypes are performed in an analogous mode in a cell line expressing the NaV of interest.

1) On the day of the assay, medium is aspirated and cells are washed twice with 225 μL of Bath Solution #2 (BS#2).
2) A 15 μM CC2-DMPE solution is prepared by mixing 5 mM coumarin stock solution with 10% Pluronic 127 1:1 and then dissolving the mix in the appropriate volume of BS#2.
3) After bath solution is removed from the 96-well plates, the cells are loaded with 80 μL of the CC2-DMPE solution. Plates are incubated in the dark for 30 minutes at room temperature.
4) While the cells are being stained with coumarin, a 15 μL oxonol solution in BS#2 is prepared. In addition to DiSBAC$_2$(3), this solution should contain 0.75 mM ABSC1 and 30 μL veratridine (prepared from 10 mM EtOH stock, Sigma #V-5754).
5) After 30 minutes, CC2-DMPE is removed and the cells are washed twice with 225 μL of BS#2. As before, the residual volume should be 40 μL.
6) Upon removing the bath, the cells are loaded with 80 μL of the DiSBAC$_2$(3) solution, after which test compound, dissolved in DMSO, is added to achieve the desired test concentration to each well from the drug addition plate and mixed thoroughly. The volume in the well should be roughly 121 μL. The cells are then incubated for 20-30 minutes.
7) Once the incubation is complete, the cells are ready to be assayed on VIPR® with a sodium addback protocol. 120 μL of Bath solution #1 is added to stimulate the NaV dependent depolarization. 200 μL tetracaine was used as an antagonist positive control for block of the NaV channel.

Analysis of VIPR® Data:

Data are analyzed and reported as normalized ratios of background-subtracted emission intensities measured in the 460 nm and 580 nm channels. Background intensities are then subtracted from each assay channel. Background intensities are obtained by measuring the emission intensities during the same time periods from identically treated assay wells in which there are no cells. The response as a function of time is then reported as the ratios obtained using the following formula:

$$R(t) = \frac{(Intensity_{460\,nm} - Background_{460\,nm})}{(Intensity_{580\,nm} - Background_{580\,nm})}$$

The data is further reduced by calculating the initial ($R_i$) and final ($R_f$) ratios. These are the average ratio values during part or all of the pre-stimulation period, and during sample points during the stimulation period. The response to the stimulus $R=R_f/R_i$ is then calculated. For the Na$^+$ addback analysis time windows, baseline is 2-7 sec and final response is sampled at 15-24 sec.

Control responses are obtained by performing assays in the presence of a compound with the desired properties (positive control), such as tetracaine, and in the absence of pharmacological agents (negative control). Responses to the negative (N) and positive (P) controls are calculated as above. The compound antagonist activity A is defined as:

$$A = \frac{R-P}{N-P} * 100$$

where R is the ratio response of the test compound

Solutions [mM]

Bath Solution #1: NaCl 160, KCl 4.5, $CaCl_2$ 2, $MgCl_2$ 1, HEPES 10, pH 7.4 with NaOH Bath Solution #2 TMA-Cl 160, $CaCl_2$ 0.1, $MgCl_2$ 1, HEPES 10, pH 7.4 with KOH (final K concentration ~5 mM)

CC2-DMPE: prepared as a 5 mM stock solution in DMSO and stored at −20° C.

$DiSBAC_2(3)$: prepared as a 12 mM stock in DMSO and stored at −20° C.

ABSC1: prepared as a 200 mM stock in distilled $H_2O$ and stored at room temperature Cell Culture CHO cells are grown in DMEM (Dulbecco's Modified Eagle Medium; GibcoBRL #10569-010) supplemented with 10% FBS (Fetal Bovine Serum, qualified; GibcoBRL #16140-071) and 1% Pen-Strep (Penicillin-Streptomycin; GibcoBRL #15140-122). Cells are grown in vented cap flasks, in 90% humidity and 10% $CO_2$, to 100% confluence. They are usually split by trypsinization 1:10 or 1:20, depending on scheduling needs, and grown for 2-3 days before the next split.

VIPR® Optical Membrane Potential Assay Method with Electrical Stimulation

The following is an example of how NaV1.3 inhibition activity is measured using the optical membrane potential method #2. Other subtypes are performed in an analogous mode in a cell line expressing the NaV of interest.

HEK293 cells stably expressing NaV1.3 are plated into 96-well microtiter plates. After an appropriate incubation period, the cells are stained with the voltage sensitive dyes CC2-DMPE/$DiSBAC_2(3)$ as follows.

Reagents:

100 mg/mL Pluronic F-127 (Sigma #P2443), in dry DMSO 10 mM $DiSBAC_2(3)$ (Aurora #00-100-010) in dry DMSO 10 mM CC2-DMPE (Aurora #00-100-008) in dry DMSO 200 mM ABSC1 in $H_2O$ Hank's Balanced Salt Solution (Hyclone #SH30268.02) supplemented with 10 mM HEPES (Gibco #15630-080)

Loading Protocol:

2×CC2-DMPE=20 µM CC2-DMPE: 10 mM CC2-DMPE is vortexed with an equivalent volume of 10% pluronic, followed by vortexing in required amount of HBSS containing 10 mM HEPES. Each cell plate will require 5 mL of 2×CC2-DMPE. 50 µL of 2×CC2-DMPE is added to wells containing washed cells, resulting in a 10 µM final staining concentration. The cells are stained for 30 minutes in the dark at RT.

2×DISBAC$_2$(3) with ABSC1=6 µM DISBAC$_2$(3) and 1 mM ABSC1: The required amount of 10 mM DISBAC$_2$(3) is added to a 50 ml conical tube and mixed with 1 µL 10% pluronic for each mL of solution to be made and vortexed together. Then HBSS/HEPES is added to make up 2× solution. Finally, the ABSC1 is added.

The 2×DiSBAC$_2$(3) solution can be used to solvate compound plates. Note that compound plates are made at 2× drug concentration. Wash stained plate again, leaving residual volume of 50 µL. Add 50 uL/well of the 2×DiSBAC$_2$(3) w/ABSC1. Stain for 30 minutes in the dark at RT.

The electrical stimulation instrument and methods of use are described in ION Channel Assay Methods PCT/US01/21652, herein incorporated by reference. The instrument comprises a microtiter plate handler, an optical system for exciting the coumarin dye while simultaneously recording the coumarin and oxonol emissions, a waveform generator, a current- or voltage-controlled amplifier, and a device for inserting electrodes in well. Under integrated computer control, this instrument passes user-programmed electrical stimulus protocols to cells within the wells of the microtiter plate.

Reagents

Assay buffer #1: 140 mM NaCl, 4.5 mM KCl, 2 mM $CaCl_2$, 1 mM $MgCl_2$, 10 mM HEPES, 10 mM glucose, pH 7.40, 330 mOsm Pluronic stock (1000×): 100 mg/mL pluronic 127 in dry DMSO Oxonol stock (3333×): 10 mM $DiSBAC_2(3)$ in dry DMSO Coumarin stock (1000×): 10 mM CC2-DMPE in dry DMSO ABSC1 stock (400×): 200 mM ABSC1 in water Assay Protocol 1. Insert or use electrodes into each well to be assayed.
2. Use the current-controlled amplifier to deliver stimulation wave pulses for 3 s. Two seconds of pre-stimulus recording are performed to obtain the un-stimulated intensities. Five seconds of post-stimulation recording are performed to examine the relaxation to the resting state.

Data Analysis

Data are analyzed and reported as normalized ratios of background-subtracted emission intensities measured in the 460 nm and 580 nm channels. Background intensities are then subtracted from each assay channel. Background intensities are obtained by measuring the emission intensities during the same time periods from identically treated assay wells in which there are no cells. The response as a function of time is then reported as the ratios obtained using the following formula:

$$R(t) = \frac{(Intensity_{460\,nm} - Background_{460\,nm})}{(Intensity_{580\,nm} - Background_{580\,nm})}$$

The data is further reduced by calculating the initial ($R_i$) and final ($R_f$) ratios. These are the average ratio values during part or all of the pre-stimulation period, and during sample points during the stimulation period. The response to the stimulus $R=R_f/R_i$ is then calculated.

Control responses are obtained by performing assays in the presence of a compound with the desired properties (positive control), such as tetracaine, and in the absence of pharmacological agents (negative control). Responses to the negative (N) and positive (P) controls are calculated as above. The compound antagonist activity A is defined as:

$$A = \frac{R-P}{N-P} * 100$$

where R is the ratio response of the test compound.

Electrophysiology Assays for NaV Activity and Inhibition of Test Compounds

Patch clamp electrophysiology was used to assess the efficacy and selectivity of sodium channel blockers in dorsal root ganglion neurons. Rat neurons were isolated from the dorsal root ganglions and maintained in culture for 2 to 10 days in the presence of NGF (50 ng/ml) (culture media consisted of NeurobasalA supplemented with B27, glutamine and antibiotics). Small diameter neurons (nociceptors, 8-12 μm in diameter) have been visually identified and probed with fine tip glass electrodes connected to an amplifier (Axon Instruments). The "voltage clamp" mode has been used to assess the compound's IC50 holding the cells at −60 mV. In addition, the "current clamp" mode has been employed to test the efficacy of the compounds in blocking action potential generation in response to current injections. The results of these experiments have contributed to the definition of the efficacy profile of the compounds.

VOLTAGE-CLAMP Assay in DRG Neurons

TTX-resistant sodium currents were recorded from DRG somata using the whole-cell variation of the patch clamp technique. Recordings were made at room temperature (~22° C.) with thick walled borosilicate glass electrodes (WPI; resistance 3-4 MΩ) using an Axopatch 200B amplifier (Axon Instruments). After establishing the whole-cell configuration, approximately 15 minutes were allowed for the pipette solution to equilibrate within the cell before beginning recording. Currents were lowpass filtered between 2-5 kHz and digitally sampled at 10 kHz. Series resistance was compensated 60-70% and was monitored continuously throughout the experiment. The liquid junction potential (−7 mV) between the intracellular pipette solution and the external recording solution was not accounted for in the data analysis. Test solutions were applied to the cells with a gravity driven fast perfusion system (SF-77; Warner Instruments).

Dose-response relationships were determined in voltage clamp mode by repeatedly depolarizing the cell from the experiment specific holding potential to a test potential of +10 mV once every 60 seconds. Blocking effects were allowed to plateau before proceeding to the next test concentration.

Solutions

Intracellular solution (in mM): Cs—F (130), NaCl (10), MgCl$_2$ (1), EGTA (1.5), CaCl$_2$ (0.1), HEPES (10), glucose (2), pH=7.42, 290 mOsm.

Extracellular solution (in mM): NaCl (138), CaCl$_2$ (1.26), KCl (5.33), KH$_2$PO$_4$ (0.44), MgCl$_2$ (0.5), MgSO$_4$ (0.41), NaHCO$_3$ (4), Na$_2$HPO$_4$ (0.3), glucose (5.6), HEPES (10), CdCl$_2$ (0.4), NiCl$_2$ (0.1), TTX (0.25×10$^{-3}$).

CURRENT-CLAMP Assay for NaV Channel Inhibition Activity of Compounds

Cells were current-clamped in whole-cell configuration with a MultiClamp 700A amplifier (Axon Inst). Borosilicate pipettes (4-5 MOhm) were filled with (in mM): 150 K-gluconate, 10 NaCl, 0.1 EGTA, 10 HEPES, 2 MgCl$_2$, (buffered to pH 7.34 with KOH). Cells were bathed in (in mM): 140 NaCl, 3 KCl, 1 MgCl, 1 CaCl, and 10 HEPES). Pipette potential was zeroed before seal formation; liquid junction potentials were not corrected during acquisition. Recordings were made at room temperature.

Examples of activities and efficacies of the ABC transporter modulators of formulae (I and II) are shown below in Table 3. The compound activity for the ABC transporter modulators is illustrated with "+++" if activity was measured to be less than 5 μM, "++" if activity was measured to be 5 μM to 20 μM, and "+" if activity was measured to be greater than 20 μM. The efficacy for ABC transporter modulation is illustrated with "+++" if efficacy was calculated to be 100% or greater, "++" if efficacy was calculated to be between 25% and 100%, and "+" if efficacy was calculated to be 25% or less.

TABLE 3

| Copd Number | Activity |
|---|---|
| 1 | None |
| 2 | ++ |
| 3 | ++ |
| 4 | ++ |
| 5 | + |
| 6 | Not Tested |
| 7 | + |
| 8 | Not Tested |
| 9 | Not Tested |
| 10 | ++ |
| 11 | + |
| 12 | ++ |
| 13 | ++ |
| 14 | ++ |
| 15 | ++ |
| 16 | ++ |
| 17 | ++ |
| 18 | + |
| 19 | ++ |
| 20 | + |
| 21 | + |
| 22 | Not Tested |
| 23 | + |
| 24 | Not Tested |
| 25 | Not Tested |
| 26 | Not Tested |
| 27 | Not Tested |

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of modulating a sodium ion channel, comprising contacting a cell with a compound having the structure of formula I:

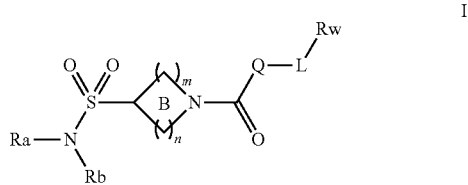

or a pharmaceutically acceptable salt thereof, wherein:

Ring B is optionally substituted with 1-2 of halo, cyano, nitro, haloalkyl, alkoxy, sulfonyl, sulfinyl, sulfanyl, amino, carboxy, or an optionally substituted aliphatic;

each Ra is independently H, an optionally substituted aliphatic, an optionally substituted phenyl, or an optionally substituted benzyl; wherein the aliphatic, phenyl, or benzyl is optionally substituted with halo, cyano, nitro, haloalkyl, alkoxy, sulfonyl, sulfinyl, sulfanyl, amino, carboxy, or aliphatic;

each Rb is independently H, an optionally substituted aliphatic, an optionally substituted phenyl or an optionally substituted benzyl, wherein the aliphatic, phenyl, or benzyl is optionally substituted with halo, cyano, nitro, haloalkyl, alkoxy, sulfonyl, sulfinyl, sulfanyl, amino, carboxy, or aliphatic, or Ra and Rb together with the nitrogen atom to which they are bound form a heterocyclic ring, optionally substituted with halo, cyano, nitro, haloalkyl, alkoxy, sulfonyl, sulfinyl, sulfanyl, amino, carboxy, or aliphatic;

each Q is a branched or unbranched $C_1$-$C_4$-alkyl optionally substituted with halo, cyano, nitro, haloalkyl, alkoxy, sulfonyl, sulfinyl, sulfanyl, amino, carboxy, or aliphatic;

each L is absent, —O—, —NRc-, or —S—;

each Rc is H, or aliphatic optionally substituted with halo, cyano, nitro, haloalkyl, alkoxy, sulfonyl, sulfinyl, sulfanyl, amino, carboxy, or aliphatic;

each Rw is phenyl, indole, or quinoline, wherein the phenyl, indole, or quinoline is optionally substituted with halo, cyano, nitro, haloalkyl, alkoxy, sulfonyl, sulfinyl, sulfanyl, amino, carboxy, or aliphatic;

each n is 1, 2, or 3; and each m is 1, 2, or 3, provided that the sum of n and m is 3, 4, 5, or 6.

2. The method of claim 1, wherein Ra is H or aliphatic.
3. The method of claim 2, wherein Ra is H.
4. The method of claim 2, wherein Ra is aliphatic.
5. The method of claim 4, wherein Ra is methyl.
6. The method of claim 1, wherein Rb is benzyl.
7. The method of claim 1, wherein Rb is phenyl.
8. The method of claim 1, wherein Rb is aliphatic.
9. The method of claim 1, wherein Rb is alkyl.
10. The method of claim 9, wherein Rb is methyl.
11. The method of claim 1, wherein Ra and Rb together with the nitrogen atom to which they are bound form a heterocycloalkyl.
12. The method of claim 11, wherein Ra and Rb together with the nitrogen atom to which they are bound form pyrrolidinyl.
13. The method of claim 1, wherein Rw is phenyl.
14. The method of claim 13, wherein the phenyl is substituted with 1-3 of halo or haloalkyl.
15. The method of claim 1, wherein Rw is an indolyl or quinolinyl.
16. The method of claim 15, wherein Rw is an indolyl.
17. The method of claim 16, wherein the indolyl is substituted with 1-3 of halo or haloalkyl.
18. The method of claim 15, wherein Rw is quinolinyl.
19. The method of claim 18, wherein the quinolinyl is substituted with 1-3 of halo or haloalkyl.
20. The method of claim 1, wherein Q is —$CH_2$— or —C(alkyl)(H)—.
21. The method of claim 20, wherein Q is —$CH_2$—.
22. The method of claim 20, wherein Q is —C(alkyl)(H)—.
23. The method of claim 1, wherein L is O.
24. The method of claim 1, wherein n is 2.
25. The method of claim 1, wherein m is 2.
26. A method of modulating a sodium ion channel, comprising contacting a cell with a compound having the structure of formula II:

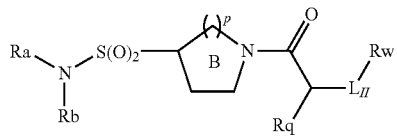

or a pharmaceutically acceptable salt thereof, wherein
ring B is optionally substituted with 1-2 of halo, cyano, nitro, haloalkyl, alkoxy, sulfonyl, sulfinyl, sulfanyl, amino, carboxy, or an optionally substituted aliphatic;

each Ra is independently H, aliphatic, phenyl or benzyl, wherein the aliphatic, phenyl, or benzyl is optionally substituted with halo, cyano, nitro, haloalkyl, alkoxy, sulfonyl, sulfinyl, sulfanyl, amino, carboxy, or aliphatic;

each Rb is independently H, aliphatic, phenyl, or benzyl wherein the aliphatic, phenyl, or benzyl is optionally substituted with halo, cyano, nitro, haloalkyl, alkoxy, sulfonyl, sulfinyl, sulfanyl, amino, carboxy, or aliphatic, or Ra and Rb together with the nitrogen atom to which they are bound form a heterocyclic ring, optionally substituted with halo, cyano, nitro, haloalkyl, alkoxy, sulfonyl, sulfinyl, sulfanyl, amino, carboxy, or aliphatic;

each Rq is H or aliphatic optionally substituted with halo, cyano, nitro, haloalkyl, alkoxy, sulfonyl, sulfinyl, sulfanyl, amino, carboxy, or aliphatic;

each $L_{II}$ is absent, —$CH_2$—, —O—, —NRc-, or —S—;

each Rc is H, or aliphatic, optionally substituted with halo, cyano, nitro, haloalkyl, alkoxy, sulfonyl, sulfinyl, sulfanyl, amino, carboxy, or aliphatic;

each Rw is phenyl, indole, or quinoline, wherein the phenyl, indole, or quinoline is optionally substituted with halo, cyano, nitro, haloalkyl, alkoxy, sulfonyl, sulfinyl, sulfanyl, amino, carboxy, or aliphatic; and each p is 1 or 2.

27. A method of modulating a sodium ion channel, comprising contacting a cell with a compound selected from:

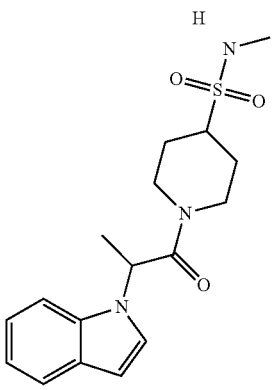

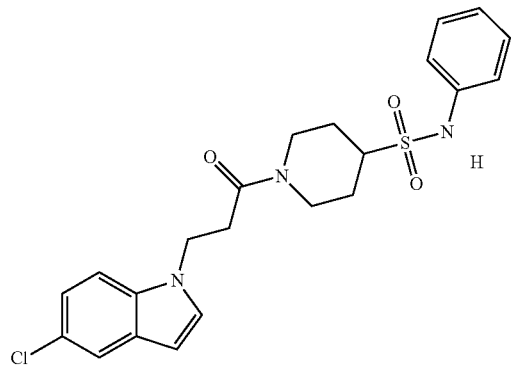

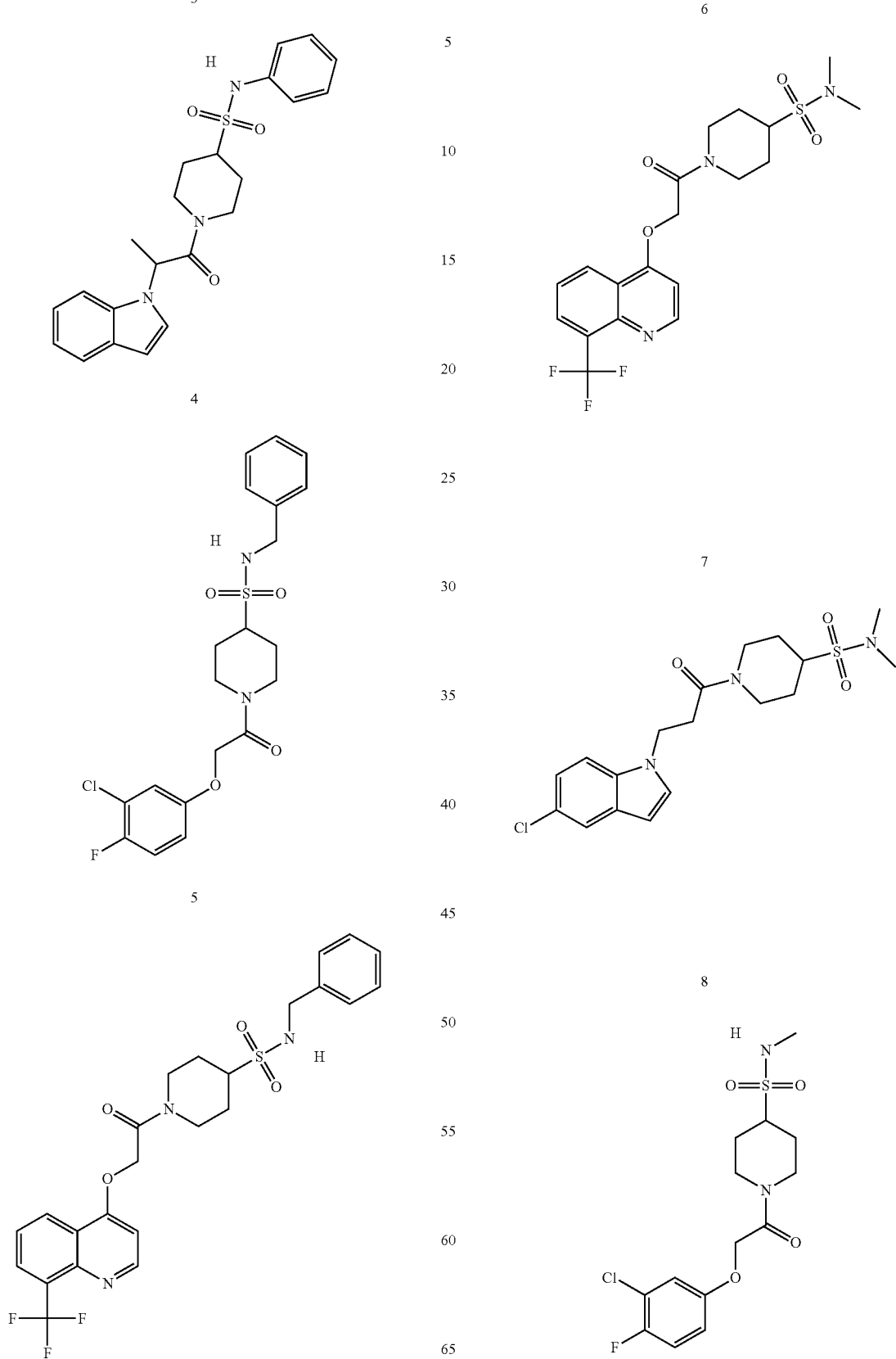

9
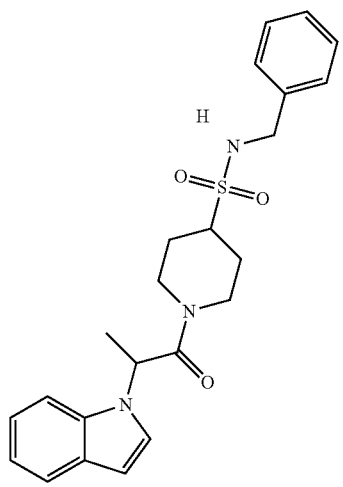
10
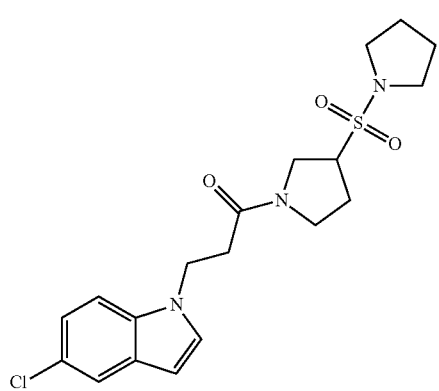
11
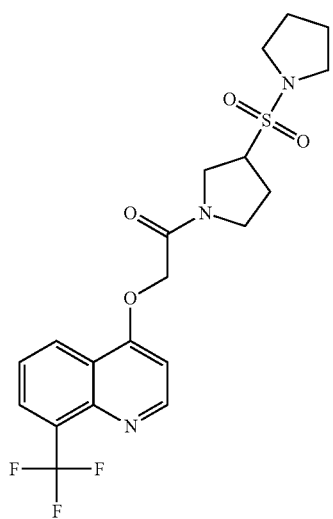
12
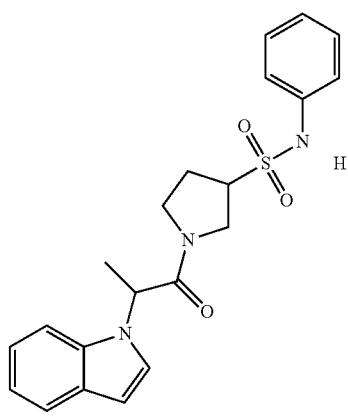
13
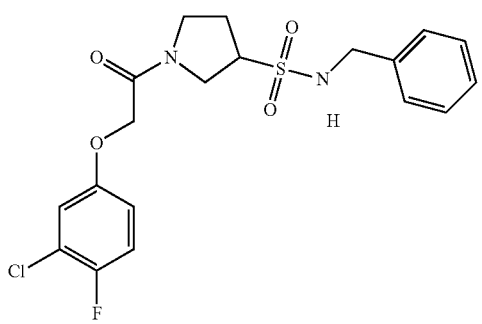
14
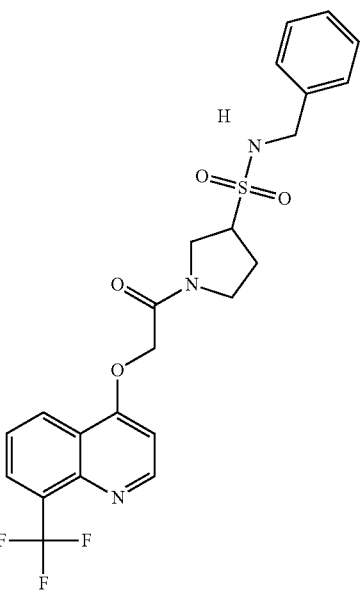

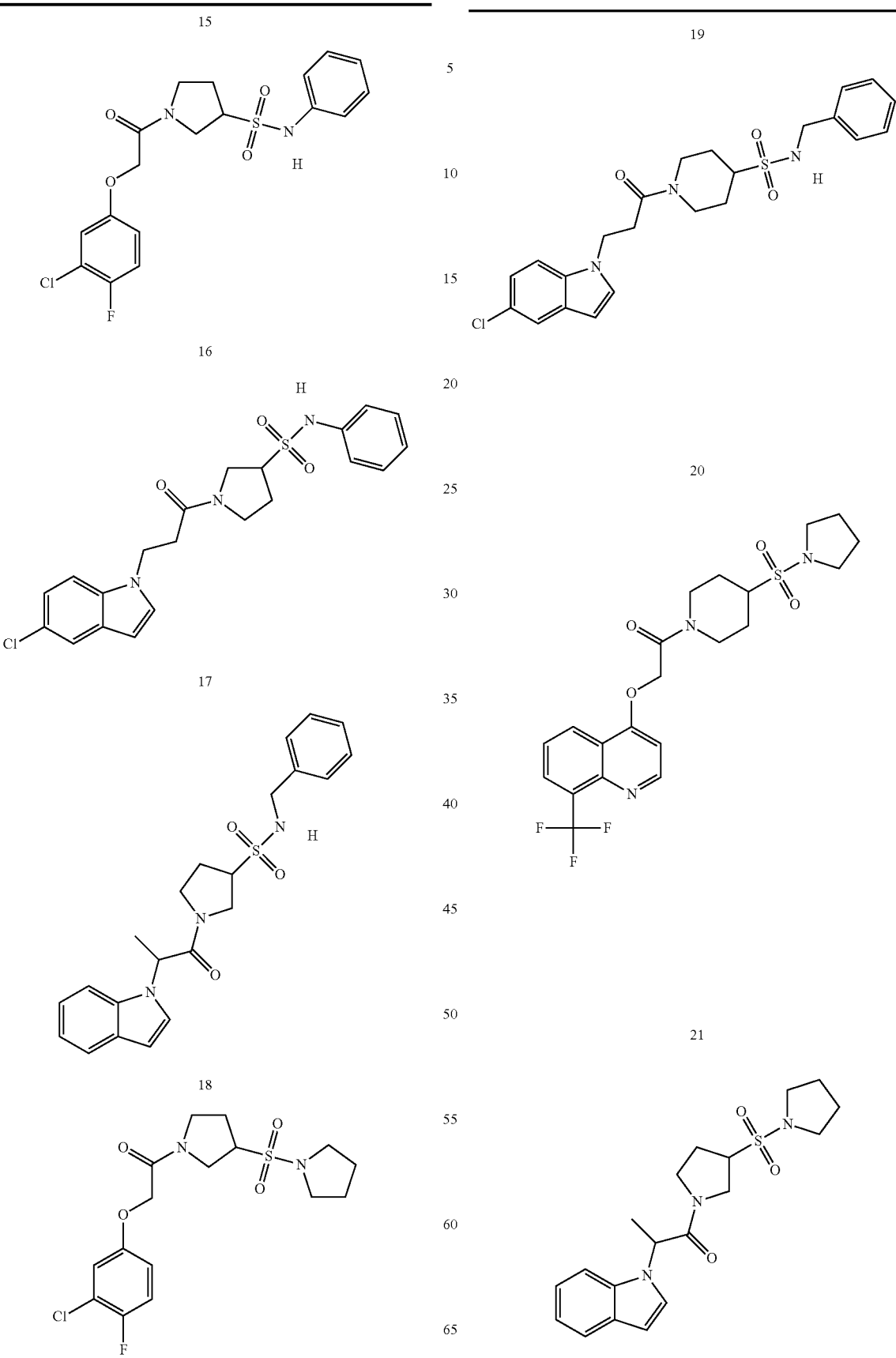

22
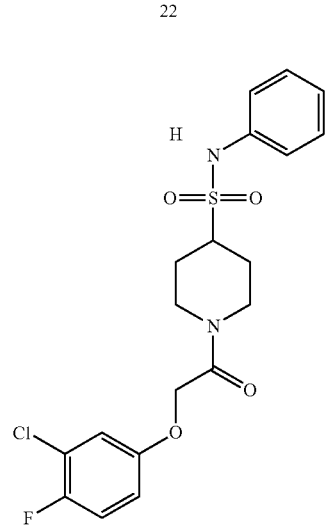
23
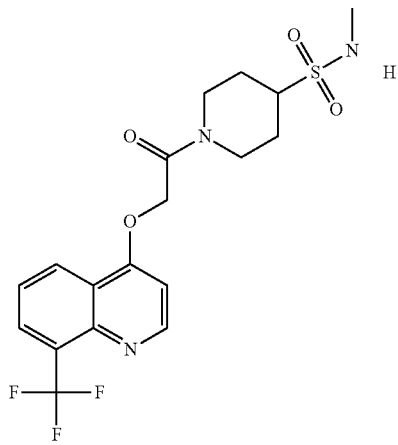
24
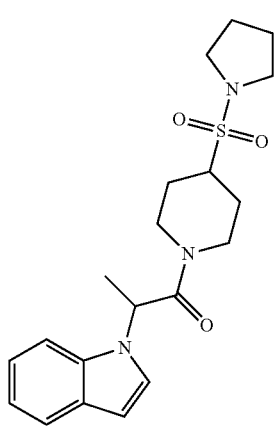
25
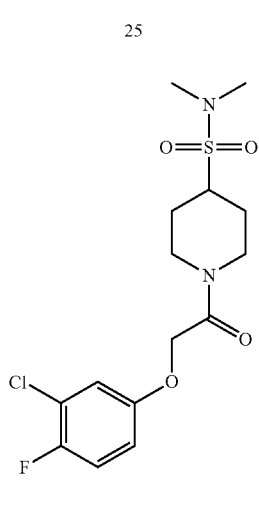
26
27
28. A method of treating acute, chronic, neuropathic, or inflammatory pain, visceral pain, osteoarthritis pain, radicular pain, back pain, head or neck pain, severe or intractable pain, nociceptive pain, breakthrough pain, postsurgical pain, or cancer pain, comprising: administering a compound having the structure of formula I:

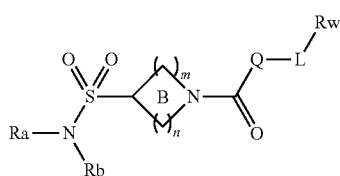

or a pharmaceutically acceptable salt thereof to a mammal, wherein:

Ring B is optionally substituted with 1-2 of halo, cyano, nitro, haloalkyl, alkoxy, sulfonyl, sulfinyl, sulfanyl, amino, carboxy, or an optionally substituted aliphatic;

each Ra is independently H, an optionally substituted aliphatic, an optionally substituted phenyl, or an optionally substituted benzyl; wherein the aliphatic, phenyl, or benzyl is optionally substituted with halo, cyano, nitro, haloalkyl, alkoxy, sulfonyl, sulfinyl, sulfanyl, amino, carboxy, or aliphatic;

each Rb is independently H, an optionally substituted aliphatic, an optionally substituted phenyl or an optionally substituted benzyl, wherein the aliphatic, phenyl, or benzyl is optionally substituted with halo, cyano, nitro, haloalkyl, alkoxy, sulfonyl, sulfinyl, sulfanyl, amino, carboxy, or aliphatic, or Ra and Rb together with the nitrogen atom to which they are bound form a heterocyclic ring, optionally substituted with halo, cyano, nitro, haloalkyl, alkoxy, sulfonyl, sulfinyl, sulfanyl, amino, carboxy, or aliphatic;

each Q is a branched or unbranched $C_1$-$C_4$-alkyl optionally substituted with halo, cyano, nitro, haloalkyl, alkoxy, sulfonyl, sulfinyl, sulfanyl, amino, carboxy, or aliphatic;

each L is absent, —O—, —NRc-, or —S—;

each Rc is H, or aliphatic optionally substituted with halo, cyano, nitro, haloalkyl, alkoxy, sulfonyl, sulfinyl, sulfanyl, amino, carboxy, or aliphatic;

each Rw is phenyl, indole, or quinoline, wherein the phenyl, indole, or quinoline is optionally substituted with halo, cyano, nitro, haloalkyl, alkoxy, sulfonyl, sulfinyl, sulfanyl, amino, carboxy, or aliphatic;

each n is 1, 2, or 3; and each m is 1, 2, or 3, provided that the sum of n and m is 3, 4, 5, or 6.

29. The method of claim 28, wherein Ra is H or aliphatic.
30. The method of claim 29, wherein Ra is H.
31. The method of claim 29, wherein Ra is aliphatic.
32. The method of claim 31, wherein Ra is methyl.
33. The method of claim 28, wherein Rb is benzyl.
34. The method of claim 28, wherein Rb is phenyl.
35. The method of claim 28, wherein Rb is aliphatic.
36. The method of claim 35, wherein Rb is alkyl.
37. The method of claim 36, wherein Rb is methyl.
38. The method of claim 28, wherein Ra and Rb together with the nitrogen atom to which they are bound form a heterocycloalkyl.
39. The method of claim 38, wherein Ra and Rb together with the nitrogen atom to which they are bound form pyrrolidinyl.
40. The method of claim 28, wherein Rw is phenyl.
41. The method of claim 40, wherein the phenyl is substituted with 1-3 of halo or haloalkyl.
42. The method of claim 28, wherein Rw is an indolyl or quinolinyl.
43. The method of claim 42, wherein Rw is an indolyl.
44. The method of claim 43, wherein the indolyl is substituted with 1-3 of halo or haloalkyl.
45. The method of claim 42, wherein Rw is quinolinyl.
46. The method of claim 45, wherein the quinolinyl is substituted with 1-3 of halo or haloalkyl.
47. The method of claim 28, wherein Q is —$CH_2$— or —C(alkyl)(H)—.
48. The method of claim 47, wherein Q is —$CH_2$—.
49. The method of claim 47, wherein Q is —C(alkyl)(H)—.
50. The method of claim 28, wherein L is O.
51. The method of claim 28, wherein n is 2.
52. The method of claim 28, wherein m is 2.
53. A method of treating acute, chronic, neuropathic, or inflammatory pain, visceral pain, osteoarthritis pain, radicular pain, back pain, head or neck pain, severe or intractable pain, nociceptive pain, breakthrough pain, postsurgical pain, or cancer pain, comprising: administering a compound having the structure of formula II:

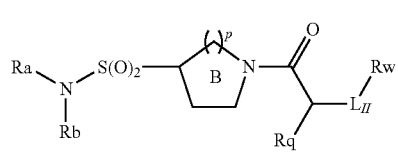

or a pharmaceutically acceptable salt thereof to a mammal, wherein ring B is optionally substituted with 1-2 of halo, cyano, nitro, haloalkyl, alkoxy, sulfonyl, sulfinyl, sulfanyl, amino, carboxy, or an optionally substituted aliphatic;

each Ra is independently H, aliphatic, phenyl or benzyl, wherein the aliphatic, phenyl, or benzyl is optionally substituted with halo, cyano, nitro, haloalkyl, alkoxy, sulfonyl, sulfinyl, sulfanyl, amino, carboxy, or aliphatic;

each Rb is independently H, aliphatic, phenyl, or benzyl wherein the aliphatic, phenyl, or benzyl is optionally substituted with halo, cyano, nitro, haloalkyl, alkoxy, sulfonyl, sulfinyl, sulfanyl, amino, carboxy, or aliphatic, or Ra and Rb together with the nitrogen atom to which they are bound form a heterocyclic ring, optionally substituted with halo, cyano, nitro, haloalkyl, alkoxy, sulfonyl, sulfinyl, sulfanyl, amino, carboxy, or aliphatic;

each Rq is H or aliphatic optionally substituted with halo, cyano, nitro, haloalkyl, alkoxy, sulfonyl, sulfinyl, sulfanyl, amino, carboxy, or aliphatic;

each $L_{II}$ is absent, —$CH_2$—, —O—, —NRc-, or —S—;

each Rc is H, or aliphatic, optionally substituted with halo, cyano, nitro, haloalkyl, alkoxy, sulfonyl, sulfinyl, sulfanyl, amino, carboxy, or aliphatic;

each Rw is phenyl, indole, or quinoline, wherein the phenyl, indole, or quinoline is optionally substituted with halo, cyano, nitro, haloalkyl, alkoxy, sulfonyl, sulfinyl, sulfanyl, amino, carboxy, or aliphatic; and each p is 1 or 2.

54. A method of treating acute, chronic, neuropathic, or inflammatory pain, visceral pain, osteoarthritis pain, radicular pain, back pain, head or neck pain, severe or intractable pain, nociceptive pain, breakthrough pain, postsurgical pain, or cancer pain, comprising administering a compound selected from:

| 87 | 88 |
|---|---|
| | -continued |
1
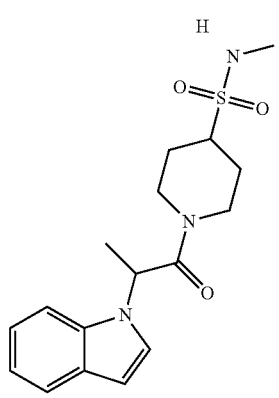
2
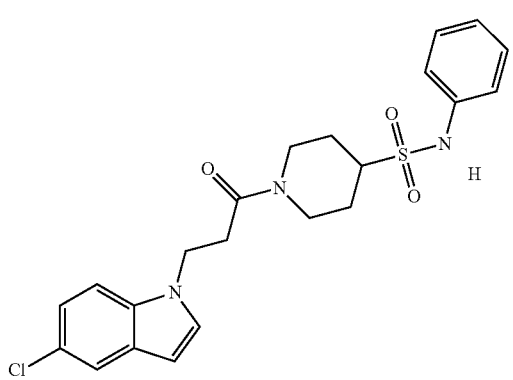
3
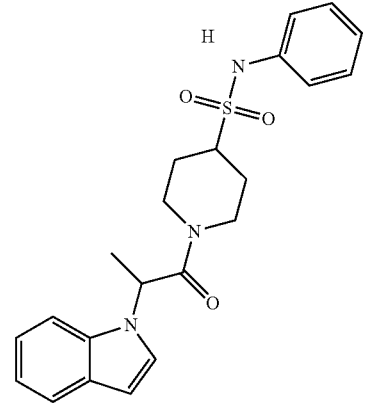
4
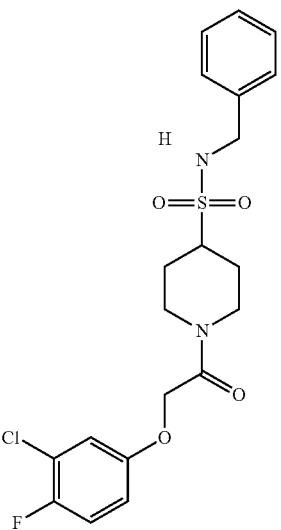
5
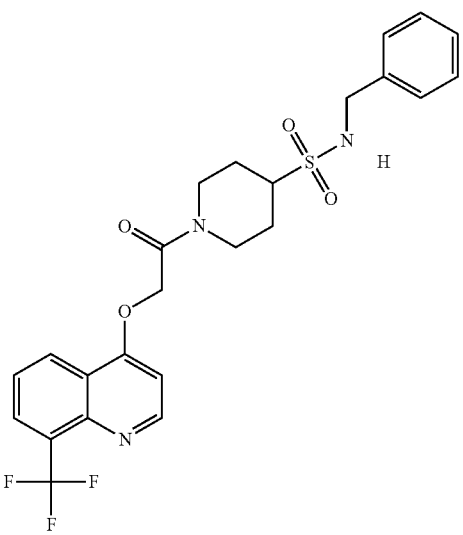
6
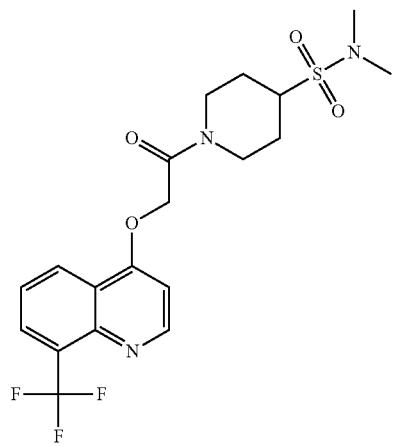

7
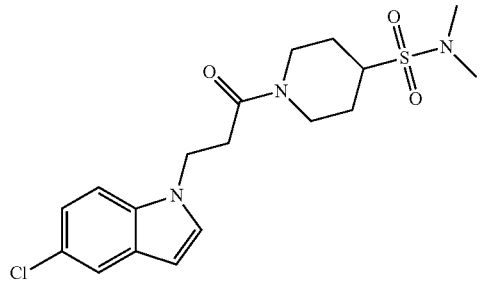
8
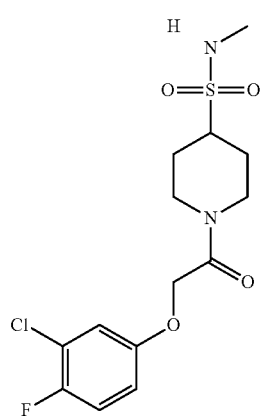
9
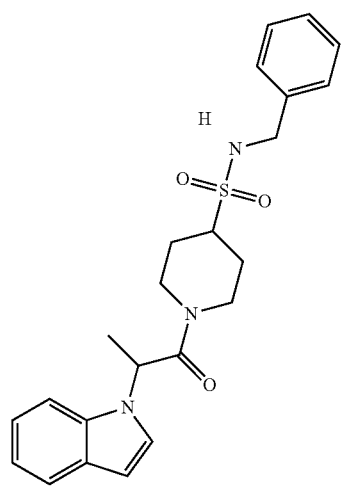
10
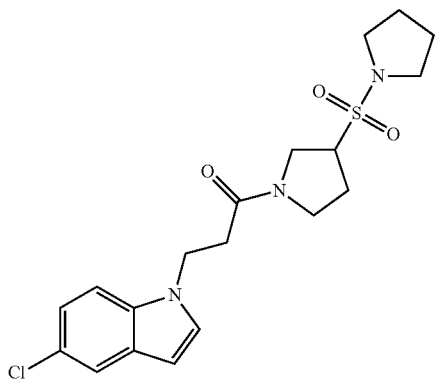
11
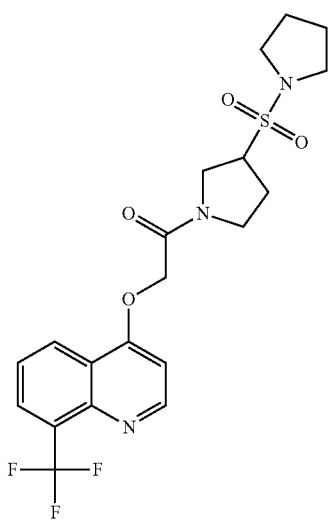
12
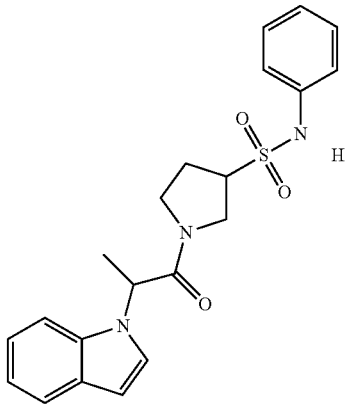

| 13 | 16 |
|---|---|
| 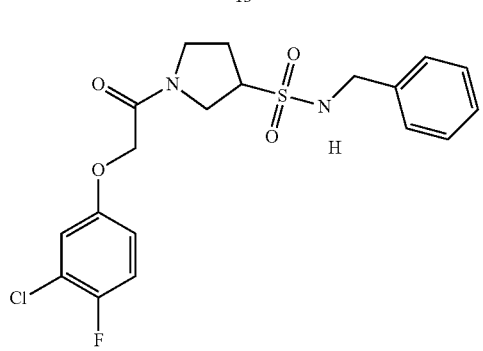 | 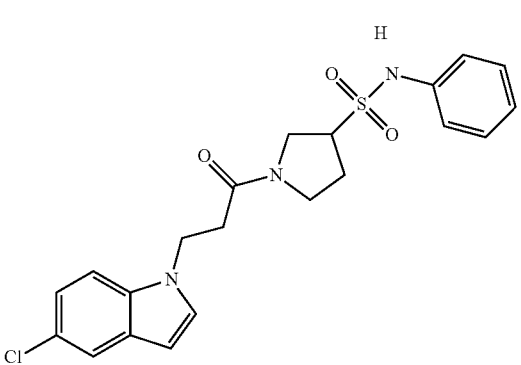 |
| 14 | 17 |
| 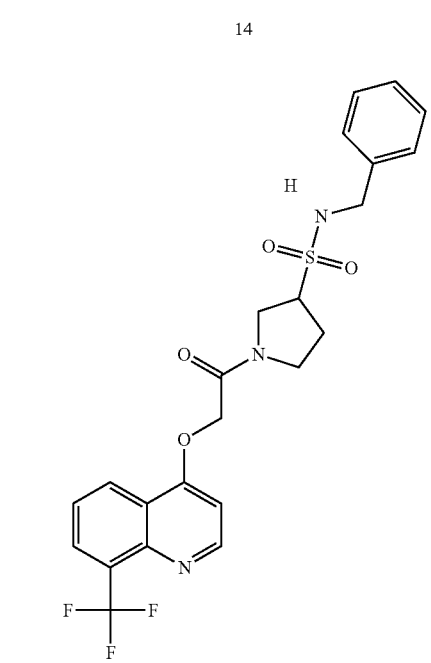 | 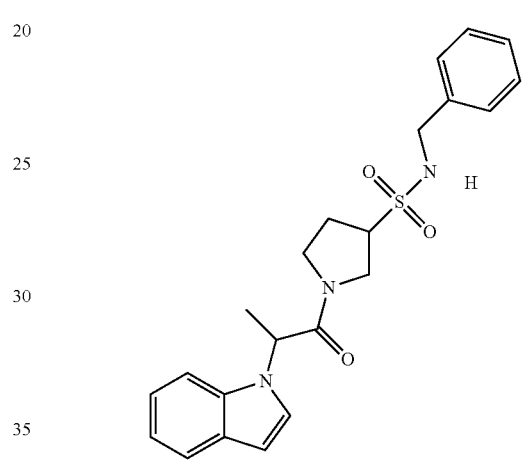 |
|  | 18 |
| 15 |  |
| 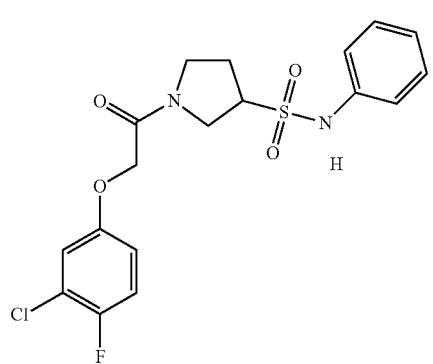 | 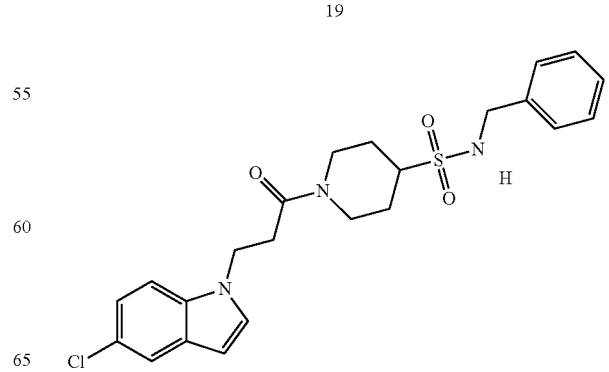 |
|  | 19 |

20
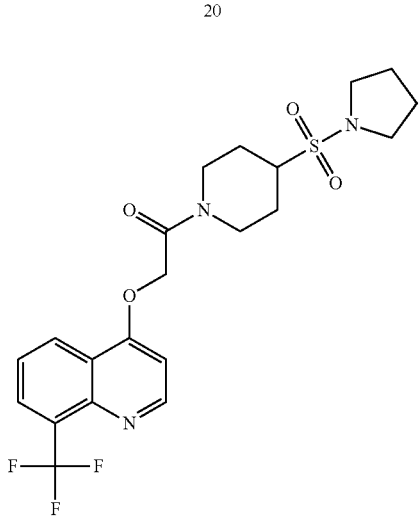
21
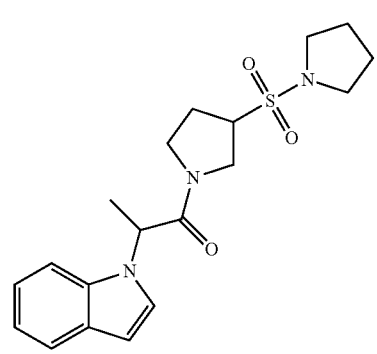
22
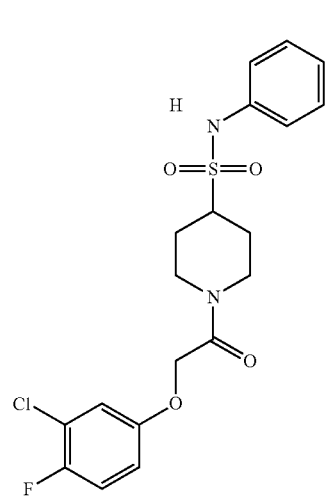
23
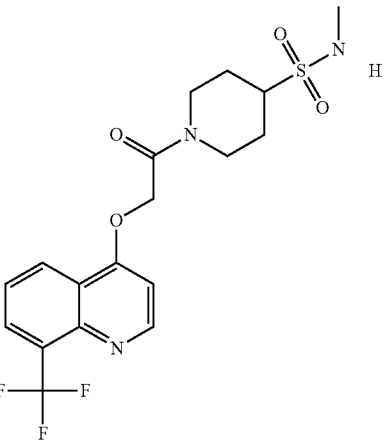
24
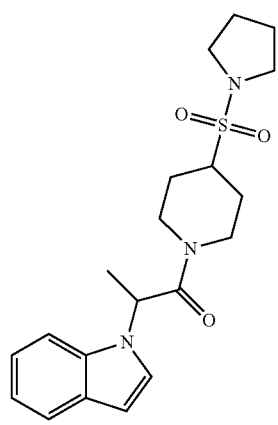
25
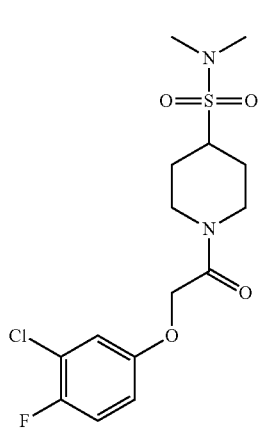

26 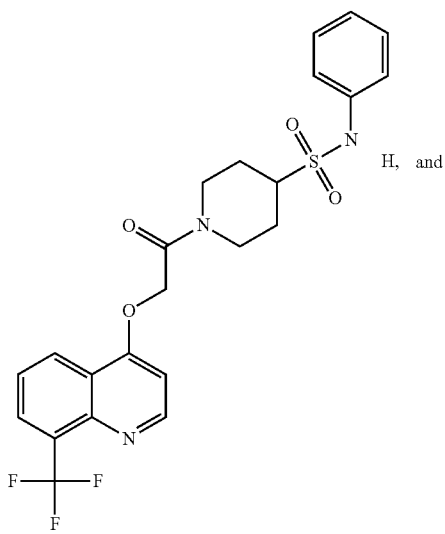 H, and
27 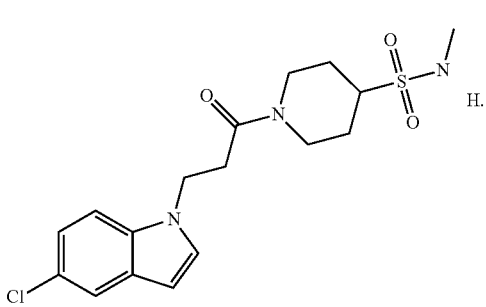 H.
* * * * *